US012168046B2

(12) United States Patent
Keller et al.

(10) Patent No.: US 12,168,046 B2
(45) Date of Patent: Dec. 17, 2024

(54) MYCOBACTERIAL ANTIGEN COMPOSITIONS AND METHODS OF USE

(71) Applicant: Children's National Medical Center, Washington, DC (US)

(72) Inventors: Michael Keller, Laurel, MD (US); Catherine Bollard, Bethesda, MD (US); Patrick Hanley, Washington, DC (US); Conrad Russell Cruz, Bethesda, MD (US); Haili Lang, Derwood, MD (US); Shabnum Patel, Washington, DC (US)

(73) Assignee: Children's National Medical Center, Washington, DC (US)

( * ) Notice: Subject to any disclaimer, the term of this patent is extended or adjusted under 35 U.S.C. 154(b) by 876 days.

(21) Appl. No.: 17/050,829

(22) PCT Filed: Apr. 26, 2019

(86) PCT No.: PCT/US2019/029505
§ 371 (c)(1),
(2) Date: Oct. 26, 2020

(87) PCT Pub. No.: WO2019/210282
PCT Pub. Date: Oct. 31, 2019

(65) Prior Publication Data
US 2021/0290747 A1    Sep. 23, 2021

Related U.S. Application Data

(60) Provisional application No. 62/663,239, filed on Apr. 26, 2018.

(51) Int. Cl.
| | | |
|---|---|---|
| A61K 39/04 | (2006.01) | |
| A61P 31/06 | (2006.01) | |
| C12N 5/0783 | (2010.01) | |
| A61K 39/00 | (2006.01) | |

(52) U.S. Cl.
CPC .............. *A61K 39/04* (2013.01); *A61P 31/06* (2018.01); *C12N 5/0636* (2013.01); *A61K 2039/5158* (2013.01); *A61K 2039/70* (2013.01); *C12N 2501/2304* (2013.01); *C12N 2501/2307* (2013.01); *C12N 2501/2315* (2013.01); *C12N 2501/2321* (2013.01); *C12N 2501/24* (2013.01); *C12N 2501/25* (2013.01)

(58) Field of Classification Search
CPC .................................................... A61K 39/04
See application file for complete search history.

(56) References Cited

U.S. PATENT DOCUMENTS

| | | | |
|---|---|---|---|
| 2009/0124549 A1 | 5/2009 | Lewinsohn et al. | |
| 2011/0081377 A1 | 4/2011 | Roederer et al. | |
| 2016/0022795 A1* | 1/2016 | Triccas ................... | A61P 31/06 |
| | | | 435/194 |

FOREIGN PATENT DOCUMENTS

| | | |
|---|---|---|
| WO | WO-2008-124647 A2 | 10/2008 |
| WO | WO-2009-117134 A2 | 9/2009 |
| WO | WO 2010-121618 A1 | 12/2010 |
| WO | WO-2014-009438 A2 | 1/2014 |
| WO | WO-2016-030526 A1 | 3/2016 |
| WO | WO-2017-223146 A1 | 12/2017 |

OTHER PUBLICATIONS

Wu, et al., "Gamma Delta T Cells and Their Potential for Immunotheraphy" Int. J. Biol.Sci. 2014, vol. 10(2); pp. 119-135.
Esin S., et al., "Proliferation of distinct human T cell subsets in response to live, killed or soluble extracts of Mycobacterium tuberculosis and Myco. Avium"; Oct. 29, 2003, Clinical And Experimental Immunology., vol. 103, No. 3, pp. 419-425.
Patel, Shabnum, et al.,"Mycobacteria-Specific T Cells May Be Expanded From Healthy Donors and Are Near Absent in Primary Immunodeficiency Disorders"; Mar. 29, 2019, Frontiers in Immunology, vol. 10, p. 621.
Shreemanta K. Parida, et al. "T-Cell Therapy: Options for Infectious Diseases" Sep. 25, 2015, Clinical Infectious Diseases, vol. 61, No. Suppl.3, Pages S217-S224.
European Search Opinion issued in Corresponding EP Appin. No. 19793777 on Feb. 25, 2022 citing references 15, 16, 17, 18, 24, and 25 listed therein.
Supplementary European Search Report issued in Corresponding EP Appln. No. 19793777, on Feb. 9, 2022 citing references 19, 20, 26 listed therein.

* cited by examiner

*Primary Examiner* — Albert M Navarro
(74) *Attorney, Agent, or Firm* — Oblon, McClelland, Maier & Neustadt, L.L.P.

(57) ABSTRACT

The present disclosure relates, at least in part, to mycobacterial polynucleotides and polypeptides, to fragments or variants thereof, to cells comprising the mycobacterial polynucleotides and polypeptides, to cells comprising the mycobacterial polynucleotides and polypeptides, that are engineered to expand T-cells ex vivo, and to methods of use thereof.

3 Claims, 12 Drawing Sheets
Specification includes a Sequence Listing.

| Peptide 7 (AA 61-75) | DIKVQFQSGGNNSPA | Identify |
|---|---|---|
| M Bovis | DIKVQFQSGGNNSPA | 100% |
| M Avium | DIKVQFQSGGNGSPA | 93% |
| M Intracellulare | DIKVQFQSGGNGSPA | 93% |
| M Kansasii | DIKVQFQSGGANSPA | 93% |
| M Abscessus | EIKVQFQNGGAKS | 67% |

| Peptide 15 (AA 141-155) | LTSELPQWLSANRAV | Identify |
|---|---|---|
| M Bovis | LTSELPQWLSANRAV | 100% |
| M Avium | LSSELPDWLAAN | 75% |
| M Intracellulare | LTSELPQYLASNKSV | 67% |
| M Kansasii | LTSELPQWLSANRSV | 93% |
| M Abscessus | LTTELPQWLGAN | 67% |

| Peptide 14 (AA 131-145) | GCQTYKWETFLTSEL | Identify |
|---|---|---|
| M Bovis | GCQTYKWETFLTSEL | 100% |
| M Avium | GCTTYKWETFLTSEL | 93% |
| M Intracellulare | GCTTYKWETFLTSEL | 93% |
| M Kansasii | GCTTYKWETFLTSEL | 93% |
| M Abscessus | TYKWETFLTTEL | 73% |

| Peptide 19 (AA 181-195) | QQFIYAGSLSALLDP | Identify |
|---|---|---|
| M Bovis | QQFIYAGSLSALLDP | 100% |
| M Avium | QFIYAGSLSALLDP | 100% |
| M Intracellulare | QFVYAGSLSALLDP | 93% |
| M Kansasii | QQFIYAGSLSALMDP | 93% |
| M Abscessus | QQFIYAGALSGFLHP | 73% |

FIG. 11

| Peptide 8(AA 71-85) | EISTNIRQAGVQYSR | Identify |
|---|---|---|
| M Bovis | EISTNIRQAGVQYSR | 100% |
| M Avium | EISTEIRQ | 46% |
| M Intracellulare | EISTEIRQA | 53% |
| M Kankasii | EISTNIRQAGVQYS | 93% |
| M Abscessus | ISQNIRESGLQY | 53% |

| Peptide 10 (AA 85-100) | ADDEEQQQALSSQMGF | Identify |
|---|---|---|
| M Bovis | QALSAQM | 40% |
| M Avium | ANEEQQQSWATQ | 58% |
| M Intracellulare | DEERAQQQQAL | 53% |
| M Kankasii | QQQALADQLGF | 53% |
| M Abscessus | ADEEQLRALS | 53% |

| Peptide 9(AA 80-95) | VQYSRADEEQQQALS | Identify |
|---|---|---|
| M Bovis | YARELTDDERAQQQKAL | 53% |
| M Avium | YARELTDEERAQQQQAL | 59% |
| M Intracellulare | YARELTDEERAQQQQAL | 59% |
| M Kansasii | VQYSKADEEQQQALS | 93% |
| M Abscessus | YARELTDEERQKQQQAL | 59% |

FIG. 12

SEQUENCE LISTING

<160> NUMBER OF SEQ ID NOS: 63

<210> SEQ ID NO 1
<211> LENGTH: 978
<212> TYPE: DNA
<213> ORGANISM: Homo sapiens

<400> SEQUENCE: 1

```
atgacagacg tgagccgaaa gattcgagct tggggacgcc gattgatgat cggcacggca      60
gcggctgtag tccttccggg cctggtgggg cttgccggcg gagcggcaac cgcgggcgcg     120
ttctcccggc cggggctgcc ggtcgagtac ctgcaggtgc cgtcgccgtc gatgggccgc     180
gacatcaagg ttcagttcca gagcggtggg aacaactcac ctgcggttta tctgctcgac     240
ggcctgcgcg cccaagacga ctacaacggc tgggatatca cacccccggc gttcgagtgg     300
tactaccagt cgggactgtc gatagtcatg ccggtcggcg ggcagtccag cttctacagc     360
gactggtaca gcccggcctg cggtaaggct ggctgccaga cttacaagtg ggaaaccttc     420
ctgaccagcg agctgccgca atggttgtcc gccaacaggg ccgtgaagcc caccggcagc     480
gctgcaatcg gcttgtcgat ggccggctcg tcggcaatga tcttggccgc ctaccacccc     540
cagcagttca tctacgccgg ctcgctgtcg gccctgctgg acccctctca ggggatgggg     600
cctagcctga tcggcctcgc gatgggtgac gccggcggtt acaaggccgc agacatgtgg     660
ggtccctcga gtgacccggc atgggagcgc aacgacccta cgcagcagat ccccaagctg     720
gtcgcaaaca acacccggct atgggtttat tgcgggaacg gcaccccgaa cgagttgggc     780
ggtgccaaca tacccgccga gttcttggag aacttcgttc gtagcagcaa cctgaagttc     840
caggatgcgt acaacgccgc gggcgggcac aacgccgtgt tcaacttccc gcccaacggc     900
acgcacagct gggagtactg gggcgctcag ctcaacgcca tgaagggtga cctgcagagt     960
tcgttaggcg ccggctga                                                   978
```

<210> SEQ ID NO 2
<211> LENGTH: 1107
<212> TYPE: DNA
<213> ORGANISM: Homo sapiens

<400> SEQUENCE: 2

```
atgctgtggc acgcaatgcc accggagcta ataccgcac ggctgatggc cggcgcgggt        60
ccggctccaa tgcttgcggc ggccgcggga tggcagacgc tttcggcggc tctggacgct     120
caggccgtcg agttgaccgc gcgcctgaac tctctgggag aagcctggac tggaggtggc     180
agcgacaagg cgcttgcggc tgcaacgccg atggtgtct ggctacaaac cgcgtcaaca      240
caggccaaga cccgtgcgat gcaggcgacg gcgcaagccg cggcatacac ccaggccatg     300
gccacgacgc cgtcgctgcc ggagatcgcc gccaaccaca tcacccaggc cgtccttacg     360
gccaccaact tcttcggtat caacacgatc ccgatcgcgt tgaccgagat ggattatttc     420
atccgtatgt ggaaccaggc agccctggca atggaggtct accaggccga gaccgcggtt     480
aacacgcttt tcgagaagct cgagccgatg gcgtcgatcc ttgatcccgg cgcgagccag     540
```

| | |
|---|---|
| agcacgacga acccgatctt cggaatgccc tccccctggca gctcaacacc ggttggccag | 600 |
| ttgccgccgg cggctaccca gaccctcggc caactgggtg agatgagcgg cccgatgcag | 660 |
| cagctgaccc agccgctgca gcaggtgacg tcgttgttca gccaggtggg cggcaccggc | 720 |
| ggcggcaacc cagccgacga ggaagccgcg cagatgggcc tgctcggcac cagtccgctg | 780 |
| tcgaaccatc cgctggctgg tggatcaggc cccagcgcgg gcgcgggcct gctgcgcgcg | 840 |
| gagtcgctac ctggcgcagg tgggtcgttg acccgcacgc cgctgatgtc tcagctgatc | 900 |
| gaaaagccgg ttgcccccctc ggtgatgccg gcggctgctg ccggatcgtc ggcgacgggt | 960 |
| ggcgccgctc cggtgggtgc gggagcgatg ggccagggtg cgcaatccgg cggctccacc | 1020 |
| aggccgggtc tggtcgcgcc ggcaccgctc gcgcaggagc gtgaagaaga cgacgaggac | 1080 |
| gactgggacg aagaggacga ctggtga | 1107 |

<210> SEQ ID NO 3
<211> LENGTH: 288
<212> TYPE: DNA
<213> ORGANISM: Homo sapiens

<400> SEQUENCE: 3

| | |
|---|---|
| atgacagagc agcagtggaa tttcgcgggt atcgaggccg cggcaagcgc aatccaggga | 60 |
| aatgtcacgt ccattcattc cctccttgac gaggggaagc agtccctgac caagctcgca | 120 |
| gcggcctggg gcggtagcgg ttcggaggcg taccaggggtg tccagcaaaa atgggacgcc | 180 |
| acggctaccg agctgaacaa cgcgctgcag aacctggcgc ggacgatcag cgaagccggt | 240 |
| caggcaatgg cttcgaccga aggcaacgtc actgggatgt tcgcatag | 288 |

<210> SEQ ID NO 4
<211> LENGTH: 303
<212> TYPE: DNA
<213> ORGANISM: Homo sapiens

<400> SEQUENCE: 4

| | |
|---|---|
| atggcagaga tgaagaccga tgccgctacc ctcgcgcagg aggcaggtaa tttcgagcgg | 60 |
| atctccggcg acctgaaaac ccagatcgac caggtggagt cgacggcagg ttcgttgcag | 120 |
| ggccagtggc gcggcgcggc ggggacggcc gcccaggccg cggtggtgcg cttccaagaa | 180 |
| gcagccaata agcagaagca ggaactcgac gagatctcga cgaatattcg tcaggccggc | 240 |
| gtccaatact cgagggccga cgaggagcag cagcaggcgc tgtcctcgca aatgggcttc | 300 |
| tga | 303 |

<210> SEQ ID NO 5
<211> LENGTH: 546
<212> TYPE: DNA
<213> ORGANISM: Homo sapiens

<400> SEQUENCE: 5

| | |
|---|---|
| gtgagagttt tgttgctggg accgcccggg gcgggcaagg ggacgcaggc ggtgaagctg | 60 |
| gccgagaagc tcgggatccc gcagatctcc accggcgaac tcttccggcg caacatcgaa | 120 |
| gagggcacca agctcggcgt ggaagccaaa cgctacttgg atgccggtga cttggtgccg | 180 |
| tccgacttga ccaatgaact cgtcgacgac cggctgaaca tccggacgc ggccaacgga | 240 |
| ttcatcttgg atggctatcc acgctcggtc gagcaggcca aggcgcttca cgagatgctc | 300 |
| gaacgccggg ggaccgacat cgacgcggtg ctggagtttc gtgtgtccga ggaggtgttg | 360 |
| ttggagcgac tcaaggggcg tggccgcgcc gacgacaccg acgacgtcat cctcaaccgg | 420 |

```
atgaaggtct accgcgacga gaccgcgccg ctgctggagt actaccgcga ccaattgaag    480
accgtcgacg ccgtcggcac catggacgag gtgttcgccc gtgcgttgcg ggctctggga    540
aagtag                                                               546
```

<210> SEQ ID NO 6
<211> LENGTH: 325
<212> TYPE: PRT
<213> ORGANISM: Homo sapiens

<400> SEQUENCE: 6

```
Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
                20                  25                  30

Gly Gly Ala Ala Thr Ala Gly Ala Phe Ser Arg Pro Gly Leu Pro Val
            35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325
```

-continued

<210> SEQ ID NO 7
<211> LENGTH: 368
<212> TYPE: PRT
<213> ORGANISM: Homo sapiens

<400> SEQUENCE: 7

Met Leu Trp His Ala Met Pro Pro Glu Leu Asn Thr Ala Arg Leu Met
1               5                   10                  15

Ala Gly Ala Gly Pro Ala Pro Met Leu Ala Ala Ala Gly Trp Gln
            20                  25                  30

Thr Leu Ser Ala Ala Leu Asp Ala Gln Ala Val Glu Leu Thr Ala Arg
        35                  40                  45

Leu Asn Ser Leu Gly Glu Ala Trp Thr Gly Gly Ser Asp Lys Ala
50                  55                  60

Leu Ala Ala Ala Thr Pro Met Val Val Trp Leu Gln Thr Ala Ser Thr
65                  70                  75                  80

Gln Ala Lys Thr Arg Ala Met Gln Ala Thr Ala Gln Ala Ala Tyr
                85                  90                  95

Thr Gln Ala Met Ala Thr Thr Pro Ser Leu Pro Glu Ile Ala Ala Asn
            100                 105                 110

His Ile Thr Gln Ala Val Leu Thr Ala Thr Asn Phe Phe Gly Ile Asn
        115                 120                 125

Thr Ile Pro Ile Ala Leu Thr Glu Met Asp Tyr Phe Ile Arg Met Trp
130                 135                 140

Asn Gln Ala Ala Leu Ala Met Glu Val Tyr Gln Ala Glu Thr Ala Val
145                 150                 155                 160

Asn Thr Leu Phe Glu Lys Leu Glu Pro Met Ala Ser Ile Leu Asp Pro
                165                 170                 175

Gly Ala Ser Gln Ser Thr Thr Asn Pro Ile Phe Gly Met Pro Ser Pro
            180                 185                 190

Gly Ser Ser Thr Pro Val Gly Gln Leu Pro Pro Ala Thr Gln Thr
        195                 200                 205

Leu Gly Gln Leu Gly Glu Met Ser Gly Pro Met Gln Gln Leu Thr Gln
210                 215                 220

Pro Leu Gln Gln Val Thr Ser Leu Phe Ser Gln Val Gly Gly Thr Gly
225                 230                 235                 240

Gly Gly Asn Pro Ala Asp Glu Glu Ala Ala Gln Met Gly Leu Leu Gly
                245                 250                 255

Thr Ser Pro Leu Ser Asn His Pro Leu Ala Gly Gly Ser Gly Pro Ser
            260                 265                 270

Ala Gly Ala Gly Leu Leu Arg Ala Glu Ser Leu Pro Gly Ala Gly Gly
        275                 280                 285

Ser Leu Thr Arg Thr Pro Leu Met Ser Gln Leu Ile Glu Lys Pro Val
290                 295                 300

Ala Pro Ser Val Met Pro Ala Ala Ala Gly Ser Ser Ala Thr Gly
305                 310                 315                 320

Gly Ala Ala Pro Val Gly Ala Gly Ala Met Gly Gln Gly Ala Gln Ser
                325                 330                 335

Gly Gly Ser Thr Arg Pro Gly Leu Val Ala Pro Ala Pro Leu Ala Gln
            340                 345                 350

Glu Arg Glu Glu Asp Glu Asp Asp Trp Asp Glu Asp Asp Trp
        355                 360                 365

<210> SEQ ID NO 8
<211> LENGTH: 95

<212> TYPE: PRT
<213> ORGANISM: Homo sapiens

<400> SEQUENCE: 8

Met Thr Glu Gln Gln Trp Asn Phe Ala Gly Ile Glu Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 9
<211> LENGTH: 100
<212> TYPE: PRT
<213> ORGANISM: Homo sapiens

<400> SEQUENCE: 9

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 10
<211> LENGTH: 181
<212> TYPE: PRT
<213> ORGANISM: Homo sapiens

<400> SEQUENCE: 10

Met Arg Val Leu Leu Leu Gly Pro Pro Gly Ala Gly Lys Gly Thr Gln
1               5                   10                  15

Ala Val Lys Leu Ala Glu Lys Leu Gly Ile Pro Gln Ile Ser Thr Gly
            20                  25                  30

Glu Leu Phe Arg Arg Asn Ile Glu Glu Gly Thr Lys Leu Gly Val Glu
        35                  40                  45

Ala Lys Arg Tyr Leu Asp Ala Gly Asp Leu Val Pro Ser Asp Leu Thr
    50                  55                  60

Asn Glu Leu Val Asp Asp Arg Leu Asn Asn Pro Asp Ala Ala Asn Gly
65                  70                  75                  80

Phe Ile Leu Asp Gly Tyr Pro Arg Ser Val Glu Gln Ala Lys Ala Leu
                85                  90                  95

His Glu Met Leu Glu Arg Arg Gly Thr Asp Ile Asp Ala Val Leu Glu

```
                    100                 105                 110
Phe Arg Val Ser Glu Glu Val Leu Leu Glu Arg Leu Lys Gly Arg Gly
                115                 120                 125

Arg Ala Asp Asp Thr Asp Val Ile Leu Asn Arg Met Lys Val Tyr
        130                 135                 140

Arg Asp Glu Thr Ala Pro Leu Leu Glu Tyr Tyr Arg Asp Gln Leu Lys
145                 150                 155                 160

Thr Val Asp Ala Val Gly Thr Met Asp Glu Val Phe Ala Arg Ala Leu
                165                 170                 175

Arg Ala Leu Gly Lys
            180
```

<210> SEQ ID NO 11
<211> LENGTH: 153
<212> TYPE: PRT
<213> ORGANISM: Homo sapiens

<400> SEQUENCE: 11

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
            35                  40                  45

Thr Glu Leu Thr Val Thr Asp Ile Phe Ala Ala Ser Lys Asn Thr Thr
50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

<210> SEQ ID NO 12
<211> LENGTH: 177
<212> TYPE: PRT
<213> ORGANISM: Homo sapiens

<400> SEQUENCE: 12

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
        50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
```

```
                    85                  90                  95
Thr Gly Asp Phe Asp Leu His Leu Leu Lys Val Ser Glu Gly Thr Thr
                100                 105                 110

Ile Leu Leu Asn Cys Thr Gly Gln Val Lys Gly Arg Lys Pro Ala Ala
            115                 120                 125

Leu Gly Glu Ala Gln Pro Thr Lys Ser Leu Glu Glu Asn Lys Ser Leu
        130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 13
<211> LENGTH: 162
<212> TYPE: PRT
<213> ORGANISM: Homo sapiens

<400> SEQUENCE: 13

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
                100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
        130                 135                 140

Gln Lys Met Ile His Gln His Leu Ser Ser Arg Thr His Gly Ser Glu
145                 150                 155                 160

Asp Ser

<210> SEQ ID NO 14
<211> LENGTH: 162
<212> TYPE: PRT
<213> ORGANISM: Homo sapiens

<400> SEQUENCE: 14

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60
```

```
Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser

<210> SEQ ID NO 15
<211> LENGTH: 195
<212> TYPE: PRT
<213> ORGANISM: Homo sapiens

<400> SEQUENCE: 15

Met Ala Leu Leu Phe Pro Leu Leu Ala Ala Leu Val Met Thr Ser Tyr
 1               5                  10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
 50                  55                  60

Met Val Lys Gly Ser Gln Leu Gln Lys Ala His Val Met Ser Val Leu
 65                  70                  75                  80

His Glu Met Leu Gln Gln Ile Phe Ser Leu Phe His Thr Glu Arg Ser
                 85                  90                  95

Ser Ala Ala Trp Asn Met Thr Leu Leu Asp Gln Leu His Thr Glu Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Pro Ala Leu Thr Leu Arg
130                 135                 140

Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175

Leu Ser Thr Asn Met Gln Glu Arg Leu Arg Ser Lys Asp Arg Asp Leu
            180                 185                 190

Gly Ser Ser
        195

<210> SEQ ID NO 16
<211> LENGTH: 431
<212> TYPE: PRT
<213> ORGANISM: Homo sapiens

<400> SEQUENCE: 16

Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
```

```
                  20                  25                  30
Leu Asp Asn Glu Val His Ser Ser Phe Ile His Arg Arg Leu Arg Ser
            35                  40                  45
Gln Glu Arg Glu Met Gln Arg Glu Ile Leu Ser Ile Leu Gly Leu
        50                  55                  60
Pro His Arg Pro Arg Pro His Leu Gln Gly Lys His Asn Ser Ala Pro
65                  70                  75                  80
Met Phe Met Leu Asp Leu Tyr Asn Ala Met Ala Val Glu Glu Gly Gly
                85                  90                  95
Gly Pro Gly Gly Gln Gly Phe Ser Tyr Pro Tyr Lys Ala Val Phe Ser
            100                 105                 110
Thr Gln Gly Pro Pro Leu Ala Ser Leu Gln Asp Ser His Phe Leu Thr
        115                 120                 125
Asp Ala Asp Met Val Met Ser Phe Val Asn Leu Val Glu His Asp Lys
        130                 135                 140
Glu Phe Phe His Pro Arg Tyr His His Arg Glu Phe Arg Phe Asp Leu
145                 150                 155                 160
Ser Lys Ile Pro Glu Gly Glu Ala Val Thr Ala Ala Glu Phe Arg Ile
            165                 170                 175
Tyr Lys Asp Tyr Ile Arg Glu Arg Phe Asp Asn Glu Thr Phe Arg Ile
            180                 185                 190
Ser Val Tyr Gln Val Leu Gln Glu His Leu Gly Arg Glu Ser Asp Leu
        195                 200                 205
Phe Leu Leu Asp Ser Arg Thr Leu Trp Ala Ser Glu Glu Gly Trp Leu
    210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
            245                 250                 255
Ile Asn Pro Lys Leu Ala Gly Leu Ile Gly Arg His Gly Pro Gln Asn
            260                 265                 270
Lys Gln Pro Phe Met Val Ala Phe Phe Lys Ala Thr Glu Val His Phe
        275                 280                 285
Arg Ser Ile Arg Ser Thr Gly Ser Lys Gln Arg Ser Gln Asn Arg Ser
    290                 295                 300
Lys Thr Pro Lys Asn Gln Glu Ala Leu Arg Met Ala Asn Val Ala Glu
305                 310                 315                 320
Asn Ser Ser Ser Asp Gln Arg Gln Ala Cys Lys Lys His Glu Leu Tyr
            325                 330                 335
Val Ser Phe Arg Asp Leu Gly Trp Gln Asp Trp Ile Ile Ala Pro Glu
        340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
    370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
            405                 410                 415
Leu Lys Lys Tyr Arg Asn Met Val Val Arg Ala Cys Gly Cys His
            420                 425                 430

<210> SEQ ID NO 17
```

```
<211> LENGTH: 15
<212> TYPE: PRT
<213> ORGANISM: Artificial Sequence
<220> FEATURE:
<223> OTHER INFORMATION: Antigen 1

<400> SEQUENCE: 17

Asp Ile Lys Val Gln Phe Gln Ser Gly Gly Asn Asn Ser Pro Ala
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: antigen 2

<400> SEQUENCE: 18

Asp Ile Lys Val Gln Phe Gln Ser Gly Gly Asn Asn Ser Pro Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: antigen 3

<400> SEQUENCE: 19

Asp Ile Lys Val Gln Phe Gln Ser Gly Gly Asn Gly Ser Pro Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: antigen 4

<400> SEQUENCE: 20

Asp Ile Lys Val Gln Phe Gln Ser Gly Gly Asn Gly Ser Pro Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: antigen 5

<400> SEQUENCE: 21

Asp Ile Lys Val Gln Phe Gln Ser Gly Gly Ala Asn Ser Pro Ala
1               5                   10                  15

<210> SEQ ID NO 22
<211> LENGTH: 13
<212> TYPE: PRT
<213> ORGANISM: Artificial Sequence
<220> FEATURE:
<223> OTHER INFORMATION: antigen 6

<400> SEQUENCE: 22

Glu Ile Lys Val Gln Phe Gln Asn Gly Gly Ala Lys Ser
1               5                   10

<210> SEQ ID NO 23
<211> LENGTH: 15
```

```
<212> TYPE: PRT
<213> ORGANISM: Artificial Sequence
<220> FEATURE:
<223> OTHER INFORMATION: antigen 6

<400> SEQUENCE: 23

Gly Cys Gln Thr Tyr Lys Trp Glu Thr Phe Leu Thr Ser Glu Leu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: antigen 8

<400> SEQUENCE: 24

Gly Cys Gln Thr Tyr Lys Trp Glu Thr Phe Leu Thr Ser Glu Leu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: antigen 9

<400> SEQUENCE: 25

Gly Cys Thr Thr Tyr Lys Trp Glu Thr Phe Leu Thr Ser Glu Leu
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: antigen 10

<400> SEQUENCE: 26

Gly Cys Thr Thr Tyr Lys Trp Glu Thr Phe Leu Thr Ser Glu Leu
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: antigen 11

<400> SEQUENCE: 27

Gly Cys Thr Thr Tyr Lys Trp Glu Thr Phe Leu Thr Ser Glu Leu
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: antigen 12

<400> SEQUENCE: 28

Thr Tyr Lys Trp Glu Thr Phe Leu Thr Thr Glu Leu
1               5                   10

<210> SEQ ID NO 29
<211> LENGTH: 15
<212> TYPE: PRT
```

```
<213> ORGANISM: Artificial Sequence
<220> FEATURE:
<223> OTHER INFORMATION: antigen 13

<400> SEQUENCE: 29

Leu Thr Ser Glu Leu Pro Gln Trp Leu Ser Ala Asn Arg Ala Val
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: antigen 14

<400> SEQUENCE: 30

Leu Thr Ser Glu Leu Pro Gln Trp Leu Ser Ala Asn Arg Ala Val
1               5                   10                  15

<210> SEQ ID NO 31
<211> LENGTH: 12
<212> TYPE: PRT
<213> ORGANISM: Artificial Sequence
<220> FEATURE:
<223> OTHER INFORMATION: antigen 15

<400> SEQUENCE: 31

Leu Ser Ser Glu Leu Pro Asp Trp Leu Ala Ala Asn
1               5                   10

<210> SEQ ID NO 32
<211> LENGTH: 15
<212> TYPE: PRT
<213> ORGANISM: Artificial Sequence
<220> FEATURE:
<223> OTHER INFORMATION: antigen 16

<400> SEQUENCE: 32

Leu Thr Ser Glu Leu Pro Gln Tyr Leu Ala Ser Asn Lys Ser Val
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: antigen 17

<400> SEQUENCE: 33

Leu Thr Ser Glu Leu Pro Gln Trp Leu Ser Ala Asn Arg Ser Val
1               5                   10                  15

<210> SEQ ID NO 34
<211> LENGTH: 12
<212> TYPE: PRT
<213> ORGANISM: Artificial Sequence
<220> FEATURE:
<223> OTHER INFORMATION: antigen 18

<400> SEQUENCE: 34

Leu Thr Thr Glu Leu Pro Gln Trp Leu Gly Ala Asn
1               5                   10

<210> SEQ ID NO 35
<211> LENGTH: 15
<212> TYPE: PRT
<213> ORGANISM: Artificial Sequence
```

```
<220> FEATURE:
<223> OTHER INFORMATION: antigen 19

<400> SEQUENCE: 35

Gln Gln Phe Ile Tyr Ala Gly Ser Leu Ser Ala Leu Leu Asp Pro
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: antigen 20

<400> SEQUENCE: 36

Gln Gln Phe Ile Tyr Ala Gly Ser Leu Ser Ala Leu Leu Asp Pro
1               5                   10                  15

<210> SEQ ID NO 37
<211> LENGTH: 14
<212> TYPE: PRT
<213> ORGANISM: Artificial Sequence
<220> FEATURE:
<223> OTHER INFORMATION: antigen 21

<400> SEQUENCE: 37

Gln Phe Ile Tyr Ala Gly Ser Leu Ser Ala Leu Leu Asp Pro
1               5                   10

<210> SEQ ID NO 38
<211> LENGTH: 14
<212> TYPE: PRT
<213> ORGANISM: Artificial Sequence
<220> FEATURE:
<223> OTHER INFORMATION: antigen 22

<400> SEQUENCE: 38

Gln Phe Val Tyr Ala Gly Ser Leu Ser Ala Leu Leu Asp Pro
1               5                   10

<210> SEQ ID NO 39
<211> LENGTH: 15
<212> TYPE: PRT
<213> ORGANISM: Artificial Sequence
<220> FEATURE:
<223> OTHER INFORMATION: antigen 23

<400> SEQUENCE: 39

Gln Gln Phe Ile Tyr Ala Gly Ser Leu Ser Ala Leu Met Asp Pro
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: antigen 25

<400> SEQUENCE: 40

Gln Gln Phe Ile Tyr Ala Gly Ala Leu Ser Gly Phe Leu His Pro
1               5                   10                  15

<210> SEQ ID NO 41
<211> LENGTH: 15
<212> TYPE: PRT
<213> ORGANISM: Artificial Sequence
<220> FEATURE:
```

<223> OTHER INFORMATION: antigen 25

<400> SEQUENCE: 41

Glu Ile Ser Thr Asn Ile Arg Gln Ala Gly Val Gln Tyr Ser Arg
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: antigen 26

<400> SEQUENCE: 42

Glu Ile Ser Thr Ile Asn Arg Gln Ala Gly Val Gln Tyr Ser Arg
1               5                   10                  15

<210> SEQ ID NO 43
<211> LENGTH: 8
<212> TYPE: PRT
<213> ORGANISM: Artificial Sequence
<220> FEATURE:
<223> OTHER INFORMATION: antigen 27

<400> SEQUENCE: 43

Glu Ile Ser Thr Glu Ile Arg Gln
1               5

<210> SEQ ID NO 44
<211> LENGTH: 9
<212> TYPE: PRT
<213> ORGANISM: Artificial Sequence
<220> FEATURE:
<223> OTHER INFORMATION: antigen 28

<400> SEQUENCE: 44

Glu Ile Ser Thr Glu Ile Arg Gln Ala
1               5

<210> SEQ ID NO 45
<211> LENGTH: 14
<212> TYPE: PRT
<213> ORGANISM: Artificial Sequence
<220> FEATURE:
<223> OTHER INFORMATION: antigen 29

<400> SEQUENCE: 45

Glu Ile Ser Thr Asn Ile Arg Gln Ala Gly Val Gln Tyr Ser
1               5                   10

<210> SEQ ID NO 46
<211> LENGTH: 12
<212> TYPE: PRT
<213> ORGANISM: Artificial Sequence
<220> FEATURE:
<223> OTHER INFORMATION: antigen 30

<400> SEQUENCE: 46

Ile Ser Gln Asn Ile Arg Glu Ser Gly Leu Gln Tyr
1               5                   10

<210> SEQ ID NO 47
<211> LENGTH: 15
<212> TYPE: PRT
<213> ORGANISM: Artificial Sequence
<220> FEATURE:
<223> OTHER INFORMATION: antigen 37

<400> SEQUENCE: 47

Val Gln Tyr Ser Arg Ala Asp Glu Glu Gln Gln Gln Ala Leu Ser
1               5                   10                  15

<210> SEQ ID NO 48
<211> LENGTH: 17
<212> TYPE: PRT
<213> ORGANISM: Artificial Sequence
<220> FEATURE:
<223> OTHER INFORMATION: antigen 38

<400> SEQUENCE: 48

Tyr Ala Arg Glu Leu Thr Asp Asp Glu Arg Ala Gln Gln Gln Lys Ala
1               5                   10                  15

Leu

<210> SEQ ID NO 49
<211> LENGTH: 17
<212> TYPE: PRT
<213> ORGANISM: Artificial Sequence
<220> FEATURE:
<223> OTHER INFORMATION: antigen 39

<400> SEQUENCE: 49

Tyr Ala Arg Glu Leu Thr Asp Glu Glu Arg Ala Gln Gln Gln Gln Ala
1               5                   10                  15

Leu

<210> SEQ ID NO 50
<211> LENGTH: 17
<212> TYPE: PRT
<213> ORGANISM: Artificial Sequence
<220> FEATURE:
<223> OTHER INFORMATION: antigen 40

<400> SEQUENCE: 50

Tyr Ala Arg Glu Leu Thr Asp Glu Glu Arg Ala Gln Gln Gln Gln Ala
1               5                   10                  15

Leu

<210> SEQ ID NO 51
<211> LENGTH: 15
<212> TYPE: PRT
<213> ORGANISM: Artificial Sequence
<220> FEATURE:
<223> OTHER INFORMATION: antigen 41

<400> SEQUENCE: 51

Val Gln Tyr Ser Lys Ala Asp Glu Glu Gln Gln Gln Ala Leu Ser
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: antigen 42

<400> SEQUENCE: 52

Tyr Ala Arg Glu Leu Thr Asp Glu Glu Arg Gln Lys Gln Gln Gln Ala
1               5                   10                  15

Leu

```
<210> SEQ ID NO 53
<211> LENGTH: 15
<212> TYPE: PRT
<213> ORGANISM: Artificial Sequence
<220> FEATURE:
<223> OTHER INFORMATION: antigen 31

<400> SEQUENCE: 53

Ala Asp Glu Glu Gln Gln Gln Ala Leu Ser Ser Gln Met Gly Phe
1               5                   10                  15

<210> SEQ ID NO 54
<211> LENGTH: 7
<212> TYPE: PRT
<213> ORGANISM: Artificial Sequence
<220> FEATURE:
<223> OTHER INFORMATION: antigen 32

<400> SEQUENCE: 54

Gln Ala Leu Ser Ala Gln Met
1               5

<210> SEQ ID NO 55
<211> LENGTH: 12
<212> TYPE: PRT
<213> ORGANISM: Artificial Sequence
<220> FEATURE:
<223> OTHER INFORMATION: antigen 33

<400> SEQUENCE: 55

Ala Asn Glu Glu Gln Gln Gln Ser Trp Ala Thr Gln
1               5                   10

<210> SEQ ID NO 56
<211> LENGTH: 11
<212> TYPE: PRT
<213> ORGANISM: Artificial Sequence
<220> FEATURE:
<223> OTHER INFORMATION: antigen 34

<400> SEQUENCE: 56

Asp Glu Glu Arg Ala Gln Gln Gln Gln Ala Leu
1               5                   10

<210> SEQ ID NO 57
<211> LENGTH: 11
<212> TYPE: PRT
<213> ORGANISM: Artificial Sequence
<220> FEATURE:
<223> OTHER INFORMATION: antigen 35

<400> SEQUENCE: 57

Gln Gln Gln Ala Leu Ala Asp Gln Leu Gly Phe
1               5                   10

<210> SEQ ID NO 58
<211> LENGTH: 10
<212> TYPE: PRT
<213> ORGANISM: Artificial Sequence
<220> FEATURE:
<223> OTHER INFORMATION: antigen 36

<400> SEQUENCE: 58

Ala Asp Glu Glu Gln Leu Arg Ala Leu Ser
1               5                   10
```

```
<210> SEQ ID NO 59
<211> LENGTH: 15
<212> TYPE: PRT
<213> ORGANISM: Artificial Sequence
<220> FEATURE:
<223> OTHER INFORMATION: antigen 43

<400> SEQUENCE: 59

Asp Ile Lys Val Gln Phe Gln Ser Gly Gly Asn Asn Ser Pro Ala
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: antigen 44

<400> SEQUENCE: 60

Leu Thr Ser Glu Leu Pro Gln Trp Leu Ser Ala Asn Arg Ala Val
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: antigen 45

<400> SEQUENCE: 61

Gln Gln Phe Ile Tyr Ala Gly Ser Leu Ser Ala Leu Leu Asp Pro
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: antigen 46

<400> SEQUENCE: 62

Glu Ile Ser Thr Asn Ile Arg Gln Ala Gly Val Gln Tyr Ser Arg
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: antigen 47

<400> SEQUENCE: 63

Val Gln Tyr Ser Arg Ala Asp Glu Glu Gln Gln Gln Ala Leu Ser
1               5                   10                  15
```

MYCOBACTERIAL ANTIGEN COMPOSITIONS AND METHODS OF USE

CROSS REFERENCE TO RELATED APPLICATIONS

This application is a National Stage application filed under 35 U.S.C. § 371 of International Application No. PCT/US2019/029505, filed on Apr. 26, 2019, which claims the benefit of U.S. provisional Application No. 62/663,239, filed Apr. 26, 2018. The content of each of the aforementioned applications is hereby incorporated by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 37921_0008U2_SL. The size of the text file is 36 KB and the text file was created on Oct. 26, 2020.

FIELD OF INVENTION

The present invention relates generally to novel immunogenic combinations comprising mycobacterial polynucleotides and polypeptides, to fragments or variants thereof, and to cells comprising such combined antigens, where the antigens are from a *Mycobacterium* species.

BACKGROUND

Mycobacteria are ubiquitous pathogens which are a cause of potentially serious opportunistic infections in immunocompromised patients. Treatment of mycobacterial infections is complicated by broad antimicrobial resistance, which often requires antibiotic courses with multiple agents.

There is evidence that T-cell immunity to mycobacteria is critical in controlling and preventing mycobacterial infections, as T-cell deficiency imparts high risk of invasive mycobacterial infection.

In view of the increasing threat and global prevalence of mycobacterial infection, new strategies are required for more effective prevention, treatment, and diagnosis of mycobacterial infection.

SUMMARY OF THE DISCLOSURE

The disclosure relates, at least in part, to compositions comprising mycobacterial polynucleotides and polypeptides, or fragments or variants thereof, and exposing such compositions to cells, such as T cells. The disclosure also relates, at least in part, to compositions comprising polynucleotides expressing mycobacterial polypeptides and/or polypeptides mycobacterial, or fragments or variants thereof, and exposing such compositions to cells, such as T cells. The disclosure also relates to cells comprising polynucleotides expressing mycobacterial polypeptides and/or mycobacterial polypeptides, or fragments or variants thereof, and methods of priming cells comprising exposing the polynucleotides and/or polypeptides to the cells for a time period sufficient for: (i) the polynucleotides to express the polypeptides and stimulate an antigen-specific immune response against the polypeptides encoded by the polynucleotides within the cell or cells; and/or (ii) stimulate an antigen-specific immune response against the polypeptide. In some embodiments, the disclosure relates to expanding T-cells ex vivo, and to methods of use thereof. In some embodiments, the T cells are naïve T cells. In some embodiments, the T cells are naïve T cells from a subject that has not been exposed to mycobacteria. In some embodiments, T cells are naïve T cells from a subject that has not contracted a mycobacterial infection. In some embodiments, T cells are naïve T cells from a subject that has not contracted a mycobacterial infection from one or a plurality of *Mycobacterium* species disclosed herein. In some embodiments, T cells are naïve T cells from a subject that has not contracted a mycobacterial infection. In some embodiments, the T cells are naïve T cells isolated from a subject. The disclosure is also based, in part, on the surprising finding that human T-cells from healthy donors may be expanded using a rapid ex vivo expansion protocol using overlapping synthetic peptide pools encompassing various Mycobacterial antigens, and in particular embodiments, antigens Ag85B, PPe68, P9WNK7, ESXA, ESXB and ADK.

In one aspect, the disclosure features a composition comprising a nucleic acid sequence encoding an Ag85B antigen, or a functional fragment thereof, from a *Mycobacterium* species, a nucleic acid encoding a PPE68 antigen, or a functional fragment thereof, from a *Mycobacterium* species, a nucleic acid encoding a ESXA antigen, or a functional fragment thereof, from a *Mycobacterium* species, a nucleic acid encoding an ESXB antigen, or a functional fragment thereof, from a *Mycobacterium* species, a nucleic acid encoding an ADK antigen, or a functional fragment thereof, from a *Mycobacterium* species, or a combination thereof. In some embodiments, the nucleic acid sequence encoding an Ag85B antigen, or a functional fragment thereof, is at least 50% identical to SEQ ID NO. 1. In some embodiments, the nucleic acid sequence encoding an Ag85B antigen, or a functional fragment thereof, is at least about 50%, 55%, 60%, 65%, 70%, 75%, 80%, 85%, 90%, 95%, 96%, 97%, 98%, 99% identical to SEQ ID NO. 1. In some embodiments, the nucleic acid sequence encoding a PPE68 antigen, or a functional fragment thereof, is at least 50% identical to SEQ ID NO. 2. In some embodiments, the nucleic acid sequence encoding a PPE68 antigen, or a functional fragment thereof, is at least about 50%, 55%, 60%, 65%, 70%, 75%, 80%, 85%, 90%, 95%, 96%, 97%, 98%, 99% identical to SEQ ID NO. 2. In some embodiments, the nucleic acid sequence encoding an ESXA antigen, or a functional fragment thereof, is at least 50% identical to SEQ ID NO. 3. In some embodiments, the nucleic acid sequence encoding a ESXA antigen, or a functional fragment thereof, is at least about 50%, 55%, 60%, 65%, 70%, 75%, 80%, 85%, 90%, 95%, 96%, 97%, 98%, 99% identical to SEQ ID NO. 3. In some embodiments, the nucleic acid sequence encoding an ESXB antigen, or a functional fragment thereof, is at least 50% identical to SEQ ID NO. 4. In some embodiments, the nucleic acid sequence encoding an ESXB antigen, or a functional fragment thereof, is at least about 50%, 55%, 60%, 65%, 70%, 75%, 80%, 85%, 90%, 95%, 96%, 97%, 98%, 99% identical to SEQ ID NO. 4. In some embodiments, the nucleic acid sequence encoding an ADK antigen, or a functional fragment thereof, is at least 50% identical to SEQ ID NO. 5. In some embodiments, the nucleic acid sequence encoding an ADK antigen, or a functional fragment thereof, is at least about 50%, 55%, 60%, 65%, 70%, 75%, 80%, 85%, 90%, 95%, 96%, 97%, 98%, 99% identical to SEQ ID NO. 5.

In other aspects, the disclosure features a composition comprising a polypeptide comprising an amino acid sequence, or fragment thereof, coding for an Ag85B antigen from a *Mycobacterium* species, a polypeptide comprising an amino acid sequence, or fragment thereof, coding for a PPE68 antigen from a *Mycobacterium* species, a polypeptide comprising an amino acid sequence, or fragment thereof, coding for a ESXA antigen from a *Mycobacterium* species, a polypeptide comprising an amino acid sequence, or fragment thereof, coding for a ESXB antigen from a *Mycobacterium* species, a polypeptide comprising an amino acid sequence, or fragment thereof, coding for an ADK antigen from a *Mycobacterium* species, or a combination thereof. In some embodiments, the polypeptide comprising an amino acid sequence, or fragment thereof, coding for an Ag85B antigen is about 50% identical to SEQ ID NO. 6. In some embodiments, the polypeptide comprising an amino acid sequence, or fragment thereof, coding for an Ag85B antigen is about 50%, 55%, 60%, 65%, 70%, 75%, 80%, 85%, 90%, 95%, 96%, 97%, 98%, 99% identical to SEQ ID NO. 6. In some embodiments, the polypeptide comprising an amino acid sequence, or fragment thereof, coding for an PPE68 antigen is 50% identical to SEQ IS NO. 7. In some embodiments, the polypeptide comprising an amino acid sequence, or fragment thereof, coding for an PPE68 antigen is about 50%, 55%, 60%, 65%, 70%, 75%, 80%, 85%, 90%, 95%, 96%, 97%, 98%, 99% identical to SEQ IS NO. 7. In some embodiments, the polypeptide comprising an amino acid sequence, or fragment thereof, coding for an ESXA antigen is 50% identical to SEQ ID NO. 8. In some embodiments, the polypeptide comprising an amino acid sequence, or fragment thereof, coding for an ESXA antigen is about 50%, 55%, 60%, 65%, 70%, 75%, 80%, 85%, 90%, 95%, 96%, 97%, 98%, 99% identical to SEQ ID NO. 8. In some embodiments, the polypeptide comprising an amino acid sequence, or fragment thereof, coding for an ESXB antigen is 50% identical to SEQ ID NO. 9. In some embodiments, the polypeptide comprising an amino acid sequence, or fragment thereof, coding for an ESXB antigen is about 50%, 55%, 60%, 65%, 70%, 75%, 80%, 85%, 90%, 95%, 96%, 97%, 98%, 99% identical to SEQ ID NO. 9. In some embodiments, the polypeptide comprising an amino acid sequence, or fragment thereof, coding for an ADK antigen is about 50% identical to SEQ ID NO. 10. In some embodiments, the polypeptide comprising an amino acid sequence, or fragment thereof, coding for an ADK antigen is about 50%, 55%, 60%, 65%, 70%, 75%, 80%, 85%, 90%, 95%, 96%, 97%, 98%, 99% identical to SEQ ID NO. 10. In another embodiment, one or more amino acid sequences overlap in sequence to span part or all of the Ag85B, PPE68, ESXA, ESXB and ADK antigens. In some embodiments of any of the above aspects or embodiments, the *Mycobacterium* species is selected from the group consisting of *M. tuberculosis, M. bovis, M. bovis* BCG, *M. avium, M. abscessus, M. chelonae, M. kansasii, M. africanum, M. canetti, M. caprae, M. microt, M. mungi, M. orygis, M. avium, M. avium paratuberculosis, M. avium silvaticum, M. columbiense, M. intracellulare, M. gordonae, M. ulcerans, M. genavense, M. scrofulaceum, M. intermedium, M. fortuitum*, and *M. mucogenicum*. In another embodiment of any of the above aspects or embodiments, the composition is used to stimulate an immune cell. In some embodiments, stimulating the immune cell comprises activating the immune cell. In some embodiments, stimulating the immune cell comprises expanding the immune cell. In some embodiments, the immune cell is a CD8+ T cell. In some embodiments, the immune cell is a NK cell. In some embodiments, the immune cell is a CD4+ T cell.

In other aspects, the disclosure features a cell or plurality of cells comprising one or a combination of (i) a nucleic acid sequence encoding an Ag85B antigen at least about 50% identical to SEQ ID NO. 1, a nucleic acid sequence encoding a PPE68 antigen at least about 50% identical to SEQ ID NO. 2, a nucleic acid sequence encoding a ESXA antigen at least about 50% identical to SEQ ID NO. 3, a nucleic acid sequence encoding an ESXB antigen at least about 50% identical to SEQ ID NO. 4, a nucleic acid sequence encoding an ADK antigen at least about 50% identical to SEQ ID NO. 5, or a combination thereof; (ii) a polypeptide comprising an amino acid sequence coding for an Ag85B antigen at least about 50% identical to SEQ ID NO. 6, a polypeptide comprising an amino acid sequence coding for an PPE68 antigen at least about 50% identical to SEQ ID NO. 7, a polypeptide comprising an amino acid sequence coding for an ESXA antigen at least about 50% identical to SEQ ID NO. 8, a polypeptide comprising an amino acid sequence coding for an ESXB antigen at least about 50% identical to SEQ ID NO. 9, a polypeptide comprising an amino acid sequence coding for an ADK antigen at least about 50% identical to SEQ ID NO. 10, or a combination thereof; (iii) a nucleic acid of (i), encoding a functional fragment of a nucleic acid sequence of SEQ ID NO. 1, SEQ ID NO. 2, SEQ ID NO. 3, SEQ ID NO. 4 or SEQ ID NO. 5; and (iv) an amino acid sequence of (ii), encoding a functional fragment of an amino acid sequence of SEQ ID NO. 6, SEQ ID NO. 7, SEQ ID NO. 8, SEQ ID NO. 9 or SEQ ID NO. 10. In some embodiments, the cell is a helper (CD4+) T-cell. In some embodiments, the cell is a cytotoxic (CD8+) T-cell. In some embodiments, the cell is a Gamma/Delta T-cell. In some embodiments, the cell is a central memory T-cell. In some embodiments, the cell is an effector memory T-cell. In some embodiments, the CD4+ T cell comprises about 60% to about 90% of the total T-cell population. In some embodiments, the CD8+ T-cell comprises about 0% to about 40% of the total T-cell population. In some embodiments, the Gamma/Delta T-cell comprises about 0.5% to about 10% of the total T-cell population. In some embodiments, the central memory T-cell comprises about 0.5% to about 15% of the total T-cell population. In some embodiments, the central memory T-cell comprises about 20% to about 60% of the total T-cell population. In some embodiments, the plurality of cells comprise CD4+ T-cells and CD8+ T-cells, wherein the number of CD8+ T-cells is greater than the number of CD4+ T-cells. In another embodiment, the cell is from a human subject. In a further embodiment, the human subject is immunocompromised. In another further embodiment, the human subject has been diagnosed or is suspected of having a Mycobacterial infection. In some embodiments, the cell or plurality of cells are expanded in cell culture. In some embodiments, the cell or plurality of cells comprises at least one primary T-cell. In some embodiments, the cell is an antigen presenting cell (APC). In another embodiment, the APC cell is an artificial antigen presenting cell. In some embodiments, the cell is a macrophage. In some embodiments, the cell is a dendritic cell. In some embodiments of any of the above aspects or embodiments, the composition further comprises one or more antigens from a Mycobacterial species, wherein the one or more antigens are provided in Table 1.

In another embodiment of any of the above aspects or embodiments, the cell is capable of expressing a polypeptide comprising an amino acid sequence, or fragment thereof, coding for an Ag85B antigen from a *Mycobacterium* species, a polypeptide comprising an amino acid sequence, or fragment thereof, coding for a PPE68 antigen from a *Mycobacterium* species, a polypeptide comprising an amino acid sequence, or fragment thereof, coding for a ESXA antigen from a *Mycobacterium* species, a polypeptide comprising an amino acid sequence, or fragment thereof, coding for a ESXB antigen from a *Mycobacterium* species, a polypeptide comprising an amino acid sequence, or fragment thereof, coding for an ADK antigen from a *Mycobacterium* species, or a combination thereof.

In other aspects, the disclosure features a cell engineered to expand T-cells ex vivo, wherein the cell comprises at least 5 antigens selected from Ag85B, PPE68, ESXA, ESXB and ADK, wherein the cell is produced by a process comprising introducing one or more nucleic acids, each encoding one or more of the at least 5 antigens, into the cell; and culturing the cell under conditions suitable for production of one or more of the antigens. In some embodiments, the cell is an antigen-presenting cell, including T-cell, B-cells, monocytes, dendritic cells, Phytohemagglutinin blasts, or artificial antigen presenting cells based on immortalized cells such as K562 or other cell lines. In some embodiments, the nucleic acid comprises DNA or RNA. In some embodiments, the introducing step comprises viral transduction. In some embodiments, the introducing step comprises electroporation. In another embodiment, the disclosure features a composition comprising one or a plurality of cells of any of the aspects or embodiments herein.

In other aspects, the disclosure features a pharmaceutical composition comprising (i) a pharmaceutically effective amount of the composition of any of the aspects and embodiments herein: and (ii) a pharmaceutically acceptable carrier. In other aspects, the disclosure features a pharmaceutical composition comprising (i) a pharmaceutically effective amount of the composition of any of the aspects and embodiments herein; and (ii) a pharmaceutically acceptable carrier for treatment of mycobacterial infection in a subject in need thereof. In other aspects, the disclosure features a pharmaceutical composition comprising (i) a pharmaceutically effective amount of the composition of any of the aspects and embodiments herein; and (ii) a pharmaceutically acceptable carrier, for treatment or prevention of a mycobacterial infection in a subject. In some embodiments, the subject is immunocompromised. In some embodiments, the subject has or is identified as having an organ transplant. In some embodiments, the subject is immunocompromised. In some embodiments, the subject has or is identified as having a cancer. In some embodiments, the subject is immunocompromised. In some embodiments, the subject has or is identified as having a cancer of the blood.

In other aspects, the disclosure features a pharmaceutical composition comprising (i) a pharmaceutically effective amount of one or a plurality of cells of any of the aspects and embodiments here; and (ii) a pharmaceutically acceptable carrier.

In other aspects, the disclosure features a method of expanding T cells ex vivo, the method comprising (a) culturing one or a plurality of T-cells; (b) contacting the plurality of T-cells with a polypeptide comprising an amino acid sequence, or fragment thereof, coding for an Ag85B antigen from a *Mycobacterium* species, a polypeptide comprising an amino acid sequence, or fragment thereof, coding for a PPE68 antigen from a *Mycobacterium* species, a polypeptide comprising an amino acid sequence, or fragment thereof, coding for a ESXA antigen from a *Mycobacterium* species, a polypeptide comprising an amino acid sequence, or fragment thereof, coding for a ESXB antigen from a *Mycobacterium* species, a polypeptide comprising an amino acid sequence, or fragment thereof, coding for an ADK antigen from a *Mycobacterium* species, or a combination thereof; or contacting the plurality of T-cells with a composition of any of the aspects or embodiments herein or the pharmaceutical composition of any of the aspects or embodiments herein.

In other aspects, the disclosure features a method for expanding T-cells ex vivo, the method comprising (a) culturing one or a plurality of isolated T-cells; (b) contacting the plurality of T-cells with an antigen presenting cell, wherein the antigen presenting cell presents expressing an amino acid sequence, or fragment thereof, coding for an Ag85B antigen from a *Mycobacterium* species, a polypeptide comprising an amino acid sequence, or fragment thereof, coding for a PPE68 antigen from a *Mycobacterium* species, a polypeptide comprising an amino acid sequence, or fragment thereof, coding for a ESXA antigen from a *Mycobacterium* species, a polypeptide comprising an amino acid sequence, or fragment thereof, coding for a ESXB antigen from a *Mycobacterium* species, a polypeptide comprising an amino acid sequence, or fragment thereof, coding for an ADK antigen from a *Mycobacterium* species, or a combination thereof. In some embodiments, the method further comprises stimulating the one or plurality of T-cells with one or more cytokines. In some embodiments, the cytokine is selected from the group consisting of IL-4, IL-7, IL-15, IL-21, TNFβ, and IFNα. In some embodiments, the method further comprises isolating a sample from a subject prior to step (a) and isolating T-cell from the samples.

In other aspects, the disclosure features a method of treating *Mycobacterium* infection in a subject in need thereof, the method comprising administering to the subject a therapeutically effective amount of the composition of any of the aspects or embodiments herein, or the pharmaceutical composition of any of the aspects or embodiments herein. In some embodiments, the subject is an immunocompromised host. In some embodiments, the subject has been diagnosed as having, or suspected of having, infection with a *Mycobacterium* species. In some embodiments, the infection is an active infection.

In other aspects, the disclosure features a method of preventing or delaying infection with a *Mycobacterium* in a subject in need thereof, the method comprising administering to the subject a therapeutically effective amount of the composition of any of the aspects or embodiments herein, or the pharmaceutical composition of any of the aspects or embodiments herein. In some embodiments of any of the above aspects or embodiments, the *Mycobacterium* species is selected from the group consisting of *M. tuberculosis, M. bovis, M bovis BCG, M. avium, M. abscessus, M. chelonae, M. kansasii, M. africanum, M. canetti, M. caprae, M. microt, M. mungi, M. orygis, M. avium, M. avium paratuberculosis, M. avium silvaticum, M. columbiense, M. intracellulare, M. gordonae, M. ulcerans, M. genavense, M. scrofulaceum, M. intermedium, M. fortuitum*, and *M. mucogenicum*. In some embodiments of any of the above aspects or embodiments, the subject is immunocompromised. In some embodiments of any of the above aspects or embodiments, the subject is a child under the age of 21. In some embodiments of any of the above aspects or embodiments, the subject is a child under the age of 12.

BRIEF DESCRIPTION OF DRAWINGS

FIG. 11 provides an analysis of identified T cell epitopes from AG85B showed moderate to high conservation across mycobacterial species. Peptide 7 table begins from top to bottom SEQ ID NO: 17, 18, 19, 20, 21 and 22. Peptide 14 table from top to bottom is SEQ ID NO: 23, 24, 25, 26, 27, 28. Peptide 15 Table begins from top to bottom as SEQ ID NO:29, 30, 31, 32, 33, 34. Peptide 19 table begins from top to bottom SEQ ID NO:35, 36, 37, 38, 39, 40.

FIG. 12 provides an analysis of identified T cell epitopes from ESXB showed low to moderate conservation across mycobacterial species. Peptide 8 table begins from top to bottom SEQ ID NO: 41, 42, 43, 44, 45, 46. Peptide 9 table from top to bottom is SEQ ID NO: 47, 48, 49, 50, 51, 52. Peptide 10 Table begins from top to bottom as SEQ ID NO:53, 54, 55, 56, 57, 58.

DETAILED DESCRIPTION OF EMBODIMENTS

Figure 1:
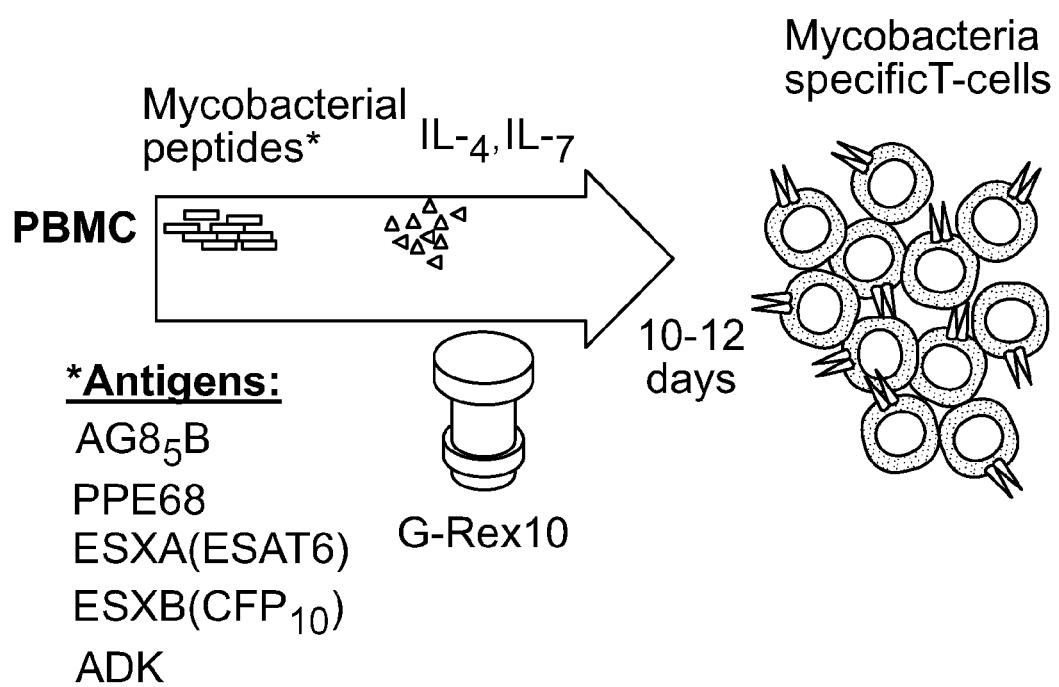
FIG. 1 depicts a manufacturing schema of ex vivo expansion of mycobacteria-specific T cells. Peripheral blood mononuclear cells (PBMCs) are stimulated with overlapping peptide pools encompassing listed mycobacterial antigens and cultured in a G-Rex-10 bioreactor with cytokines for 10-12 days.

Before the present compositions and methods are described, it is to be understood that this disclosure is not limited to the particular molecules, compositions, methodologies or protocols described, as these may vary. It is also to be understood that the terminology used in the description is for the purpose of describing the particular versions or embodiments only, and is not intended to limit the scope of the present disclosure which will be limited only by the appended claims. It is understood that these embodiments are not limited to the particular methodology, protocols, cell lines, vectors, and reagents described, as these may vary. It also is to be understood that the terminology used herein is for the purpose of describing particular embodiments only, and is not intended to limit the scope of the present embodiments or claims. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

Definitions

Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred methods, devices, and materials are now described. All publications mentioned herein are incorporated by reference. Nothing herein is to be construed as an admission that the disclosure is not entitled to antedate such disclosure by virtue of prior disclosure.

As used in the specification and the appended claims, the singular forms "a," "an" and "the" include plural referents unless the context clearly dictates otherwise.

The term "about" as used herein when referring to a measurable value such as an amount, a temporal duration, and the like, is meant to encompass variations of 20%, ±10%, ±5%, ±1%, ±0.9%, ±0.8%, ±0.7%, ±0.6%, ±0.5%, 0.4%, ±0.3%, 0.2% or 0.1% from the specified value, as such variations are appropriate to perform the disclosed methods.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, In some embodiments, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

As used herein, the phrase "integer from X to Y" means any integer that includes the endpoints. That is, where a range is disclosed, each integer in the range including the endpoints is disclosed. For example, the phrase "integer from X to Y" discloses 1, 2, 3, 4, or 5 as well as the range 1 to 5.

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. Thus, a polypeptide "comprises" an amino acid sequence when the amino acid sequence might be part of the final amino acid sequence of the polypeptide. Such a polypeptide can have up to several hundred additional amino acids residues (e.g. tag and targeting peptides as mentioned herein). "Consisting essentially of" means excluding other components or steps of any essential significance. Thus, a composition consisting essentially of the recited components would not exclude trace contaminants and pharmaceutically acceptable carriers. A polypeptide "consists essentially of an amino acid sequence when such an amino acid sequence is present with eventually only a few additional amino acid residues. "Consisting of means excluding more than trace elements of other components or steps. For example, a polypeptide "consists of an amino acid sequence when the polypeptide does not contain any amino acids but the recited amino acid sequence.

As used herein, "substantially equal" means within a range known to be correlated to an abnormal or normal range at a given measured metric. For example, if a control sample is from a diseased patient, substantially equal is within an abnormal range. If a control sample is from a patient known not to have the condition being tested, substantially equal is within a normal range for that given metric.

As used herein, the term "subject," "individual" or "patient," used interchangeably, means any animal, including mammals, such as mice, rats, other rodents, rabbits, dogs, cats, swine, cattle, sheep, horses, or primates, such as humans. In some embodiments, the subject or patient is a human child of no more than about 20 years of age. In some embodiments, the subject or patient is a human child of no more than about 18, 17, 16, 15, 14, 13, 12, 11, 10, 9, 8, 7, 6, 5, 4, 3, 2, or 1 year of age. In some embodiments, the subject has been diagnosed with or has a cancer. In some embodiments, the subject has undergone an organ transplant, such as a bone marrow transplant. In some embodiments, the subject is a T cell donor if the embodiment relates to a method of isolating one or a plurality of cells from a donor for stimulation or priming of the T cell.

The term "subject" is used throughout the specification to describe an animal from which a cell sample is taken. In some embodiments, the subject is a human. For diagnosis of those conditions which are specific for a specific subject, such as a human being, the term "patient" may be interchangeably used. In some instances in the description of the present invention, the term "patient" will refer to human patients suffering from a particular disease or disorder. In some embodiments, the subject may be a human suspected of having or being identified as at risk to develop an infection with a *Mycobacterium*. In some embodiments, the subject may be diagnosed as having an infection with a *Mycobacterium* and of having or being identified as at risk to develop an infection with a *Mycobacterium*.

As used herein, an "immunocompromised subject" is meant to refer to a subject with a congenital or acquired defect in adaptive or innate immunity, including but not limited to primary immunodeficiency disorders, patients undergoing chemotherapy or immunosuppressive therapy, or patients undergoing hematopoietic stem cell transplantation. In some embodiments, the subject is an immunocompromised adult or child.

As used herein, the term "animal" includes, but is not limited to, humans and non-human vertebrates such as wild animals, rodents, such as rats, ferrets, and domesticated animals, and farm animals, such as dogs, cats, horses, pigs, cows, sheep, and goats. In some embodiments, the animal is a mammal. In some embodiments, the animal is a human. In some embodiments, the animal is a non-human mammal.

As used herein, the term "mammal" means any animal in the class Mammalia such as rodent (i.e., a mouse, a rat, or a guinea pig), a monkey, a cat, a dog, a cow, a horse, a pig, or a human. In some embodiments, the mammal is a human. In some embodiments, the mammal refers to any non-human mammal. The present disclosure relates to any of the methods or compositions of matter disclosed herein wherein the sample is taken from a mammal or non-human mammal. The present disclosure relates to any of the methods or compositions of matter disclosed herein wherein the sample is taken from a human or non-human primate.

As used herein, the phrase "in need thereof" means that the animal or mammal has been identified or suspected as having a need for the particular method or treatment. In some embodiments, the identification can be by any means of diagnosis or observation. In any of the methods and treatments described herein, the animal or mammal can be in need thereof. In some embodiments, the animal or mammal is in an environment or will be traveling to an environment in which a particular disorder or condition is prevalent or more likely to occur.

As used herein, "*Mycobacterium* infection" refers to the exposure of a subject to a *Mycobacterium* species followed by a colonization of the subject or the subject's tissue(s) by the bacterium. The colonization can cause serious diseases (e.g. tuberculosis, leprosy, Bureli ulcer etc, depending on the *Mycobacterium*), or can result in no adverse signs (asymptomatic or latent infection).

As used herein, "cell culture" means growth, maintenance, transfection, transduction and/or propagation of cells, tissues, or their products. As used herein, "culture medium" refers to any solution capable of sustaining the growth of the targeted cells either in vitro or in vivo, or any solution with which targeted cells or exogenous nucleic acids are mixed before being applied to cells in vitro or to a patient in vivo.

As used herein, the terms "heterologous" and "foreign" with reference to nucleic acids, such as DNA and RNA, are used interchangeably and refer to nucleic acid that does not occur naturally as part of a genome or cell in which it is present or which is found in a location(s) and/or in amounts in a genome or cell that differ from the location(s) and/or amounts in which it occurs in nature, i.e., nucleic acid that is not endogenous to the cell and has been exogenously introduced into the cell. Examples of heterologous DNA include, but are not limited to, DNA that encodes a gene product or gene product(s) of interest introduced into cells, for example, for production of an encoded protein.

As used herein, "delivery" refers to the process by which exogenous nucleic acid molecules are transferred into a cell such that they are located inside the cell. Delivery of nucleic acids is a distinct process from expression of nucleic acids. Nucleic acid material can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "expression" refers to the process by which nucleic acid is translated into peptides or is transcribed into mRNA and translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including: calcium phosphate DNA co-precipitation (Methods in Molecular Biology (1991)); DEAE-dextran (supra); electroporation (supra); cationic liposome-mediated transfection (supra); and tungsten particle-facilitated microparticle bombardment (Johnston (1990)). Strontium phosphate DNA co-precipitation (Brash et al. (1987)) is also a transfection method.

In contrast, "transduction of cells" refers to the process of transferring nucleic acid into a cell using a DNA or RNA virus. A RNA virus (i.e., a retrovirus) for transferring a nucleic acid into a cell is also referred to herein as a transducing retrovirus. Exogenous nucleic acid material contained within the retrovirus is incorporated into the genome of the transduced cell. A cell that has been transduced with a DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include a nucleic acid encoding an antigen from a *Mycobacterium* species together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

The term "domain" as used herein applies to a portion or subsequence of amino acids within a peptide or nucleic acids within a nucleotide sequence. In some embodiments, a domain provides a functionality, activity, or benefit. In some embodiments for example a domain may be a receptor or a signaling portion of a receptor. In another embodiment a domain may have a linker function between two other domains. In another embodiment a domain may serve to bind a specific target analyte (target domain), such as an antigen or chemokine.

As used herein, the term "combination" refers to any arrangement possible of various components (e.g. mycobacterial antigens and/or encoding nucleic acid molecules). Such an arrangement includes mixture of mycobacterial antigens (e.g. mixture of individual antigens and/or fusion of antigens) or mixture of nucleic acid molecules (e.g. carried by one or more vector) as well as mixture of polypeptide(s) and nucleic acid molecule(s). The present invention encompasses combinations comprising equal molar concentrations of each component as well as combinations with very different concentrations. It is appreciated that optimal concentration of each *Mycobacterium* component can be determined by the artisan skilled in the art.

As used herein, the term "immunogenic" refers to the ability to induce or stimulate a measurable T and/or B cell-mediated immune response in a subject into which the component qualified as immunogenic has been introduced. For example, the antigenic combination of the invention is immunogenic in the sense as it is capable of inducing or stimulating an immune response in a subject which can be innate and/or specific (i.e. against at least one mycobacterial antigen/epitope comprised in or expressed by said immunogenic combination), humoral and/or cellular (e.g. production of antibodies and/or cytokines and/or the activation of cytotoxic T cells, B, T lymphocytes, antigen presenting cells, helper T cells, dendritic cells, NK cells, etc) and usually results in a protective response in the administered subject. A vast variety of direct or indirect biological assays are available in the art to evaluate the immunogenic nature of a component either in vivo (animal or human being), or in vitro (e.g. in a biological sample) as described herein.

As used herein, the term "mycobacterial antigen" refers to a polypeptide present in or obtained from a *Mycobacterium* species or fragment thereof (e.g. an epitope) capable of being bound by an antibody or a T cell receptor. Typically, such an antigen contains one or more B and/or T epitope(s), in particular CTL or TH epitope(s) or both, involved in recognition by a particular antibody or T-cell receptor in the context of the Major Histocompatibility Complex (MHC). In the context of the invention, this term encompasses native mycobacterial polypeptide as well as fragment and modified version thereof (i.e. variant) as described hereinafter.

An "epitope" corresponds to a minimal peptide motif (usually a set of 8-25 amino acid residues) that forms a site recognized by an antibody, a T-cell receptor or a HLA molecule. Those residues can be consecutive (linear epitope) or not (conformational epitope that includes residues that are not immediately adjacent to one another).

As used herein, the term "variants" is intended to mean substantially similar sequences. For nucleic acid molecules, a variant comprises a nucleic acid molecule having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" nucleic acid molecule or polypeptide comprises a naturally occurring nucleotide sequence or amino acid sequence, respectively. For nucleic acid molecules, conservative variants include those sequences that, because of the degeneracy of the genetic code, encode the amino acid sequence of one of the polypeptides of the disclosure. Variant nucleic acid molecules also include synthetically derived nucleic acid molecules, such as those generated, for example, by using site-directed mutagenesis but which still encode a protein of the disclosure. Generally, variants of a particular nucleic acid molecule of the disclosure will have at least about 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

As used herein, "conservative" amino acid substitutions may be defined as set out in Tables A, B, or C below. The polypeptides of the disclosure include those wherein conservative substitutions (from either nucleic acid or amino acid sequences) have been introduced by modification of polynucleotides encoding antigen(s) from a *Mycobacterium* species. In some embodiments, these polypeptides comprise CDRs or functional fragments thereof. Amino acids can be classified according to physical properties and contribution to secondary and tertiary protein structure. A conservative substitution is recognized in the art as a substitution of one amino acid for another amino acid that has similar properties. In some embodiments, the conservative substitution is recognized in the art as a substitution of one nucleic acid for another nucleic acid that has similar properties, or, when encoded, has a binding affinity to a target or binding partner similar to the binding affinity of the sequence upon which the conservative substitution is based. Exemplary conservative substitutions are set out in Table A.

TABLE A

| Conservative Substitutions I | |
|---|---|
| Side Chain Characteristics | Amino Acid |
| Aliphatic | |
| Non-polar | G A P I L V F |
| Polar - uncharged | C S T M N Q |
| Polar - charged | D E K R |
| Aromatic | H F W Y |
| Other | NQDE |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

| Conservative Substitutions II | |
|---|---|
| Side Chain Characteristic | Amino Acid |
| Non-polar (hydrophobic) | |
| Aliphatic: | A L I V P |
| Aromatic: | F W Y |
| Sulfur-containing: | M |
| Borderline: | G Y |
| Uncharged-polar | |
| Hydroxyl: | S T Y |
| Amides: | N Q |
| Sulfhydryl: | C |
| Borderline: | G Y |
| Positively Charged (Basic): | K R H |
| Negatively Charged (Acidic): | D E |

Alternately, exemplary conservative substitutions are set out in Table C.

TABLE C

| Conservative Substitutions III | |
|---|---|
| Original Residue | Exemplary Substitution |
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the antigen(s) from a *Mycobacterium* species, or any fragments thereof described herein are intended to include amino acid sequences comprising polypeptides bearing one or more insertions, deletions, or substitutions, or any combination thereof, of amino acid residues as well as modifications other than insertions, deletions, or substitutions of amino acid residues, such as but not limited to conservative amino acid substitutions.

As used herein, the term "fragment" or "functional fragment" means any portion of a polypeptide that is of a sufficient length to retain at least partial biological function that is similar to or substantially similar to the wild-type polypeptide upon which the fragment is based. In some embodiments, a fragment of a polypeptide associated with an antigen from a *Mycobacterium* species is a polypeptide that comprises 50, 55, 60, 65, 70, 75, 80, 85, 90, 95, 96, 97, 98, or 99% sequence identity of any polypeptide disclosed herein, and in particular any polypeptide comprising an amino acid sequence selected from SEQ ID NOs 6-10. In some embodiments, the fragment is a fragment of any polypeptide disclosed herein, and in particular any polypeptide comprising an amino acid sequence selected from SEQ ID NOs 6-10, and has a length of at least about 10, about 20, about 30, about 40, about 50, about 60, about 70, about 80, about 90, or about 100 contiguous amino acids. In some embodiments, the fragment is a fragment of any polypeptide disclosed herein, and in particular any polypeptide comprising an amino acid sequence selected from SEQ ID NOs 6-10 and has a length of at least about 50 amino acids. In some embodiments, the fragment is a fragment of any polypeptide disclosed herein, and in particular any polypeptide comprising an amino acid sequence selected from SEQ ID NOs 6-10, and has a length of at least about 100 amino acids. In some embodiments, the fragment is a fragment of any polypeptide disclosed herein, and in particular any polypeptide comprising an amino acid sequence selected from SEQ ID NOs 6-10, and has a length of at least about 150 amino acids. In some embodiments, the fragment is a fragment of any polypeptide disclosed herein, and in particular any polypeptide comprising an amino acid sequence selected from SEQ ID NOs 6-10 and has a length of at least about 200 amino acids. In some embodiments, the fragment is a fragment of any polypeptide disclosed in Table 1 and has a length of at least about 250 amino acids. In some embodiments, the fragment is a fragment of any polypeptide disclosed herein, and in particular any polypeptide comprising an amino acid sequence selected from SEQ ID NOs 6-10, and has a length of at least about 300 amino acids. In some embodiments, the fragment is a fragment of any polypeptide disclosed herein, and in particular any polypeptide comprising an amino acid sequence selected from SEQ ID NOs 6-10, and has a length of at least about 350 amino acids. In some embodiments, the fragment is a fragment of any polypeptide disclosed herein, and in particular any polypeptide comprising an amino acid sequence selected from SEQ ID NOs 6 through 10, and has a length of at least about 400 amino acids.

As used herein, "more than one" or "two or more" 2, 3, 4, 5, 6, 7, 8, 9, or 10 or more. In some embodiments, "more than one" means 2, 3, 4, or 5 of the amino acids or nucleic acids or mutations described herein. In some embodiments, "more than one" means 2, 3, or 4 of the amino acids or nucleic acids or mutations described herein. In some embodiments, "more than one" means 2 or 3 of the amino acids or nucleic acids or mutations described herein. In some embodiments, "more than one" means 2 of the amino acids or nucleic acids or mutations described herein.

"Sequence homology" or "sequence identity" or "homologous to" are used herein interchangeably for nucleotides and amino acids sequences determined using FASTA, BLAST and Gapped BLAST (Altschul et al., Nuc. Acids Res., 1997, 25, 3389, which is incorporated herein by reference in its entirety) and PAUP* 4.0bIO software (D. L. Swofford, Sinauer Associates, Massachusetts). Briefly, the BLAST algorithm, which stands for Basic Local Alignment Search Tool is suitable for determining sequence similarity (Altschul et al., J. Mol. Biol, 1990, 215, 403-410, which is incorporated herein by reference in its entirety). Software for performing BLAST analyses is publicly available through the National Center for Biotechnology Information (http://www.ncbi.nlm.nih.gov). One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001. "Percentage of similarity" or percentage of sequence identity" can be calculated using PAUP* 4.0bIO software (D. L. Swofford, Sinauer Associates, Massachusetts). The average similarity of the consensus sequence is calculated compared to all sequences in the phylogenic tree. In some embodiments, the compositions disclosed herein comprise nucleic acid sequences that are at least 50%, 55%, 60%, 65%, 70%, 75%, 80%, 85%, 90%, 95%, 96%, 97%, 98%, 99% homologous to any of SEQ ID NOS: 1-5, or amino acid sequences that are at least 50%, 55%, 60%, 65%, 70%, 75%, 80%, 85%, 90%, 95%, 96%, 97%, 98%, 99% homologous to any of SEQ ID NOS: 6-10.

The "percent identity" or "percent homology" of two polynucleotide or two polypeptide sequences may be determined by comparing the sequences using the GAP computer program (a part of the GCG Wisconsin Package, version 10.3 (Accelrys, San Diego, Calif.)) using its default parameters. "Identical" or "identity" as used herein in the context of two or more nucleic acids or amino acid sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine T) and uracil (U) may be considered equivalent. Identity may be performed manually or by using a computer sequence algorithm such as BLAST or BLAST 2.0.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In some embodiments, the nucleic acid molecules of the disclosure comprise a contiguous open reading frame encoding an antigen, or a fragment thereof, as described herein. "Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions. Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine Nucleic acids may be obtained by chemical synthesis methods or by recombinant methods. A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference in their entireties. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2-OH-group may be replaced by a group selected from H, OR, R, halo, SH, SR, NH$_2$, NHR, N$_2$ or CN, wherein R is C$_1$-C$_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature (Oct. 30, 2005), Soutschek et al., Nature 432:173-178 (2004), and U.S. Patent Publication No. 20050107325, which are incorporated herein by reference in their entireties. Modified nucleotides and nucleic acids may also include locked nucleic acids (LNA), as described in U.S. Patent No. 20020115080, which is incorporated herein by reference. Additional modified nucleotides and nucleic acids are described in U.S. Patent Publication No. 20050182005, which is incorporated herein by reference in its entirety. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

The terms "polypeptide", "peptide" and "protein" are used interchangeably herein to refer to polymers of amino acids of any length. The polymer may be linear or branched, it may comprise modified amino acids, and it may be interrupted by non-natural amino acids or chemical groups that are not amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having the complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

As used herein, the terms "treat," "treated," or "treating" can refer to therapeutic treatment and/or prophylactic or preventative measures wherein the object is to prevent or slow down (lessen) an undesired physiological condition, disorder or disease, or obtain beneficial or desired clinical results. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment can also include eliciting a clinically significant response without excessive levels of side effects. Treatment also includes prolonging survival as compared to expected survival if not receiving treatment.

As used herein, the terms "diagnose," "diagnosing," or variants thereof refer to identifying the nature of a physiological condition, disorder or disease. In some embodiments, diagnosing a subject refers to identifying whether a patient has Mycobacterial infection.

The term "parenteral" administration of an immunogenic composition includes, e.g., subcutaneous (s.c), intravenous (i.v.), intramuscular (i.m.), or intracisternal injection, intratumoral, or infusion techniques.

The present disclosure also provides prophylactic methods. In some embodiments, a method of preventing a Myobacterial infection by administering a cell or a polypeptide, as disclosed herein to a subject who is not, at the time, infected with a Mycobacterial infection. For instance, in certain aspects, the present disclosure provides a method of reducing a patient's risk of a Mycobacterial infection, comprising administering to a subject in need thereof a composition or pharmaceutical composition, as described herein, in an amount effective to reduce the risk of a Mycobacterial infection. For example the risk may be reduced by, e.g., at least 25%, 50%, 75%, 80%, 85%, 90%, 95%, 97%, 98%, 99%, or more. In some embodiments, the compositions or pharmaceutical compositions described herein are provided to a patient who does not have a Mycobacterial infection, with the result that if a Mycobacterial infection occurs, the course of the disease is likely to be milder than the course of disease in a similar patient who has not received the composition or pharmaceutical composition. Such risk may be reduced, e.g., by at least 25%, 50%, 75%, 80%, 85%, 90%, 95%, 97%, 98%, 99%, or more compared to a patient that did not receive the composition or pharmaceutical composition.

The term "therapeutically effective amount" means a quantity sufficient to achieve a desired therapeutic or prophylactic effect, for example, an amount which results in the prevention or amelioration of or a decrease in the symptoms associated with a disease that is being treated, e.g., a Mycobacterial infection. The amount of compound administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The regimen of administration can affect what constitutes an effective amount. The compound of the invention can be administered to the subject either prior to or after the onset of a Mycobacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation. Typically, an effective amount of the compounds of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. The compounds of the present invention can also be administered in combination with each other, or with one or more additional therapeutic compounds. Generally, therapeutically effective amount refers to an amount of a composition or pharmaceutical composition that ameliorates symptoms, or reverses, prevents or reduces the rate of progress of disease, or extends life span of an individual when administered alone or in combination with other therapeutic agents or treatments as compared to the symptoms, rate of progress of disease, or life span of an individual not receiving a therapeutically effective amount an inhibitor disclosed herein.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water, isotonic saline; Ringer's solution; ethyl alcohol; phosphate buffer solutions; and other non-toxic compatible substances employed in pharmaceutical formulations. Suitable pharmaceutical carriers are described in "Remington's Pharmaceutical Sciences" by E. W. Martin, which is incorporated herein by reference in its entirety.

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Acid addition salts of the compounds of the invention are most suitably formed from pharmaceutically acceptable acids, and include for example those formed with inorganic acids e.g. hydrochloric, hydrobromic, sulphuric or phosphoric acids and organic acids e.g. succinic, malaeic, acetic or fumaric acid. Other non-pharmaceutically acceptable salts e.g. oxalates can be used for example in the isolation of the compounds of the invention, for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt. In vivo hydrolyzable esters or amides of certain compounds of the invention can be formed by treating those compounds having a free hydroxy or amino functionality with the acid chloride of the desired ester in the presence of a base in an inert solvent such as methylene chloride or chloroform. Suitable bases include triethylamine or pyridine. Conversely, compounds of the invention having a free carboxy group can be esterified using standard conditions which can include activation followed by treatment with the desired alcohol in the presence of a suitable base. In some embodiments, the disclosure relates to a composition comprising consisting essentially of or consisting of polynucleotides expressing one or a plurality of polynucleotides that encode one or a combination of the amino acid sequences that are mycobacterial antigens disclosed herein. Methods of exposing isolated T cells are disclosed herein wherein the methods comprise exposing the compositions to one or more isolated T cells.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphthalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Particularly preferred salts are sodium, lysine and arginine salts of the compounds of the invention. Such salts can be formed by procedures well known and described in the art.

Other acids such as oxalic acid, which cannot be considered pharmaceutically acceptable, can be useful in the preparation of salts useful as intermediates in obtaining a chemical compound of the invention and its pharmaceutically acceptable acid addition salt. Metal salts of a chemical compound of the invention include alkali metal salts, such as the sodium salt of a chemical compound of the invention containing a carboxy group. Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

As used herein, "control sample" or "reference sample" refer to samples with a known presence, absence, or quantity of substance being measured, that is used for comparison against an experimental sample.

The term "Chimeric Antigen Receptor" or alternatively a "CAR" refers to a set of polypeptides, typically two in the simplest embodiments, which when in an immune effector cell or plurality of cells disclosed herein, provides the cell or cells with specificity for a target cell and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from the costimulatory molecules described herein, e.g., 4-1BB (i.e., CD137), CD27 and/or CD28. In some embodiments, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more costimulatory molecule (s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In one aspect, the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

A CAR that comprises an antigen binding domain (e.g., a scFv, or TCR) that targets a specific mycobacterial antigen X, such as those described herein, is also referred to as XCAR. For example, a CAR that comprises an antigen binding domain that targets ESXA is referred to as ESXA-CAR.

The term "signaling domain" refers to the functional portion of a protein which acts by transmitting information within the cell to regulate cellular activity via defined signaling pathways by generating second messengers or functioning as effectors by responding to such messengers.

As used herein, the term "binding domain" or "antibody molecule" refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CDS, ICAM-1, LFA-1 (CD1 1a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD 160, CD 19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB 1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, CD 19a, and a ligand that specifically binds with CD83.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes. "Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell.

In the case of a T cell, primary stimulation and co-stimulation are examples of immune effector function or response.

*Mycobacterium* Species

As described herein, the mycobacterial antigens comprised by the nucleic acid sequences, amino acid sequences, or fragments thereof of the invention can independently be obtained from any member of a *Mycobacterium* (M.) species. A vast number of Mycobacteria for use in the context of the invention are described in the art, and are intended to be included in the present disclosure. Exemplary *Mycobacterium* species include without limitation *M. tuberculosis, M. bovis, M. bovis* BCG, *M. avium, M. abscessus, M. chelonae, M. kansasii, M. africanum, M. canetti, M. caprae, M. microt, M. mungi, M. orygis, M. avium, M. avium paratuberculosis, M. avium silvaticum, M. columbiense, M. intracellulare, M. gordonae, M. ulcerans, M. genavense, M. scrofulaceum, M. intermedium, M. fortuitum,* and *M. mucogenicum.*

In some embodiments, the mycobacterial antigens are from a *Mycobacterium* species of the tuberculosis complex which includes those species traditionally considered as causing the disease tuberculosis, as well as *Mycobacterium* environmental and opportunistic species that cause tuberculosis and pulmonary disease in immune compromised subjects (e.g. HIV-infected patients). Exemplary *Mycobacterium tuberculosis* antigens are shown below in Table 1.

TABLE 1

| Species | Antigen | Protein Refseq # | Gene Reference (NCBI) |
|---|---|---|---|
| Mycobacterium tuberculosis | AG85B | NP_216402.1 | 885785 |
| | PPE68 | YP_178022.1 | 886201 |

TABLE 1-continued

| Species | Antigen | Protein Refseq # | Gene Reference (NCBI) |
|---|---|---|---|
| (strain ATCC 25618/ H37Rv) | ESXA | YP_178023.1 | 886209 |
| | ESXB | NP_218391.1 | 886194 |
| | ADK | NP_215247.1 | 888567 |
| | MCEIA | YP_177701.1 | 886823 |
| | LPDC | NP_214976.1 | 886300 |
| | Rv2251 | NP_216767.1 | 888706 |
| | ESXC | NP_218407.1 | 886222 |
| | ESXD | NP_218408.1 | 886218 |
| | ESXE | NP_218421.1 | 886237 |
| | ESXF | NP_218422.1 | 886239 |
| | ESXG | NP_214801.1 | 886604 |
| | ESXH | NP_214802.1 | 886603 |
| | PE-PGRS | YP_177846.1 | 885551 |
| | Ag85a | NP_218321.1 | 886132 |
| | Ag85c | YP_177694.1 | 886885 |
| | APA | YP_177849.1 | 885896 |
| | TRXA | NP_218431.1 | 886241 |
| | MPT51 | YP_178017.1 | 886121 |
| | MPT53 | NP_217394.1 | 887184 |
| | MPT63 | NP_216442.1 | 885334 |
| | MPT64 | NP_216496.1 | 885925 |
| | GROEL2 | NP_214954.1 | 886354 |

Amino acid sequences of the suitable mycobacterial antigens and the encoding nucleotide sequences are readily available in publically available data banks and in the literature. For example, protein RefSeq identifiers and NCBI gene reference numbers for exemplary *Mycobacterium tuberculosis* antigens are shown in Table 1, above. However, it is to be understood that the present invention is not limited to these exemplary *Mycobacterium* species and antigens. Indeed the nucleotide and amino acid sequences can vary between different isolates and strains and this natural genetic variation is included within the scope of the invention as well as non-natural modification(s) such as those described below.

Compositions

The present disclosure relates to compositions comprising one or more nucleic acid sequences encoding one or more antigens, or functional fragments thereof, from a *Mycobacterium* species. In certain embodiments, antigens, or functional fragments thereof, are shown in Table 1. The present disclosure also relates to compositions comprising one or more polypeptides, comprising an amino acid sequence, or fragment thereof, coding for one or more antigens, from a *Mycobacterium* species.

In some embodiments, the present disclosure relates to compositions comprising at least two nucleic acid sequences encoding at least two antigens, or functional fragments thereof, from a *Mycobacterium* species. In some embodiments, at least two is a number comprised within a range from 2 to 10 (i.e. 2, 3, 4, 5, 6, 7, 8, 9, 10, etc.). In some embodiments, the present disclosure relates to compositions comprising at least three nucleic acid sequences encoding at least three antigens, or functional fragments thereof, from a *Mycobacterium* species. In some embodiments, at least three is a number comprised within a range from 3 to 10 (i.e. 3, 4, 5, 6, 7, 8, 9, 10, etc.). In some embodiments, the present disclosure relates to compositions comprising at least four nucleic acid sequences encoding at least four antigens, or functional fragments thereof, from a *Mycobacterium* species. In some embodiments, at least four is a number comprised within a range from 4 to 10 (i.e. 4, 5, 6, 7, 8, 9, 10, etc.). In some embodiments, the present disclosure relates to compositions comprising at least five nucleic acid sequences encoding at least three antigens, or functional fragments thereof, from a *Mycobacterium* species. In some embodiments, at least five is a number comprised within a range from about 5 to about 10 (i.e. 5, 6, 7, 8, 9, 10, etc.). In certain embodiments, antigens, or functional fragments thereof, are shown in Table 1.

In another embodiment, the present disclosure relates to compositions comprising at least two polypeptides comprising at least two amino acid sequences, or fragments thereof, coding for at least two antigens, from a *Mycobacterium* species. In some embodiments, at least two is a number comprised within a range from 2 to 10 (i.e. 2, 3, 4, 5, 6, 7, 8, 9, 10, etc.). In some embodiments, the present disclosure relates to compositions comprising at least three polypeptides comprising at least three amino acid sequences, or fragments thereof, coding for at least three antigens, from a *Mycobacterium* species. In some embodiments, at least three is a number comprised within a range from 3 to 10 (i.e. 3, 4, 5, 6, 7, 8, 9, 10, etc.). In some embodiments, the present disclosure relates to compositions comprising at least four polypeptides comprising at least two amino acid sequences, or fragments thereof, coding for at least four antigens, from a *Mycobacterium* species. In some embodiments, at least four is a number comprised within a range from 4 to 10 (i.e. 4, 5, 6, 7, 8, 9, 10, etc.). In some embodiments, the present disclosure relates to compositions comprising at least five polypeptides comprising at least five amino acid sequences, or fragments thereof, coding for at least two antigens, from a *Mycobacterium* species. In some embodiments, at least five is a number comprised within a range from 5 to 10 (i.e. 5, 6, 7, 8, 9, 10, etc.). In certain embodiments, antigens, or functional fragments thereof, are shown in Table 1.

In the context of the present invention the at least two antigens from a *Mycobacterium* species, the at least three antigens from a *Mycobacterium* species, the at least four antigens from a *Mycobacterium* species, the at least five antigens from a *Mycobacterium* species, are different from each other (e.g. multiple copies of the same mycobacterial antigen can be used provided that the combination comprises/encodes at least 5 different mycobacterial antigens). In certain embodiments, antigens, or functional fragments thereof, are shown in Table 1.

In some embodiments, the antigen, or functional fragment thereof, from a *Mycobacterium* species is an Ag85B antigen. In some embodiments, the antigen, or functional fragment thereof, from a *Mycobacterium* species is a PPE68 antigen. In some embodiments, the antigen, or functional fragment thereof, from a *Mycobacterium* species is an ESXA antigen. In some embodiments, the antigen, or functional fragment thereof, from a *Mycobacterium* species is an ESXB antigen. In some embodiments, the antigen, or functional fragment thereof, from a *Mycobacterium* species is an ADK antigen.

In some embodiments, the compositions of the present invention comprise or encode at least two mycobacterial antigens selected from the group consisting of: Ag85B, PPE68, ESXA, ESXB and ADK. In some embodiments, the compositions of the present invention comprise or encode at least three mycobacterial antigens selected from the group consisting of Ag85B, PPE68, ESXA, ESXB and ADK. In some embodiments, the compositions of the present invention comprise or encode at least four mycobacterial antigens selected from the group consisting of Ag85B, PPE68, ESXA, ESXB and ADK. In some embodiments, the compositions of the present invention comprise or encode at least five mycobacterial antigens selected from the group consisting of Ag85B, PPE68, ESXA, ESXB and ADK.

In one aspect, the present disclosure features a composition comprising a nucleic acid sequence encoding an Ag85B antigen, or a functional fragment thereof, from a *Mycobacterium* species, a nucleic acid encoding a PPE68 antigen, or a functional fragment thereof, from a *Mycobacterium* species, a nucleic acid encoding a ESXA antigen, or a functional fragment thereof, from a *Mycobacterium* species, a nucleic acid encoding an ESXB antigen, or a functional fragment thereof, from a *Mycobacterium* species, a nucleic acid encoding an ADK antigen, or a functional fragment thereof, from a *Mycobacterium* species, or a combination thereof.

In some embodiments, the Ag85B antigen corresponds to NCBI Gene Reference #885785 (diacylglycerol acyltransferase/mycolyltransferase Ag85B). In some embodiments, the nucleic acid sequence encoding an Ag85B antigen, or a functional fragment thereof, is at least 50% identical to NCBI Gene Reference #885785. In some embodiments, the nucleic acid sequence encoding an Ag85B antigen, or a functional fragment thereof, is at least 50%, at least 55%, at least 60%, at least 65%, at least 70%, at least 75%, at least 80%, at least 85%, at least 90%, at least 95% identical to NCBI Gene Reference #885785. In some embodiments, the nucleic acid sequence encoding an Ag85B antigen, or a functional fragment thereof, is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Gene Reference #885785. NCBI Gene Reference #885785 nucleic acid sequence is shown below as SEQ ID NO. 1.

```
                                              SEQ ID NO. 1
ATGACAGACGTGAGCCGAAAGATTCGAGCTTGGGGACGCCGATTGATGA

TCGGCACGGCAGCGGCTGTAGTCCTTCCGGGCCTGGTGGGGCTTGCCGG

CGGAGCGGCAACCGCGGGCGCGTTCTCCCGGCCGGGGCTGCCGGTCGAG

TACCTGCAGGTGCCGTCGCCGTCGATGGGCCGCGACATCAAGGTTCAGT

TCCAGAGCGGTGGGAACAACTCACCTGCGGTTTATCTGCTCGACGGCCT

GCGCGCCCAAGACGACTACAACGGCTGGGATATCAACACCCCGGCGTTC

GAGTGGTACTACCAGTCGGGACTGTCGATAGTCATGCCGGTCGGCGGGC

AGTCCAGCTTCTACAGCGACTGGTACAGCCCGGCCTGCGGTAAGGCTGG

CTGCCAGACTTACAAGTGGGAAACCTTCCTGACCAGCGAGCTGCCGCAA

TGGTTGTCCGCCAACAGGGCCGTGAAGCCCACCGGCAGCGCTGCAATCG

GCTTGTCGATGGCCGGCTCGTCGGCAATGATCTTGGCCGCCTACCACCC

CCAGCAGTTCATCTACGCCGGCTCGCTGTCGGCCCTGCTGGACCCCTCT

CAGGGGATGGGGCCTAGCCTGATCGGCCTCGCGATGGGTGACGCCGGCG

GTTACAAGGCCGCAGACATGTGGGGTCCCTCGAGTGACCCGGCATGGGA

GCGCAACGACCCTACGCAGCAGATCCCCAAGCTGGTCGCAAACAACACC

CGGCTATGGGTTTATTGCGGGAACGGCACCCCGAACGAGTTGGGCGGTG

CCAACATACCCGCCGAGTTCTTGGAGAACTTCGTTCGTAGCAGCAACCT

GAAGTTCCAGGATGCGTACAACGCCGCGGGCGGGCACAACGCCGTGTTC

AACTTCCCGCCCAACGGCACGCACAGCTGGGAGTACTGGGGCGCTCAGC

TCAACGCCATGAAGGGTGACCTGCAGAGTTCGTTAGGCGCCGGCTGA
```

In some embodiments, the PPE68 antigen corresponds to NCBI Gene Reference #886201 (PPE family protein PPE68). In some embodiments, the nucleic acid sequence encoding a PPE68 antigen, or a functional fragment thereof, is at least 50% identical to NCBI Gene Reference #886201. In some embodiments, the nucleic acid sequence encoding a PPE68 antigen, or a functional fragment thereof, is at least 50%, at least 55%, at least 60%, at least 65%, at least 70%, at least 75%, at least 80%, at least 85%, at least 90%, at least 95% identical to NCBI Gene Reference #886201. In some embodiments, the nucleic acid sequence encoding a PPE68 antigen, or a functional fragment thereof, is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Gene Reference #886201. NCBI Gene Reference #886201 nucleic acid sequence is shown below as SEQ ID NO. 2.

```
                                              SEQ ID NO. 2
ATGCTGTGGCACGCAATGCCACCGGAGCTAAATACCGCACGGCTGATGGC

CGGCGCGGGTCCGGCTCCAATGCTTGCGGCGGCCGCGGGATGGCAGACGC

TTTCGGCGGCTCTGGACGCTCAGGCCGTCGAGTTGACCGCGCGCCTGAAC

TCTCTGGGAGAAGCCTGGACTGGAGGTGGCAGCGACAAGGCGCTTGCGGC

TGCAACGCCGATGGTGGTCTGGCTACAAACCGCGTCAACACAGGCCAAGA

CCCGTGCGATGCAGGCGACGGCGCAAGCCGCGGCATACACCCAGGCCATG

GCCACGACGCCGTCGCTGCCGGAGATCGCCGCCAACCACATCACCCAGGC

CGTCCTTACGGCCACCAACTTCTTCGGTATCAACACGATCCCGATCGCGT

TGACCGAGATGGATTATTTCATCCGTATGTGGAACCAGGCAGCCCTGGCA

ATGGAGGTCTACCAGGCCGAGACCGCGGTTAACACGCTTTTCGAGAAGCT

CGAGCCGATGGCGTCGATCCTTGATCCCGGCGCGAGCCAGAGCACGACGA

ACCCGATCTTCGGAATGCCCTCCCCTGGCAGCTCAACACCGGTTGGCCAG

TTGCCGCCGGCGGCTACCCAGACCCTCGGCCAACTGGGTGAGATGAGCGG

CCCGATGCAGCAGCTGACCCAGCCGCTGCAGCAGGTGACGTCGTTGTTCA

GCCAGGTGGGCGGCACCGGCGGCGGCAACCCAGCCGACGAGGAAGCCGCG

CAGATGGGCCTGCTCGGCACCAGTCCGCTGTCGAACCATCCGCTGGCTGG

TGGATCAGGCCCCAGCGCGGGCGCGGGCCTGCTGCGCGCGGAGTCGCTAC

CTGGCGCAGGTGGGTCGTTGACCCGCACGCCGCTGATGTCTCAGCTGATC

GAAAAGCCGGTTGCCCCCTCGGTGATGCCGGCGGCTGCTGCCGGATCGTC

GGCGACGGGTGGCGCCGCTCCGGTGGGTGCGGGAGCGATGGGCCAGGGTG

CGCAATCCGGCGGCTCCACCAGGCCGGGTCTGGTCGCGCCGGCACCGCTC

GCGCAGGAGCGTGAAGAAGACGACGAGGACGACTGGGACGAAGAGGACGA

CTGGTGA
```

In some embodiments, the ESXA antigen corresponds to NCBI Gene Reference #886209 (ESAT-6 protein EsxA). In some embodiments, the nucleic acid sequence encoding an ESXA antigen, or a functional fragment thereof, is at least 50% identical to NCBI Gene Reference #886209. In some embodiments, the nucleic acid sequence encoding an ESXA antigen, or a functional fragment thereof, is at least 50%, at least 55%, at least 60%, at least 65%, at least 70%, at least 75%, at least 80%, at least 85%, at least 90%, at least 95% identical to NCBI Gene Reference #886209. In some embodiments, the nucleic acid sequence encoding an ESXA antigen, or a functional fragment thereof, is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Gene Reference #886209. NCBI Gene Reference #886209 nucleic acid sequence is shown below as SEQ ID NO. 3.

SEQ ID NO. 3
ATGACAGAGCAGCAGTGGAATTTCGCGGGTATCGAGGCCGCGGCAAGCGC

AATCCAGGGAAATGTCACGTCCATTCATTCCCTCCTTGACGAGGGGAAGC

AGTCCCTGACCAAGCTCGCAGCGGCCTGGGGCGGTAGCGGTTCGGAGGCG

TACCAGGGTGTCCAGCAAAAATGGGACGCCACGGCTACCGAGCTGAACAA

CGCGCTGCAGAACCTGGCGCGGACGATCAGCGAAGCCGGTCAGGCAATGG

CTTCGACCGAAGGCAACGTCACTGGGATGTTCGCATAG

In some embodiments, the ESXB antigen corresponds to NCBI Gene Reference #886194 (ESAT-6-like protein EsxB). In some embodiments, the nucleic acid sequence encoding an ESXB antigen, or a functional fragment thereof, is at least 50% identical to NCBI Gene Reference #886194. In some embodiments, the nucleic acid sequence encoding an ESXB antigen, or a functional fragment thereof, is at least 50%, at least 55%, at least 60%, at least 65%, at least 70%, at least 75%, at least 80%, at least 85%, at least 90%, at least 95% identical to NCBI Gene Reference #886194. In some embodiments, the nucleic acid sequence encoding an ESXB antigen, or a functional fragment thereof, is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Gene Reference #886194. NCBI Gene Reference #886194 nucleic acid sequence is shown below as SEQ ID NO. 4.

SEQ ID NO. 4
ATGGCAGAGATGAAGACCGATGCCGCTACCCTCGCGCAGGAGGCAGGTAA

TTTCGAGCGGATCTCCGGCGACCTGAAAACCCAGATCGACCAGGTGGAGT

CGACGGCAGGTTCGTTGCAGGGCCAGTGGCGCGGCGCGGCGGGGACGGCC

GCCCAGGCCGCGGTGGTGCGCTTCCAAGAAGCAGCCAATAAGCAGAAGCA

GGAACTCGACGAGATCTCGACGAATATTCGTCAGGCCGGCGTCCAATACT

CGAGGGCCGACGAGGAGCAGCAGCAGGCGCTGTCCTCGCAAATGGGCTTC

TGA

In some embodiments, the ADK antigen corresponds to NCBI Gene Reference #888567 (adenylate kinase). In some embodiments, the nucleic acid sequence encoding an ADK antigen, or a functional fragment thereof, is at least 50% identical to NCBI Gene Reference #888567. In some embodiments, the nucleic acid sequence encoding an ADK antigen, or a functional fragment thereof, is at least 50%, at least 55%, at least 60%, at least 65%, at least 70%, at least 75%, at least 80%, at least 85%, at least 90%, at least 95% identical to NCBI Gene Reference #888567. In some embodiments, the nucleic acid sequence encoding an ADK antigen, or a functional fragment thereof, is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Gene Reference #888567. NCBI Gene Reference #888567 nucleic acid sequence is shown below as SEQ ID NO. 5.

SEQ ID NO. 5
GTGAGAGTTTTGTTGCTGGGACCGCCCGGGGGGGCAAGGGGACGCAGGC

GGTGAAGCTGGCCGAGAAGCTCGGGATCCCGCAGATCTCCACCGGCGAAC

TCTTCCGGCGCAACATCGAAGAGGGCACCAAGCTCGGCGTGGAAGCCAAA

CGCTACTTGGATGCCGGTGACTTGGTGCCGTCCGACTTGACCAATGAACT

CGTCGACGACCGGCTGAACAATCCGGACGCGGCCAACGGATTCATCTTGG

ATGGCTATCCACGCTCGGTCGAGCAGGCCAAGGCGCTTCACGAGATGCTC

GAACGCCGGGGGACCGACATCGACGCGGTGCTGGAGTTTCGTGTGTCCGA

GGAGGTGTTGTTGGAGCGACTCAAGGGGCGTGGCCGCGCCGACGACACCG

ACGACGTCATCCTCAACCGGATGAAGGTCTACCGCGACGAGACCGCGCCG

CTGCTGGAGTACTACCGCGACCAATTGAAGACCGTCGACGCCGTCGGCAC

CATGGACGAGGTGTTCGCCCGTGCGTTGCGGGCTCTGGGAAAGTAG

The nucleic molecules of the invention may be native nucleic acids (e.g. isolated from a genome or genomic fragment of a *Mycobacterium*) or may be modified to include substitution, deletion, addition and/or insertion of one or more nucleotide(s). The present invention encompasses any modifications aimed to improve cloning, expression, stability (e.g. introduction of appropriate restriction sites, degeneration and/or optimization of nucleotide sequence to optimize translation in a given host cell and/or suppression of potentially negative elements that may destabilize the nucleic acid molecule or its transcript). When several modifications are contemplated, they can concern consecutive and/or non-consecutive nucleotide residues. The modification(s) contemplated by the present invention encompass silent modifications that do not change the amino acid sequence of the encoded mycobacterial antigens and fusion polypeptides, as well as modifications that are translated into the encoded mycobacterial polypeptide. Preferably the modifications do not decrease the immunogenic potential of encoded mycobacterial antigens and fusion polypeptides with respect to the non-modified ones.

Alternatively or in addition, the nucleic acid molecule of the invention can be optimized for providing high level expression in a particular host cell or subject, e.g. avian (e.g. chicken embryonic fibroblast, *Cairina moschata* cell lines described in WO2010/130756 and WO2012/001075), mammalian, yeast (e.g. *Saccharomyces cerevisiae*, *Saccharomyces pombe* or *Pichia pastoris*) or bacteria (e.g. *E. coli*, BCG or *Listeria*). It has been indeed observed that, when more than one codon is available to code for a given amino acid, the codon usage patterns of organisms are highly non-random and the utilisation of codons may be markedly different between different hosts. As the nucleotide sequences used in the invention are mostly of bacterial origin, they may have an inappropriate codon usage pattern for efficient expression in host cells such as higher eukaryotic cells. Typically, codon optimization is performed by replacing one or more "native" (mycobacterial) codon corresponding to a codon infrequently used in the host cell of interest by one or more codon encoding the same amino acid which is more frequently used. It is not necessary to replace all native codons corresponding to infrequently used codons since increased expression can be achieved even with partial replacement. Moreover, some deviations from strict adherence to optimized codon usage may be made to accommodate the introduction of restriction site(s) into the resulting nucleic acid molecule.

Further to optimization of the codon usage, expression in the host cell or subject can further be improved through additional modifications of the nucleotide sequence. For example, the nucleic acid molecule of the invention can be modified so as to prevent clustering of rare, non-optimal codons being present in concentrated areas and/or to suppress or modify "negative" sequence elements which are expected to negatively influence expression levels. Such negative sequence elements include without limitation the regions having very high (>80%) or very low (<30%) GC content; AT-rich or GC-rich sequence stretches; unstable direct or inverted repeat sequences; R A secondary structures; and/or internal cryptic regulatory elements such as internal TATA-boxes, chi-sites, ribosome entry sites, and/or splicing donor/acceptor sites.

The present invention encompasses a nucleic acid molecule encoding any mycobacterial antigen selected from the group of polypeptides set forth in any of SEQ ID NO: 6-10 or any variant and fragment thereof.

The nucleic acid molecules of the present invention can be generated using sequence data accessible in the art and the sequence information provided herein. For example, they may be isolated using routine techniques well known in the art, e.g. by PCR isolation and/or cloning by conventional molecular biology from a *Mycobacterium* genome of a particular species or genomic fragment thereof, cDNA and genomic libraries or any prior art vector known to include it. Alternatively, the nucleic acid molecules of the invention can also be generated by chemical synthesis in automated process (e.g. assembled from overlapping synthetic oligonucleotides).

Another embodiment of the invention pertains to fragments of the nucleic acid molecules of the invention, e.g. restriction endonuclease and PCR-generated fragments. Such fragments can be used as probes, primers or fragments encoding relevant immunogenic portion(s).

In other aspects, the disclosure features a composition comprising a polypeptide comprising an amino acid sequence, or fragment thereof, coding for an Ag85B antigen from a *Mycobacterium* species, a polypeptide comprising an amino acid sequence, or fragment thereof, coding for a PPE68 antigen from a *Mycobacterium* species, a polypeptide comprising an amino acid sequence, or fragment thereof, coding for a ESXA antigen from a *Mycobacterium* species, a polypeptide comprising an amino acid sequence, or fragment thereof, coding for a ESXB antigen from a *Mycobacterium* species, a polypeptide comprising an amino acid sequence, or fragment thereof, coding for an ADK antigen from a *Mycobacterium* species, or a combination thereof.

In some embodiments, the Ag85B antigen corresponds to the amino acid sequence shown as NCBI Reference Sequence NP_216402.1 (diacylglycerol acyltransferase/mycolyltransferase Ag85B). In some embodiments, the polypeptide comprising an amino acid sequence, or fragment thereof, coding for an Ag85B antigen is 50% identical to NP_216402.1. In some embodiments, the polypeptide comprising an amino acid sequence, or fragment thereof, coding for an Ag85B antigen is at least 50%, at least 55%, at least 60%, at least 65%, at least 70%, at least 75%, at least 80%, at least 85%, at least 90%, at least 95% identical to NCBI Reference Sequence NP_216402.1. In some embodiments, the polypeptide comprising an amino acid sequence, or fragment thereof, coding for an Ag85B antigen is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Reference Sequence NP_216402.1. NCBI Reference Sequence NP_216402.1 amino acid sequence is shown below as SEQ ID NO. 6.

SEQ ID NO. 6

```
  1 mtdvsrkira wgrrlmigta aavvlpglvg laggaataga fsrpglpvey lqvpspsmgr 61 dikvqfqsgg nnspavylld glraqddyng wdintpafew yyqsglsivm pvggqssfys 121 dwyspacgka gcqtykwetf ltselpqwls anravkptgs aaiglsmags samilaayhp 181 qqfiyagsls alldpsqgmg psliglamgd aggykaadmw gpssdpawer ndptqqipkl 241 vanntrlwvy cgngtpnelg ganipaefle nfvrssnlkf qdaynaaggh navfnfppng 301 thsweywgaq lnamkgdlqs slgag
```

In some embodiments, the PPE68 antigen corresponds to the amino acid sequence shown as NCBI Reference Sequence YP_178022.1 (PPE family protein PPE68). In some embodiments, the polypeptide comprising an amino acid sequence, or fragment thereof, coding for a PPE68 antigen is 50% identical to YP_178022.1. In some embodiments, the polypeptide comprising an amino acid sequence, or fragment thereof, coding for a PPE68 antigen is at least 50%, at least 55%, at least 60%, at least 65%, at least 70%, at least 75%, at least 80%, at least 85%, at least 90%, at least 95% identical to NCBI Reference Sequence YP_178022.1. In some embodiments, the polypeptide comprising an amino acid sequence, or fragment thereof, coding for a PPE68 antigen is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Reference Sequence YP_178022.1. NCBI Reference Sequence YP_178022.1 amino acid sequence is shown below as SEQ ID NO. 7.

```
                                                              SEQ ID NO. 7
  1 mlwhamppel ntarlmagag papmlaaaag wqtlsaalda qaveltarln slgeawtggg 61 sdkalaaatp mvvwlqtast qaktramqat aqaaaytqam attpslpeia anhitqavlt 121 atnffginti pialtemdyf irmwnqaala mevyqaetav ntlfeklepm asildpgasq 181 sttnpifgmp spgsstpvgq lppaatqtlg qlgemsgpmq qltqplqqvt slfsqvggtg 241 ggnpadeeaa qmgllgtspl snhplaggsg psagagllra eslpgaggsl trtplmsqli 301 ekpvapsvmp aaaagssatg gaapvgagam gqgaqsggst rpglvapapl aqereedded 361 dwdeeddw
```

In some embodiments, the ESXA antigen corresponds to the amino acid sequence shown as NCBI Reference Sequence YP_178023.1 (ESAT-6 protein EsxA). In some embodiments, the polypeptide comprising an amino acid sequence, or fragment thereof, coding for a ESXA antigen is 50% identical to YP_178023.1. In some embodiments, the polypeptide comprising an amino acid sequence, or fragment thereof, coding for a ESXA antigen is at least 50%, at least 55%, at least 60%, at least 65%, at least 70%, at least 75%, at least 80%, at least 85%, at least 90%, at least 95% identical to NCBI Reference Sequence YP_178023.1. In some embodiments, the polypeptide comprising an amino acid sequence, or fragment thereof, coding for a ESXA antigen is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Reference Sequence YP_178023.1. NCBI Reference Sequence YP_178023.1 amino acid sequence is shown below as SEQ ID NO. 8.

```
                                                              SEQ ID NO. 8
  1 mteqqwnfag ieaaasaiqg nvtsihslld egkqsltkla aawggsgsea yqgvqqkwda 61 tatelnnalq nlartiseag qamastegnv tgmfa
```

In some embodiments, the ESXB antigen corresponds to the amino acid sequence shown as NCBI Reference Sequence NP_218391.1 (ESAT-6 protein EsxB). In some embodiments, the polypeptide comprising an amino acid sequence, or fragment thereof, coding for a ESXB antigen is 50% identical to NP_218391.1. In some embodiments, the polypeptide comprising an amino acid sequence, or fragment thereof, coding for a ESXB antigen is at least 50%, at least 55%, at least 60%, at least 65%, at least 70%, at least 75%, at least 80%, at least 85%, at least 90%, at least 95% identical to NCBI Reference Sequence NP_218391.1. In some embodiments, the polypeptide comprising an amino acid sequence, or fragment thereof, coding for a ESXB antigen is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Reference Sequence NP_218391.1. NCBI Reference Sequence NP_218391.1 amino acid sequence is shown below as SEQ ID NO. 9.

```
                                                       SEQ ID NO. 9
  1 maemktdaat laqeagnfer isgdlktqid qvestagslq gqwrgaagta aqaavvrfqe 61 aankqkqeld eistnirqag vqysradeeq qqalssqmgf
```

In some embodiments, the ADK antigen corresponds to the amino acid sequence shown as NCBI Reference Sequence NP_215247.1 (adenylate kinase). In some embodiments, the polypeptide comprising an amino acid sequence, or fragment thereof, coding for a ADK antigen is 50% identical to NP_215247.1. In some embodiments, the polypeptide comprising an amino acid sequence, or fragment thereof, coding for a ADK antigen is at least 50%, at least 55%, at least 60%, at least 65%, at least 70%, at least 75%, at least 80%, at least 85%, at least 90%, at least 95% identical to NCBI Reference Sequence NP_215247.1. In some embodiments, the polypeptide comprising an amino acid sequence, or fragment thereof, coding for a ADK antigen is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, identical to NCBI Reference Sequence NP_215247.1. NCBI Reference Sequence NP_215247.1 amino acid sequence is shown below as SEQ ID NO. 10.

```
                                                      SEQ ID NO. 10
  1 mrvlllgppg agkgtqavkl aeklgipqis tgelfrrnie egtklgveak ryldagdlvp 61 sdltnelvdd rlnnpdaang fildgyprsv eqakalheml errgtdidav lefrvseevl 121 lerlkgrgra ddtddvilnr mkvyrdetap lleyyrdqlk tvdavgtmde vfaralralg 181 k
```

In another embodiment, composition of the invention comprises or encodes at least 5 mycobacterial antigens showing at least 50% identity (e.g. 80%, 85%, 90%, 92%, 94%, 95%, 96%, 97%, 98%, 99% or 100% identity) with an amino acid sequence set forth herein, in over the full length polypeptide or a fragment thereof (e.g. a fragment of 30 consecutive amino acid residues or more such as 30, 40, 50, 60, 70, 75, 80 or 90 amino acid residues).

Alternatively or in addition, each of the at least five antigens from a *Mycobacterium* species may be a native mycobacterial antigen (e.g. a full length antigen) or a modified version (fragment or variant) thereof. A "native" mycobacterial antigen can be found, isolated, obtained from a source of *Mycobacterium* in nature. Such sources include biological samples (e.g. blood, plasma, sera, saliva, sputum, tissue sections, biopsy specimen etc.) collected from a subject infected or that has been exposed to a *Mycobacterium*, cultured cells as well as recombinant materials available in depositary institutions (e.g. ATCC or TB institutions), libraries or described in the literature (e.g. *Mycobacterium* isolates, *Mycobacterium* genomes, genomic fragments, genomic RNA or cDNA as well as any plasmid and vector known in the art to include such elements).

A modified mycobacterial antigen (e.g. a variant) typically differs from a polypeptide specifically disclosed herein or a native one in one or more position(s). Any modification(s) can be envisaged, including substitution, insertion, addition and/or deletion of one or more amino acid residue(s), non-natural arrangements and any combination of these possibilities. Amino acid substitution can be conservative or not. When several modifications are contemplated, they can concern consecutive residues and/or non-consecutive residues. Modification(s) can be generated by a number of ways known to those skilled in the art, such as site-directed mutagenesis, PCR mutagenesis, DNA shuffling and by synthetic techniques (e.g. resulting in a synthetic nucleic acid molecule encoding the desired polypeptide variant). Whatever their origin (native or modified), according to embodiments of the present invention, each of the mycobacterial antigens comprised in or encoded by the compositions of the invention retains one or more immunogenic portions of the corresponding native antigen including B and/or T cell epitope(s). Methods to identify such relevant immunogenic portions are well known in the art. For example, T cell epitopes can be identified by implementing biological assays (e.g. IFNg assays using libraries of synthetic overlapping oligopeptides) or available prediction programs.

Each modified mycobacterial antigen that can be envisaged in the context of the invention comprises one or more modifications with respect to the native counterpart, and especially one or more modifications which are beneficial to the synthesis, processing, stability and/or solubility of the resulting polypeptide and/or to its immunogenicity. Representative examples of suitable modifications include without limitation (a) the deletion of internal highly hydrophobic region(s), (b) the deletion of N-terminal signal peptide (replacement with heterologous ones if needed) and/or (c) the deletion of unfolded region that may interfere negatively with stability, immunogenicity and recombinant expression and/or (d) the deletion or mutation of a catalytic domain to abolish biological activity.

Vectors

The present invention also concerns vectors comprising one or more nucleic acid molecule(s) of the present invention as well as compositions comprising such vector(s).

The term "vector" as used herein refers to a vehicle, preferably a nucleic acid molecule or a viral particle that contains the elements necessary to allow delivery, propagation and/or expression of any of the nucleic acid molecule(s) described herein within a host cell or subject. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Usually plasmid vectors contain selectable marker genes that allow host cells carrying the plasmid vector to be selected for or against in the presence of a corresponding selective drug. A variety of positive and negative selectable marker genes are known in the art. By way of illustration, an antibiotic resistance gene can be used as a positive selectable marker gene that allows a host cell to be selected in the presence of the corresponding antibiotic.

Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide. The disclosure relates to any one or plurality of vectors that comprise nucleic acid sequences encoding any one or plurality of amino acid sequence disclosed herein. For the purpose of the present disclosure, the vectors may be of naturally occurring genetic sources, synthetic or artificial, or some combination of natural and artificial genetic elements.

Vectors which are appropriate in the context of the present disclosure, include, without limitation, bacteriophage, plasmid or cosmid vectors for expression in prokaryotic host cells such as bacteria (e.g. E. coli, BCG or Listeria); vectors for expression in yeast (e.g. Saccharomyces cerevisiae, Schizosaccharomyces pombe, Pichia pastoris); baculo virus vectors for expression in insect cell systems (e.g. Sf 9 cells); viral and plasmid vectors for expression in plant cell systems (e.g. Ti plasmid, cauliflower mosaic virus CaMV; tobacco mosaic virus TMV); as well as plasmid and viral vectors for expression in higher eukaryotic cells or subjects. Typically, such vectors are commercially available (e.g. in Invitrogen, Stratagene, Amersham Biosciences, Promega, etc.) or available from depositary institutions such as the American Type Culture Collection (ATCC, Rockville, Md.) or have been the subject of numerous publications describing their sequence, organization and methods of producing, allowing the artisan to apply them. Representative examples of suitable plasmid vectors include, without limitation, pREP4, pCEP4 (Invitrogen), pCI (Promega), pVAX (Invitrogen) and pGWiz (Gene Therapy System Inc). Representative examples of suitable viral vectors are generated from a variety of different viruses (e.g. retrovirus, adenovirus, adenovirus-associated virus (AAV), poxvirus, herpes virus, measles virus, foamy virus, alphavirus, vesicular stomatis virus, etc). As described above, the term "viral vector" encompasses vector DNA, genomic DNA as well as viral particles generated thereof, and especially infectious viral particles.

In some embodiments, the viral vector employed in this disclosure is replication-defective or replication-impaired which means that it cannot replicate to any significant extent in normal cells (eg. normal human cells) or in the subject to whom it is administered (the impairment or defectiveness of replication functions can be evaluated by conventional means—eg. via measuring DNA synthesis and/or viral titre in non-permissive cells). Such replication-defective or impaired vectors typically require for propagation, permissive cell lines which bring up or complement the missing/impaired functions.

Examples of viral vectors that are useful in the context of the disclosure include adenoviral vectors which have a number of well-documented advantages for vaccination, immunotherapy, gene transfer or for recombinant production (for a review, see "Adenoviral vectors for gene therapy", 2002, Ed D. Curiel and J. Douglas, Academic Press). The adenoviral vectors of the present invention can be derived from a variety of human or animal sources (e.g. canine, ovine, simian adenovirus, etc). Any serotype can be employed with a special preference for human adenoviruses and a specific preference for subgenus C such as Ad2, Ad5, Ad6, and subgenus B such as Ad11, Ad34 and Ad35. It may also be advantageous to use animal Ad with a special preference for chimp Ad, such as chimp Ad3 and Ad63. The cited adenovirus are available from ATCC or have been the subject of numerous publications describing their sequence, organization and methods of producing, allowing the artisan to apply them (see for example U.S. Pat. Nos. 6,136,594; 6,133,028; WO00/50573; WO00/70071; WO2004/083418; WO2004/097016 and WO2005/071093).

Replication-defective adenoviral vectors are E1-defective with an E1 deletion extending from approximately positions 459 to 3328 or from approximately positions 459 to 3510

(by reference to the sequence of Ad5 disclosed in the GeneBank under the accession number M 73260). The cloning capacity can further be improved by deleting additional portion(s) of the adenoviral genome (all or part of the non-essential E3 region (e.g. deletion from approximately positions 27867 to 30743) or of other essential E2 and/or E4 regions as described in WO94/28152 and Lusky et al, 1998, J. Virol 72: 2022).

The nucleic acid molecules of the present disclosure can be independently inserted in any location of the adenoviral genome, with a specific preference for insertion in replacement of the E1 and/or E3 region. They may be positioned in sense or antisense orientation relative to the natural transcriptional direction of the region in question.

Other examples of viral vectors include poxvirus vectors such as fowlpox vectors (e.g. FP9), canarypox vectors (e.g. ALVAC) and vaccinia virus vectors, the latter being preferred. Suitable vaccinia viruses include without limitation the Copenhagen strain, the Wyeth strain, NYVAC (U.S. Pat. No. 5,494,807) and the modified Ankara (MVA) strain (Antoine et al, 1998, Virol. 244: 365; WO02/42480). The general conditions for constructing and producing recombinant poxvirus are well known in the art (see for example WO2010/130753; WO03/008533; U.S. Pat. Nos. 6,998,252; 5,972,597 and 6,440,422). The nucleic acid molecules of the present invention are preferably inserted within the poxviral genome in a non-essential locus. Thymidine kinase gene is particularly appropriate for insertion in Copenhagen vaccinia vectors and deletion II or III for insertion in MVA vector (WO97/02355).

Other viral vectors are morbillivirus which can be obtained from the paramyxoviridae family, with a specific preference for measles virus. Various attenuated strains are available in the art (Brandler et al, 2008, CIMID, 31: 271; Singh et al, 1999, J. virol. 73(6): 4823), such as and without limitation, the Edmonston A and B strains (Griffin et al, 2001, Field's in Virology, 1401-1441), the Schwarz strain (Schwarz A, 1962, Am J Dis Child, 103: 216), the S-191 or C-47 strains (Zhang et al, 2009, J Med Virol. 81 (8): 1477). Insertion between P and M genes or between H and L genes is particularly appropriate.

Suitable vectors for use in the present disclosure also include bacterium cell which can be wild-type or mutant (e.g. avirulent). Well-known examples of such bacterium cells include without limitation avirulent *Mycobacterium* (e.g. *Mycobacterium bovis* BCG), *Lactobacillus* (e.g. *Lactococcus lactis*), *Listeria* (e.g. *Listeria monocytogenes*) and other microorganisms such as *Salmonella* and Pseudomona. A preferred embodiment is directed to a BCG vector into the genome of which has been incorporated nucleic acid molecule(s) encoding one or more mycobacterial antigen(s) or fusion polypeptide (s) as defined above in a manner allowing the BCG vector to express such element(s).

The present disclosure also encompasses vectors (e.g. plasmid DNA) complexed to lipids or polymers to form particulate structures such as liposomes, lipoplexes or nanoparticles.

In accordance with the present disclosure, the nucleic acid molecules comprised in the vector of the invention are in a form suitable for expression in a host cell or subject, which means that each of the nucleic acid molecules set forth herein is operably linked to appropriate regulatory sequences. As used herein, the term "regulatory elements" or "regulatory sequence" refers to any element that allows, contributes or modulates the expression of nucleic acid molecule(s) in a given host cell or subject, including replication, duplication, transcription, splicing, translation, stability and/or transport of the nucleic acid(s) or its derivative (i.e. m NA).

It will be appreciated by those skilled in the art that the choice of the regulatory sequences can depend on such factors as the vector itself, the host cell or subject, the level of expression desired, etc. The promoter is of special importance. In the context of the invention, it can be constitutive directing expression of the nucleic acid molecule in many types of host cells or specific to certain host cells (e.g. lung-specific regulatory sequences) or regulated in response to specific events or exogenous factors (e.g. by temperature, nutrient additive, hormone, etc) or according to the phase of a viral cycle (e.g. late or early). One may also use promoters that are repressed during the production step in response to specific events or exogenous factors, in order to optimize vector production and circumvent potential toxicity of the expressed polypeptide(s).

Promoters suitable for constitutive expression in mammalian cells include but are not limited to the cytomegalovirus (CMV) immediate early promoter (U.S. Pat. No. 5,168,062), the RSV promoter, the adenovirus major late promoter, the phosphoglycero kinase (PGK) promoter, the thymidine kinase (TK) promoter of herpes simplex virus (HSV)-1 and the T7 polymerase promoter. Promoters such as the trp, lac, phage promoters, tR A promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization. Vaccinia virus promoters are particularly adapted for expression in poxviral vectors. Representative example include without limitation the vaccinia 7.5K, HSR, 11K7.5 (Erbs et al., 2008, Cancer Gene Ther. 15: 18), TK, p28, p11 and K1L promoter, as well as synthetic promoters such as those described in Chakrabarti et al. (1997, Biotechniques 23: 1094-7; Hammond et al, 1997, J. Virol Methods 66: 135-8; and Kumar and Boyle, 1990, Virology 179: 151-8) as well as early/late chimeric promoters. Promoters suitable for measles-mediated expression include without limitation any promoter directing expression of measles transcription units (Brandler and Tangy, 2008, CIMID 31: 271).

Those skilled in the art will appreciate that the regulatory elements controlling the expression of the nucleic acid molecule(s) of the disclosure may further comprise additional elements for proper initiation, regulation and/or termination of transcription (e.g. polyA transcription termination sequences), mRNA transport (e.g. nuclear localization signal sequences), processing (e.g. splicing signals), and stability (e.g. introns and non-coding 5' and 3' sequences), translation (e.g. an initiator Met, tripartite leader sequences, IRES ribosome binding sites, Shine-Dalgarno sequences, etc.) into the host cell or subject and purification steps (e.g. a tag as described herein).

In some embodiments, the nucleic acid molecules encoding the mycobacterial antigens are carried by a single vector, optionally comprising a regulatory sequence operably linked to the one or more mycobacterial antigens.

In alternative embodiments, the nucleic acid molecules encoding the mycobacterial antigens are carried out by two or more vectors. Each vector encodes one or more mycobacterial antigens among those described herein. The two or more vectors can be administered to the subject substantially simultaneously, or sequentially. In some embodiments, T cells that are isolated ex vivo are exposed to two, three, four, five, six or more plasmids sequences, wherein the each of the one, two, three, four, five, six or more plasmids comprises at least one nucleic acid sequence that encodes a mycobacterial antigen. The compositions are exposed to isolated T cells (cells from a healthy subject using the steps outlined in Example) and left for a time period to stimulate an immune response against one or a plurality of antigens. In some embodiments, the T cells are CD3+/CD4+ but CD8−. In some embodiments, the T cells are CD3+/CD4+ but CD4−.

If needed, the vector of the disclosure can further comprise additional polypeptides. Exemplary additional polypeptides include without limitation immunomodulators such as cytokines and any other antigen originating from a potentially co-infecting organism.

According to one embodiment, the vector of the disclosure can be encapsulated into a viral particle or liposome or other particle (such as a pseudo-particle). In some embodiments, the viral particle is in the form of infectious, attenuated and/or non-pathogenic viral particle. Typically, such viral particles are produced by a process comprising the steps of (i) introducing the viral vector of the invention into a suitable cell line, (ii) culturing said cell line under suitable conditions so as to allow the production of said infectious viral particle, (iii) recovering the produced viral particle from the culture of said cell line, and (iv) optionally purifying said recovered viral particle. In some embodiments, the step of exposing the one or plurality of polynucleotides and/or polypeptides disclosed herein to the one or more T cells is a step free of using a viral particle.

When the viral vector is replication-defective or replication-impaired, the particles are usually produced in a permissive cell line or via the use of a helper virus, which supplies in trans the missing/impaired functions. For example, suitable cell lines for complementing E1-deleted adenoviral vectors include the 293 cells (Graham et al, 1997, J. Gen. Virol. 36: 59-72) as well as the HER-96 and PER-C6 cells (e.g. Fallaux et al, 1998, Human Gene Ther. 9: 1909-17; WO97/00326) or any derivative of these cell lines. Avian cells are particularly suitable for propagating poxvirus vectors including without limitation primary chicken embryo fibroblasts (CEF) prepared from chicken embryos obtained from fertilized eggs, and duck cell lines (e.g. as described in WO03/076601, WO2009/004016, WO2010/130756 and US2011-008872).

The infectious viral particles may be recovered from the culture supernatant and/or from the cells after lysis. They can be further purified according to standard techniques (chromatography, ultracentrifugation techniques, etc).

Host Cells and Production Methods

In other aspects, the disclosure also relates to host cells which comprise the nucleic acid molecules or vectors as described herein, as well as compositions comprising such a host cell. In some embodiments, the host cell is a T cell disclosed herein. In some embodiments, the T cell is isolated from the body of a subject. In some embodiments, the disclosure relates to a tissue culture system comprising a vessel with one or a series of walls and a surface onto which the host cells grow. In some embodiments, the tissue culture system comprises one or a plurality of host cells; and any one or plurality of polynucleotides and/or polypeptides disclosed herein. In some embodiments, the tissue culture system further comprises a heating element that encloses the vessel and air regulation device that regulates the amount of air, nitrogen, carbon dioxide and/or other gas that is exposed to the cells. In some embodiments, the tissue culture system is a closed, sterile system.

As used herein, the term "host cell" should be understood broadly without any limitation concerning particular organization in tissue, organ, or isolated cells. A "host cell" is a cell that can be used to express a nucleic acid, e.g., a nucleic acid of the disclosure, can be, but is not limited to, a eukaryotic cell, a bacterial cell, an insect cell, or a human cell. Suitable eukaryotic cells include, but are not limited to, a cell from a primary sample of PBMC, T cells, B cells, Vero cells, HeLa cells, COS cells, CHO cells, HEK293 cells, BHK cells and MDCKII cells. Suitable insect cells include, but are not limited to, Sf9 cells. The phrase "recombinant host cell" can be used to denote a host cell that has been transformed or transfected with a nucleic acid to be expressed. A host cell also can be a cell that comprises the nucleic acid but does not express it at a desired level, such as a therapeutically effective amount, unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein. A host cell also includes cells which can be or has been the recipient of the vector described herein as well as progeny of such cells.

Still a further aspect of the present invention is a method for recombinant production of the mycobacterial antigens encoded by the nucleic acids of the invention, employing the vectors (or viral particles) and/or host cells of the invention. Typically, the method comprises the steps of (i) introducing a vector into a suitable host cell to produce a transfected or infected host cell, (ii) culturing in-vitro said transfected or infected host cell under conditions suitable for growth of the host cell, (iii) recovering the cell culture, and (iv) optionally, purifying the mycobacterial antigen(s) or the fusion polypeptide from the recovered cell and/or culture supernatant.

It is expected that those skilled in the art are knowledgeable in the numerous expression systems available in the art for expressing polypeptides and of the methods for introducing a vector into a host cell. Such methods include, but are not limited to microinjection, CaPO4− mediated transfection, DEAE-dextran-mediated transfection, electroporation, lipofection/liposome fusion, gene guns, transduction, viral infection as well as direct administration into a host organism via various means. The method may also be used in association with conventional transfection reagents that facilitate introduction of nucleic acids in host cells, such as polycationic polymers (e.g. chitosan, polymethacrylate, PEI, etc) and cationic lipids (e.g. DC-Chol/DOPE, transfectam, lipofectin, etc).

Host cells can be cultured in conventional fermentation bioreactors, flasks, and petri plates. Culturing can be carried out at a temperature, pH and oxygen content appropriate for a given host cell. The recovered mycobacterial antigens can optionally be purified by well-known purification methods including ammonium sulfate precipitation, acid extraction, gel electrophoresis; filtration and chromatographic methods (e.g. reverse phase, size exclusion, ion exchange, affinity, hydrophobic-interaction, hydroxyapatite, high performance liquid chromatography, etc). The conditions and techniques to be used depend on factors such as net charge, molecular weight, hydrophobicity, hydrophilicity and will be apparent to those having skill in the art. Moreover, the level of purification will depend on the intended use. For example protein concentration can be evaluated by Bransdford assay (Biorad), endotoxin levels can be evaluated by techniques such as the Portable Test System (Charles River Laboratories) and the mass of the purified polypeptides can be measured using MALDI (Matrix-Assisted Laser Desorption/Ionisation) or electrospray methods.

Tiling

According to certain embodiments, the one or more amino acid sequences disclosed herein overlap in sequence to span part or all of the Ag85B, PPE68, ESXA, ESXB and ADK antigens.

According to one embodiment, a polypeptide comprising an amino acid sequence, or fragment thereof, coding for a first antigen from a *Mycobacterium* species and a polypeptide comprising an amino acid sequence, or fragment thereof, coding for a first antigen from a *Mycobacterium* species have amino acid sequences which overlap. In certain embodiments, a polypeptide comprising an amino acid sequence, or fragment thereof, coding for a first antigen from a *Mycobacterium* species and a polypeptide comprising an amino acid sequence, or fragment thereof, coding for a first antigen from a *Mycobacterium* species have amino acid sequences which overlap by at least 2 amino acids. According to certain embodiments, the overlap is between 2 amino acids and 23 amino acids, for example the overlap is 2, 3, 4, 5, 6, 7, 8, 9, 10, 11, 12, 13, 14, 15, 16, 17, 18, 19, 20, 21, 22 or 23 amino acids. Tiling polypeptides in this way provides broader recognition of antigen or presentation with a set of highly immunogenic peptides that span a length of one or more of the disclosed polypeptides in this disclosure.

Methods for tiling polypeptides are known in the art, and are described, for example in Harding et al., which describes the development and testing of 15 mer polypeptides, overlapping by 12 amino acids, that were tested in a human CD4+ T-cell-based proliferative assay (Molecular Cancer Therapeutics, November 2005, Volume 4, Issue 11, incorporated by reference in its entirety herein). Sticker, et al. describes a human cell-based method to identify functional CD4(+) T-cell epitopes in any protein (J Immunol Methods. 2003 Oct. 1; 281(1-2):95-108, incorporated by reference in its entirety herein).

Pepmixes utilized in the invention may be from commercially available peptide libraries made up of peptides that are about 6, 7, 8, 9, 10, 11, 12, 13, 14, or 15 amino acids long and overlapping one another by at least about 1, 2, 3, 4, 5, 6, 7, 8, 9, 10, 11 or more amino acids, in certain aspects. Examples include those from JPT technologies or Miltenyi. In particular embodiments, the peptides are 7, 8, 9, 10, 11, 12, 13, 14, 15, 16, 17, 18, 19, 20, 21, 22, 23, 24, 25, 26, 27, 28, 29, 30, 31, 32, 33, 34, or 35 or more amino acids in length, for example, and there is overlap of 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acids in length. In some embodiments, the pepmixes comprises any one or combination of: SEQ ID NO:11 through 51. Any permutation of any of those sequences is considered such that any one or plurality of such sequence identifiers may be used to elicit or stimulate an antigen-specific immune response in a cell or plurality of cells against the one or plurality of antigen fragment from which the amino acid sequences SEQ ID NO:17-59 are based.

CAR-T Compositions

In some embodiments, the invention provides an immune effector cell (e.g., T cell, NK cell) engineered to express a chimeric antigen receptor (CAR), wherein the engineered immune effector cell exhibits an anti-bacterial antigen property. A preferred antigen is a mycobacterial antigen described herein or a combination of any plurality of mycobacterial antigens disclosed herein. In one aspect, the antigen binding domain of the CAR comprises a partially humanized antibody fragment. In one aspect, the antigen binding domain of the CAR comprises a partially humanized scFv. Accordingly, the invention provides CARs that comprises a humanized antigen binding domain and is engineered into a cell, e.g., a T cell or a NK cell, and methods of their use for adoptive therapy. In some embodiments, the CARs of the invention comprise at least one intracellular domain selected from the group of a CD137 (4-1BB) signaling domain, a CD28 signaling domain, a CD27 signal domain, a CD3zeta signal domain, and any combination thereof. In one aspect, the CARs of the invention comprise at least one intracellular signaling domain is from one or more costimulatory molecule(s) other than a CD137 (4-1BB) or CD28.

Chimeric Antigen Receptor (CAR)

The present disclosure encompasses a recombinant DNA construct comprising sequences encoding a CAR, wherein the CAR comprises an antigen binding domain (e.g., antibody or antibody fragment, TCR or TCR fragment) that binds specifically to a cancer associated antigen described herein, wherein the sequence of the antigen binding domain is contiguous with and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule. The disclosure relates to compositions comprising one or a plurality of effector cells expressing a CAR specific against a mycobacterial antigen.

In one aspect, an exemplary CAR constructs comprise an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), and an intracellular stimulatory domain (e.g., an intracellular stimulatory domain described herein). In one aspect, an exemplary CAR construct comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), an intracellular costimulatory signaling domain (e.g., a costimulatory signaling domain described herein) and/or an intracellular primary signaling domain (e.g., a primary signaling domain described herein).

In one aspect, the present invention encompasses a recombinant nucleic acid construct comprising a nucleic acid molecule encoding a CAR, wherein the nucleic acid molecule comprises the nucleic acid sequence encoding an antigen binding domain, e.g., described herein, that is contiguous with and in the same reading frame as a nucleic acid sequence encoding an intracellular signaling domain.

In one aspect, the present invention encompasses a recombinant nucleic acid construct comprising a nucleic acid molecule encoding a CAR, wherein the nucleic acid molecule comprises a nucleic acid sequence encoding an antigen binding domain, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, CD27, 4-IBB, and the like. In some instances, the CAR can comprise any combination of CD3-zeta, CD28, 4-IBB, and the like. The nucleic acid sequences coding for the desired molecules can be obtained using recombinant methods known in the art, such as, for example by screening libraries from cells expressing the nucleic acid molecule, by deriving the nucleic acid molecule from a vector known to include the same, or by isolating directly from cells and tissues containing the same, using standard techniques. Alternatively, the nucleic acid of interest can be produced synthetically, rather than cloned.

The present disclosure includes retroviral and lentiviral vector constructs expressing a CAR that can be directly transduced into a cell.

The present disclosure also includes an RNA construct that can be directly transfected into a cell. A method for generating mRNA for use in transfection involves in vitro transcription (IVT) of a template with specially designed primers, followed by polyA addition, to produce a construct containing Y and 5 untranslated sequence ("UTR") (e.g., a Y and/or 5 UTR described herein), a 5 cap (e.g., a 5 cap described herein) and/or Internal Ribosome Entry Site (IRES) (e.g., an IRES described herein), the nucleic acid to be expressed, and a polyA tail, typically 50-2000 bases in length. RNA so produced can efficiently transfect different kinds of cells. In some embodiments, the template includes sequences for the CAR. In an embodiment, an RNA CAR vector is transduced into a cell, e.g., a T cell or a NK cell, by electroporation.

Antigen Binding Domain

In some embodiments, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR of the invention include those associated with *Mycobacterium* infection. In one aspect, the CAR-mediated T-cell response can be directed to an antigen of interest by way of engineering an antigen binding domain that specifically binds a desired antigen into the CAR. In one aspect, the portion of the CAR comprising the antigen binding domain comprises an antigen binding domain that targets a mycobacterial antigen, e.g., a mycobacterial antigen described herein. The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

In other aspects, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169: 1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

In one aspect, the invention provides methods for treating a disease associated with expression of a mycobacterial associated antigen described herein. In one aspect, the present invention provides methods of treating a latent or active Mycobacterial infection (i.e. an infection of any of the disclosed Mycobacterial species herein) by providing to the subject in need thereof immune effector cells (e.g., T cells, NK cells) that are engineered to express an XCAR, wherein X represents a mycobacterial antigen or functional fragment thereof as described herein, and wherein the infected cells of the subject express said X tumor antigen or functional fragment.

In one aspect, the present invention provides methods of treating a latent or active Mycobacterial infection by providing to the subject in need thereof immune effector cells (e.g., T cells, NK cells) that are engineered to express a XCAR described herein, wherein the infected cells express X. In some embodiments, X is expressed on both normal cells and bacterially infected cells, but is expressed at lower levels on normal cells. In some embodiments, the method further comprises selecting a CAR that binds X with an affinity that allows the XCAR to bind and kill the infected cells expressing X but less than 30%, 25%, 20%, 15%, 10%, 5% or less of the normal cells expressing X are killed. In some embodiments, the selected CAR has an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In some embodiments, the selected antigen binding domain has a binding affinity that is at least five-fold, 10-fold, 20-fold, 30-fold, 50-fold, 100-fold or 1,000-fold less than a reference antibody, e.g., an antibody described herein.

The disclosure includes a type of cellular therapy where immune effector cells (e.g., T cells, NK cells) are genetically modified to express a chimeric antigen receptor (CAR) and the CAR-expressing T cell or NK cell is infused to a recipient in need thereof. The infused cell is able to kill cells infected by one or more Mycobacterium in the recipient. Unlike antibody therapies, CAR-modified immune effector cells (e.g., T cells, NK cells) are able to replicate in vivo resulting in long-term persistence that can lead to sustained bacterial infection control. In various aspects, the immune effector cells (e.g., T cells, NK cells) administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell or NK cell to the patient. The invention also includes a type of cellular therapy where immune effector cells (e.g., T cells, NK cells) are modified, e.g., by in vitro transcribed RNA, to transiently express a chimeric antigen receptor (CAR) and the CAR T cell or NK cell is infused to a recipient in need thereof. The infused cell is able to kill cells infected by mycobacterium in the recipient. Thus, in various aspects, the immune effector cells (e.g., T cells, NK cells) administered to the patient, is present for less than one month, e.g., three weeks, two weeks, one week, after administration of the T cell or NK cell to the patient.

Methods of creating and making CAR effector cells are disclosed in PCT application No. PCT/US2016/052260, which is incorporated by reference in its entirety. The disclosure relates to a pharmaceutical composition comprising one or a plurality of effector cells comprising an XCAR, wherein X represents a mycobacterial antigen or functional fragment thereof as described herein, and wherein the infected cells of the subject express said X tumor antigen or functional fragment.

CD8+ T Cell Activation and Expansion

As described herein, the compositions of the present disclosure (e.g. compositions comprising a nucleic acid sequence encoding an antigen, or a functional fragment thereof, from a Mycobacterium species, compositions comprising a polypeptide comprising an amino acid sequence, or fragment thereof, coding for an antigen from a Mycobacterium species) and cells comprising the compositions of the present disclosure, are used or are capable of stimulating immune cells, including for example, cytolytic T cells (CD8+ cells), memory CD8+ T cells, T helper cells (CD4+ cells) and NK cells. In preferred embodiments, the compositions of the present disclosure are capable of stimulating CD8+ T-cells. In some embodiments, the compositions described herein are capable of stimulating more than one type of immune cell at the same time, for example, more than one of cytolytic T cells (CD8+ cells), memory CD8+ T cells and/or NK cells.

The stimulation of the immune cells may enhance normal cellular functions, or initiate normal cell functions in an abnormal cell. Accordingly, the present disclosure also provides populations of cells resulting from stimulation with the compositions described herein.

In some embodiments, stimulating the immune cells refers to expansion of the immune cells. In some embodiments, stimulating the immune cells refers to activation of the immune cells. In some embodiments, stimulating the immune cells refers to an increase in cytoxicity of the immune cells.

In certain embodiments, the compositions of the present disclosure (e.g. compositions comprising a nucleic acid sequence encoding an antigen, or a functional fragment thereof, from a Mycobacterium species, compositions comprising a polypeptide comprising an amino acid sequence, or fragment thereof, coding for an antigen from a Mycobacterium species) and cells comprising the compositions of the present disclosure, are sufficient to stimulate an immune killer cell ex vivo. In other embodiments, the compositions and cells as described herein are sufficient to stimulate an immune killer cell in vivo.

In some embodiments, the compositions and cells described herein are capable of activating CD8+ T-cells. In some embodiments, the compositions and cells described herein are capable of expanding CD8+ T-cells. In some embodiments, the compositions and cells described herein are capable of activating and expanding CD8+ T-cells.

T cell activation and expansion can be measured by various assays as described herein. For example, T cell activities that may be measured include the induction of proliferation of T cells, the induction of signaling in T cells, the induction of expression of activation markers in T cells, the induction of cytokine secretion by T cells, and the cytotoxic activity of T cells. For example, in certain embodiments, CD8+ T cell activation is measured by a proliferation assay.

Cytokine Secretion

The activation of CD8+ T-cells by compositions or cells of the disclosure may be assessed or measured by determining secretion of cytokines, such as gamma interferon (IFN-γ), tumor necrosis factor alpha (TNFa), interleukin-12 (IL-12) or interleukin 2 (IL-2). In some embodiments, ELISA is used to determine cytokine secretion, for example secretion of gamma interferon (IFN-γ), tumor necrosis factor alpha (TNFa), interleukin-12 (IL-12) or interleukin 2 (IL-2). The ELISPOT (enzyme-linked immunospot) technique may be used to detect T cells that secrete a given cytokine (e.g., gamma interferon (IFN-γ)) in response to stimulation with the compositions described herein. T cells are cultured with the compositions or cells comprising the compositions described herein in wells which have been coated with anti-IFN-γ antibodies. The secreted IFN-γ is captured by the coated antibody and then revealed with a second antibody coupled to a chromogenic substrate. Thus, locally secreted cytokine molecules form spots, with each spot corresponding to one IFN-γ-secreting cell. The number of spots allows one to determine the frequency of IFN-γ-secreting cells in the analyzed sample. The ELISPOT assay has also been described for the detection of tumor necrosis factor alpha, interleukin-4 (IL-4), IL-5, IL-6, IL-10, IL-12, granulocyte-macrophage colony-stimulating factor, and granzyme B-secreting lymphocytes (Klinman D, Nutman T. Current protocols in immunology. New York, N.Y: John Wiley & Sons, Inc.; 1994. pp. 6.19.1-6.19.8, incorporated by reference in its entirety herein).

Flow cytometric analyses of intracellular cytokines may be used to measure the cytokine content in culture supernatants, but provides no information on the number of T cells that actually secrete the cytokine. When T cells are treated with inhibitors of secretion such as monensin or brefeldin A, they accumulate cytokines within their cytoplasm upon activation (e.g. with composition of the present invention). After fixation and permeabilization of the lymphocytes, intracellular cytokines can be quantified by cytometry. This technique allows the determination of the cytokines produced, the type of cells that produce these cytokines, and the quantity of cytokine produced per cell.

Cytotoxicity

The activation of CD8+ T-cells by compositions or cells comprising the compositions as described herein may be assessed by assaying the cytotoxic activity of the CD8+ T-cells.

The cytotoxic activity of T cells may be assessed by any suitable technique known to those of skill in the art. For example, a sample comprising T cells that have been exposed to the compositions or cells comprising the compositions as described herein can be assayed for cytotoxic activity after an appropriate period of time, in a standard cytotoxic assay. Such assays may include, but are not limited to, the chromium release CTL assay and the Alamar Blue™ fluorescence assay known in the art.

Proliferation/Expansion

The ability of the compositions or cells as described herein to expand T cells can be evaluated by using CFSE staining. Compositions or cells as described herein are mixed with CD8+ T cells (e.g. from a subject suffering from a disease or disorder, such as a Mycobacterial infection). To compare the initial rate of cell expansion, the cells are subject to CFSE staining to determine how well the compositions or cells comprising the compositions as described herein induced the proliferation of T cells. CFSE staining provides a much more quantitative endpoint and allows simultaneous phenotyping of the expanded cells. Every day after stimulation, an aliquot of cells is removed from each culture and analyzed by flow cytometry. CFSE staining makes cells highly fluorescent. Upon cell division, the fluorescence is halved and thus the more times a cell divides the less fluorescent it becomes. The ability of the compositions or cells comprising the compositions as described herein to induce T cell proliferation is quantitated by measuring the number of cells that divided once, twice, three times and so on. The compositions or cells comprising the compositions as described herein that induce the greatest number of cell divisions at a particular time point is deemed as the most potent expander.

To determine how well these compositions or cells as described herein promote long-term growth of T cells, cell growth curves can be generated. These experiments are set up as the foregoing CFSE experiments, but no CFSE is used. Every 2-3 days of culture, T cells are removed from the respective cultures and counted using a Coulter counter which measures how many cells are present and the mean volume of the cells. The mean cell volume is the best predicator of when to restimulate the cells. In general, when T cells are properly stimulated they triple their cell volume. When this volume is reduced to more than about half of the initial blast, it may be necessary to restimulate the T cells to maintain a log linear expansion (Levine et al., 1996, Science 272:1939-1943; Levine et al., 1997, J. Immunol. 159:5921-5930). The time it takes the compositions or cells comprising the compositions as described herein to induce 20 population doublings is calculated. The relative differences of various compositions or cells comprising the compositions as described herein to induce this level of T cell expansion is an important criteria on which a composition or cell comprising the composition is assessed.

In addition, the phenotypes of the cells expanded by the compositions or cells comprising the compositions as described herein can be characterized to determine whether a particular subset is preferentially expanded. Prior to each restimulation, a phenotype analysis of the expanding T cell populations is performed to define the differentiation state of the expanded T cells using the CD27 and CD28 definitions proposed by Appay et al. (2002, Nature Med. 8, 379-385, incorporated by reference in its entirety herein) and CCR7 definitions proposed by Sallusto et al. (1999, Nature 401: 708-712, incorporated by reference in its entirety herein). Perforin and Granzyme B intracellular staining can be used to perform a gross measure to estimate cytolytic potential.

Apoptosis Markers

In certain embodiments of the present invention, stimulation, activation, and expansion of T cells using the compositions or cells as described herein enhances expression of certain key molecules in T cells that protect again apoptosis or otherwise prolong survival in vivo or in vitro. Apoptosis usually results from induction of a specific signal in the T cell. Thus, the compositions or cells comprising the compositions as described herein may provide for protecting a T cell from cell death resulting from stimulation of the T cell. Therefore, also included in the present invention is the enhanced T cell growth by protection from premature death or from absence or depletion of recognized T cell growth markers, such as Bcl-xL, growth factors, cytokines, or lymphokines normally necessary for T cell survival, as well as from Fas or Tumor Necrosis Factor Receptor (TNFR) cross-linking or by exposure to certain hormones or stress.

Cells Expressing an Antigen from a *Mycobacterium* Species

In one aspect the disclosure provides a cell or plurality of cells comprising the compositions disclosed herein (e.g. compositions comprising a nucleic acid sequence encoding an antigen, or a functional fragment thereof, from a *Mycobacterium* species, compositions comprising a polypeptide comprising an amino acid sequence, or fragment thereof, coding for an antigen from a *Mycobacterium* species).

In some embodiments, the compositions of the present disclosure comprise one or more cells, wherein said cells comprise at least one of the mycobacterial antigens described herein. In some embodiments, said one or more cells comprise at least two antigens from a *Mycobacterium* species. In some embodiments, said one or more cells comprise at least three antigens from a *Mycobacterium* species. In some embodiments, said one or more cells comprise at least four antigens from a *Mycobacterium* species. In some embodiments, said one or more cells comprise at least five antigens from a *Mycobacterium* species. In some embodiments, the cell comprise at least two, three, four or five antigens from a *Mycobacterium* species, that are different from each other (e.g. multiple copies of the same mycobacterial antigen can be used provided that the combination comprises/encodes at least 5 different mycobacterial antigens).

In one aspect, the disclosure features a cell or plurality of cells comprising one or a combination of (i) a nucleic acid sequence encoding an Ag85B antigen at least 50% identical to SEQ ID NO. 1, a nucleic acid sequence encoding a PPE68 antigen at least 50% identical to SEQ ID NO. 2, a nucleic acid sequence encoding a ESXA antigen at least 50% identical to SEQ ID NO. 3, a nucleic acid sequence encoding an ESXB antigen at least 50% identical to SEQ ID NO. 4, a nucleic acid sequence encoding an ADK antigen at least 50% identical to SEQ ID NO. 5, or a combination thereof;

(ii) a polypeptide comprising an amino acid sequence coding for an Ag85B antigen at least 50% identical to SEQ ID NO. 6, a polypeptide comprising an amino acid sequence coding for an PPE68 antigen at least 70% identical to SEQ ID NO. 7, a polypeptide comprising an amino acid sequence coding for an ESXA antigen at least 50% identical to SEQ ID NO. 8, a polypeptide comprising an amino acid sequence coding for an ESXB antigen at least 50% identical to SEQ ID NO. 9, a polypeptide comprising an amino acid sequence coding for an ADK antigen at least 50% identical to SEQ ID NO. 10, or a combination thereof; (iii) a nucleic acid of (i), encoding a functional fragment of a nucleic acid sequence of SEQ ID NO. 1, SEQ ID NO. 2, SEQ ID NO. 3, SEQ ID NO. 4 or SEQ ID NO. 5; and (iv) an amino acid sequence of (ii), encoding a functional fragment of an amino acid sequence of SEQ ID NO. 6, SEQ ID NO. 7, SEQ ID NO. 8, SEQ ID NO.9 or SEQ ID NO. 10.

In some embodiments, the cell is a helper (CD4+) T-cell.

In some embodiments, the cell is a cytotoxic (CD8+) T-cell.

In some embodiments, the cell is a Gamma/Delta T-cell.

In some embodiments, the cell is a central memory T-cell.

In some embodiments, the cell is an effector memory T-cell.

In some embodiments, helper T-cells comprise between about 60% to about 90% of the total T-cell population, about 60% to about 80%, about 60% to about 70%, about 70% to about 80%, about 70% to about 90%, about 80% to about 90% of the total T-cell population. In a further embodiment, helper T-cells may comprise about 60%, about 65%, about 70%, about 75%, about 80%, about 85% or about 90%, of the total T-cell population. Helper T-cells can be identified as CD45+CD3+CD4+ cells. Identification can be carried out, for example, by flow cytometry.

In some embodiments, cytotoxic T-cells comprise between about 0% to about 40% of the total T-cell population, about 0% to about 30%, about 0% to about 20%, about 0% to about 10%, about 10% to about 20%, about 10% to about 30%, about 10% to about 40%, about 20% to about 40%, about 30% to about 40% of the total T-cell population. In a further embodiment, cytotoxic T-cells may comprise about 0%, about 5%, about 10%, about 15%, about 20%, about 25%, about 30%, about 35%, or about 40%, of the total T-cell population. Cytotoxic T-cells can be identified as CD45+CD3+CD8+ cells. Identification can be carried out, for example, by flow cytometry.

In some embodiments, Gamma/Delta T-cells comprise between about 0.5% to about 10% of the total T-cell population, about 0.5% to about 5%, about 0.5% to about 1%, about 1% to about 5%, about 1.5% to about 5%, about 2% to about 5%, about 3% to about 5%, about 4% to about 5% of the total T-cell population. In a further embodiment, Gamma/Delta T-cells may comprise about 0.5%, about 1%, about 1.5%, about 2%, about 2.5%, about 3%, about 3.5%, about 4%, about 4.5%, about 5%, about 6%, about 7%, about 8%, about 9% or about 10% of the total T-cell population. Gamma/Delta T-cells can be identified as CD45+CD3+CD4−CD8−TCRgd+ cells. Identification can be carried out, for example, by flow cytometry.

In some embodiments, central memory T-cells comprise between about 0.5% to about 15% of the total T-cell population, about 0.5% to about 10%, about 0.5% to about 5%, about 0.5% to about 1%, about 1% to about 15%, about 1% to about 10%, about 1% to about 5%, about 5% to about 15%, about 5% to about 10%, about 10% to about 15% of the total T-cell population. In a further embodiment, central memory T-cells may comprise about 0.5%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14% or about 15% of the total population. Central memory T-cells can be identified as CD45+CD3+CD45RA−CCR7+ cells. Identification can be carried out, for example, by flow cytometry.

In some embodiments, effector memory T-cells comprise between about 20% to about 60% of the total T-cell population, about 20% to about 50%, about 20% to about 40%, about 20% to about 30%, about 30% to about 60%, about 30% to about 50%, about 30% to about 40%, about 40% to about 60%, about 40% to about 50%, about 50% to about 60% of the total T-cell population. In a further embodiment, effector memory T-cells may comprise about 20%, about 25%, about 30%, about 35%, about 40%, about 45%, about 50%, about 55%, or about 60%, of the total T-cell population. Effector memory T-cells can be identified as CD45+CD3+CD45RA−CCR7− cells. Identification can be carried out, for example, by flow cytometry.

In some embodiments, the plurality of cells comprise CD4+ T-cells and CD8+ T-cells, wherein the number of CD8+T-cells is greater than the number of CD4+ T-cells. For example, In some embodiments, the number of CD8+T-cells is 1-fold greater than the number of CD4+ T-cells; In some embodiments, the number of CD8+T-cells is 2-fold greater than the number of CD4+ T-cells; In some embodiments, the number of CD8+T-cells is 3-fold greater than the number of CD4+ T-cells; In some embodiments, the number of CD8+ T-cells is 4-fold greater than the number of CD4+ T-cells; In some embodiments, the number of CD8+T-cells is 5-fold greater than the number of CD4+ T-cells; In some embodiments, the number of CD8+T-cells is 6-fold greater than the number of CD4+ T-cells; In some embodiments, the number of CD8+ T-cells is 7-fold greater than the number of CD4+ T-cells; In some embodiments, the number of CD8+T-cells is 8-fold greater than the number of CD4+ T-cells; In some embodiments, the number of CD8+T-cells is 9-fold greater than the number of CD4+ T-cells; In some embodiments, the number of CD8+T-cells is 10-fold greater than the number of CD4+ T-cells.

In some embodiments, the cell is from a human subject. In a further embodiment, the human subject is immunocompromised. In another embodiment, the human subject has been diagnosed or is suspected of having a Mycobacterial infection.

In some embodiments, the cell or plurality of cells are expanded in cell culture. In some embodiments, the cell culture comprises at least one primary T-cell.

In some embodiments, the cell or plurality of cells is an antigen-presenting cell, a peripheral blood mononuclear cell, a cord blood cell, a purified population of T cells, and a T cell line, a B-cell, a monocytes, a dendritic cell, a Phytohemagglutinin blast, or an artificial antigen presenting cell based on immortalized cells such as K562 or other cell lines.

In some embodiments, the cell is an antigen presenting cell (APC). In a further embodiments, the APC is an artificial antigen presenting cell.

In some embodiments, the cell is a macrophage.

In some embodiments, the cell is a dendritic cell.

In certain embodiments, the cell is capable of expressing a polypeptide comprising an amino acid sequence, or fragment thereof, coding for an Ag85B antigen from a *Mycobacterium* species, a polypeptide comprising an amino acid sequence, or fragment thereof, coding for a PPE68 antigen from a *Mycobacterium* species, a polypeptide comprising an amino acid sequence, or fragment thereof, coding for a ESXA antigen from a *Mycobacterium* species, a polypeptide comprising an amino acid sequence, or fragment thereof, coding for a ESXB antigen from a *Mycobacterium* species, a polypeptide comprising an amino acid sequence, or fragment thereof, coding for an ADK antigen from a *Mycobacterium* species, or a combination thereof. In some embodiments, the disclosure relates to a cell or plurality of cells comprising one or a combination of: (i) a nucleic acid sequence encoding an Ag85B antigen at least 50% identical to SEQ ID NO. 1, a nucleic acid sequence encoding a PPE68 antigen at least 50% identical to SEQ ID NO. 2, a nucleic acid sequence encoding a ESXA antigen at least 50% identical to SEQ ID NO. 3, a nucleic acid sequence encoding an ESXB antigen at least 50% identical to SEQ ID NO. 4, a nucleic acid sequence encoding an ADK antigen at least 50% identical to SEQ ID NO. 5, and/or a combination thereof;

(ii) a polypeptide comprising an amino acid sequence coding for an Ag85B antigen at least 50% identical to SEQ ID NO. 6, a polypeptide comprising an amino acid sequence coding for an PPE68 antigen at least 50% identical to SEQ ID NO. 7, a polypeptide comprising an amino acid sequence coding for an ESXA antigen at least 50% identical to SEQ ID NO. 8, a polypeptide comprising an amino acid sequence coding for an ESXB antigen at least 50% identical to SEQ ID NO. 9, a polypeptide comprising an amino acid sequence coding for an ADK antigen at least 50% identical to SEQ ID NO. 10, and/or a combination thereof;

(iii) a nucleic acid of (i), encoding a functional fragment of a nucleic acid sequence of SEQ ID NO. 1, SEQ ID NO. 2, SEQ ID NO. 3, SEQ ID NO. 4 or SEQ ID NO. 5; and/or (iv) an amino acid sequence of (ii), encoding a functional fragment of an amino acid sequence of SEQ ID NO. 6, SEQ ID NO. 7, SEQ ID NO. 8, SEQ ID NO.9 or SEQ ID NO. 10.

In some embodiments, the disclosure relates to a cell or plurality of cells comprising one or a combination of: (i) a nucleic acid sequence encoding an Ag85B antigen at least 50% identical to SEQ ID NO. 17-59, a nucleic acid sequence encoding a PPE68 antigen at least 50% identical to SEQ ID NO. 17-59, a nucleic acid sequence encoding a ESXA antigen at least 50% identical to SEQ ID NO. 17-59, a nucleic acid sequence encoding an ESXB antigen at least 50% identical to SEQ ID NO. 17-59, a nucleic acid sequence encoding an ADK antigen at least 50% identical to SEQ ID NO. 17-59, and/or a combination thereof; In some embodiments, the disclosure relates to an isolated cell or plurality of cells exposed to or stimulated by one or a combination of: (i) a nucleic acid sequence encoding an Ag85B antigen at least 50% identical to SEQ ID NO. 17-59, a nucleic acid sequence encoding a PPE68 antigen at least 50% identical to SEQ ID NO. 17-59, a nucleic acid sequence encoding a ESXA antigen at least 50% identical to SEQ ID NO. 17-59, a nucleic acid sequence encoding an ESXB antigen at least 50% identical to SEQ ID NO. 17-59, a nucleic acid sequence encoding an ADK antigen at least 50% identical to SEQ ID NO. 17-59, and/or a combination thereof; and/or (ii) a nucleic acid sequence encoding an Ag85B antigen at least 50% identical to SEQ ID NO. 1, a nucleic acid sequence encoding a PPE68 antigen at least 50% identical to SEQ ID NO. 2, a nucleic acid sequence encoding a ESXA antigen at least 50% identical to SEQ ID NO. 3, a nucleic acid sequence encoding an ESXB antigen at least 50% identical to SEQ ID NO. 4, a nucleic acid sequence encoding an ADK antigen at least 50% identical to SEQ ID NO. 5, and/or a combination thereof; and/or (iii) a polypeptide comprising an amino acid sequence coding for an Ag85B antigen at least 50% identical to SEQ ID NO. 6, a polypeptide comprising an amino acid sequence coding for an PPE68 antigen at least 50% identical to SEQ ID NO. 7, a polypeptide comprising an amino acid sequence coding for an ESXA antigen at least 50% identical to SEQ ID NO. 8, a polypeptide comprising an amino acid sequence coding for an ESXB antigen at least 50% identical to SEQ ID NO. 9, a polypeptide comprising an amino acid sequence coding for an ADK antigen at least 50% identical to SEQ ID NO. 10, and/or a combination thereof; and/or (iv) a nucleic acid of (ii), encoding a functional fragment of a nucleic acid sequence of SEQ ID NO. 1, SEQ ID NO. 2, SEQ ID NO. 3, SEQ ID NO. 4 or SEQ ID NO. 5; and/or (v) an amino acid sequence of (iii), encoding a functional fragment of an amino acid sequence of SEQ ID NO. 6, SEQ ID NO. 7, SEQ ID NO. 8, SEQ ID NO.9 or SEQ ID NO. 10.

Cells Engineered to Expand T-Cells

In one aspect, the present disclosure provides a cell engineered to expand T-cells ex vivo, wherein the cell comprises at least two antigens selected from Ag85B, PPE68, ESXA, ESXB and ADK, wherein the cell is produced by a process comprising introducing one or more nucleic acids, each encoding one or more of the at least two antigens, into the cell; and culturing the cell under conditions suitable for production of one or more of the antigens. In some embodiments, one or a plurality of host cells are free of any exogenous DNA and/or RNA and/or polypeptides except for the those polypeptides or nucleic acid sequences introduced for eliciting or stimulating an immune response or clonal expansion of the cells.

In one aspect, the present disclosure provides a cell engineered to expand T-cells ex vivo, wherein the cell comprises at least three antigens selected from Ag85B, PPE68, ESXA, ESXB and ADK, wherein the cell is produced by a process comprising introducing one or more nucleic acids, each encoding one or more of the at least three antigens, into the cell; and culturing the cell under conditions suitable for production of one or more of the antigens.

In one aspect, the present disclosure provides a cell engineered to expand T-cells ex vivo, wherein the cell comprises at least four antigens selected from Ag85B, PPE68, ESXA, ESXB and ADK, wherein the cell is produced by a process comprising introducing one or more nucleic acids, each encoding one or more of the at least four antigens, into the cell; and culturing the cell under conditions suitable for production of one or more of the antigens.

In one aspect, the present disclosure provides a cell engineered to expand T-cells ex vivo, wherein the cell comprises at least five antigens selected from Ag85B, PPE68, ESXA, ESXB and ADK, wherein the cell is produced by a process comprising introducing one or more nucleic acids, each encoding one or more of the at least 5 antigens, into the cell; and culturing the cell under conditions suitable for production of one or more of the antigens.

In some embodiments, the cell is an antigen-presenting cell, a peripheral blood mononuclear cell, a cord blood cell, a purified population of T cells, and a T cell line, a B-cell, a monocytes, a dendritic cell, a Phytohemagglutinin blast, or an artificial antigen presenting cell based on immortalized cells such as K562 or other cell lines.

In some embodiments, the nucleic acid nucleic acid comprises DNA or RNA. In some embodiments, the introducing step comprises viral transduction. In another embodiment, the introducing step comprises electroporation.

Sources of T Cells

In certain embodiments, prior to expansion, a source of T cells is obtained from a subject. Non-limiting examples of subjects include humans, dogs, cats, mice, rats, and transgenic species thereof. In some embodiments, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In some embodiments, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, In some embodiments, a concentration of 2 billion cells/ml is used. In some embodiments, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, the population of cells may include peripheral blood mononuclear cells, cord blood cells, a purified population of T cells, and a T cell line. In another embodiment, the population of cells to be electroporated comprises peripheral blood mononuclear cells. In yet another embodiment, the population of cells to be electroporated comprises purified T cells.

Expansion of T Cells

In some embodiments, the disclosure relates to a composition comprising a T cell comprising one or more nucleic acids, each encoding one or more of the at least 2, 3, 4, or 5 antigens. The invention also includes a population of expanded T cells comprising one or more nucleic acids, each encoding one or more of the at least 2, 3, 4, or 5 antigens. In some embodiments, the one or more nucleic acids are introduced into at least one of the population of cells and expressed on the surface of the cells. The invention also includes a population of expanded T cells comprising one or more nucleic acids, each encoding one or more of the at least 1, 2, 3, 4, or 5 antigens chosen from any one of combination of: SEQ ID NO:17 through SEQ ID NO:59. In any set of embodiments, the methods or compositions disclosed herein comprise exposure or stimulation of isolated T cells to any one, individually of combination of two or more: SEQ ID NO:17 through SEQ ID NO:59.

In some embodiments, the source of the T cells to be expanded is peripheral blood mononuclear cells (PMBCs).

In some embodiments, the T cells are expanded by contact with a polypeptide comprising an amino acid sequence, or fragment thereof, coding for an Ag85B antigen from a *Mycobacterium* species, a polypeptide comprising an amino acid sequence, or fragment thereof, coding for a PPE68 antigen from a *Mycobacterium* species, a polypeptide comprising an amino acid sequence, or fragment thereof, coding for a ESXA antigen from a *Mycobacterium* species, a polypeptide comprising an amino acid sequence, or fragment thereof, coding for a ESXB antigen from a *Mycobacterium* species, a polypeptide comprising an amino acid sequence, or fragment thereof, coding for an ADK antigen from a *Mycobacterium* species, or a combination thereof.

In some embodiments, the T cells are expanded by contact with an antigen presenting cell, wherein the antigen presenting cell presents expressing an amino acid sequence, or fragment thereof, coding for an Ag85B antigen from a *Mycobacterium* species, a polypeptide comprising an amino acid sequence, or fragment thereof, coding for a PPE68 antigen from a *Mycobacterium* species, a polypeptide comprising an amino acid sequence, or fragment thereof, coding for a ESXA antigen from a *Mycobacterium* species, a polypeptide comprising an amino acid sequence, or fragment thereof, coding for a ESXB antigen from a *Mycobacterium* species, a polypeptide comprising an amino acid sequence, or fragment thereof, coding for an ADK antigen from a *Mycobacterium* species, or a combination thereof.

In some embodiments, the present disclosure comprises a method of expanding a population of T cells (e.g. one or a plurality of isolated T-cells) comprising culturing the population, wherein the T cells contained within the population expand at least about 10 fold. In some embodiments, the T cells contained within the population expand at least about 5 fold, 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In some embodiments, the T cells expand in the range of from about 5 fold to about 100 fold.

Following culturing, the T cells can be incubated in cell medium in a culture apparatus for a period of time sufficient to reach or until the cells reach confluency or high cell density for optimal passage before passing the cells to another culture apparatus. The culturing apparatus can be any culture apparatus commonly used for culturing cells in vitro. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In some embodiments, the method further comprises cryopreserving the cultured T cells.

The cells can be further expanded using a method described in U.S. Pat. No. 5,199,942 (incorporated herein by reference). Expansion, such as described in U.S. Pat. No. 5,199,942 can be in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-2, IL-3 and c-kit ligand, for example as those described in Dudley et al., J. Immunol., 26(4):332-342, 2003, for a Rapid Expansion Protocol (REP).

In some embodiments, the methods for expanding T-cells ex vivo comprise stimulating the one or plurality of T-cells with one or more cytokines before after or contemporaneously with contact to the nucleic acid encoding and/or the amino acids coding for the mycobacterial antigens or functional fragments disclosed herein. Exemplary cytokines include, but are not limited to, IL-4, IL-7, IL-21, IFNα, IL-15 and TGFβ. In some embodiments, each of the cytokines is a human variant or human sequence of the encoded aforementioned polypeptides.

In some embodiments, IL-4 corresponds to GenBank Accession No. AAH70123.1, shown below as SEQ ID NO. 11.

```
                                                          SEQ ID NO. 11
  1 mgltsqllpp lffllacagn fvhghkcdit lqeiiktlns lteqktlcte ltvtdifaas 61 knttteketfc raatvlrqfy shhekdtrcl gataqqfhrh kqlirflkrl drnlwglagl 121 nscpvkeanq stlenflerl ktimrekysk css
```

In some embodiments, IL-7 corresponds to GenBank Accession No. AAH47698.1, shown below as SEQ ID NO. 12.

```
                                                          SEQ ID NO. 12
  1 mfhvsfryif glpplilvll pvassdcdie gkdgkqyesv lmvsidqlld smkeigsncl 61 nnefnffkrh icdankegmf lfraarklrq flkmnstgdf dlhllkvseg ttillnctgq 121 vkgrkpaalg eaqptkslee nkslkeqkkl ndlcflkrll qeiktcwnki lmgtkeh
```

In some embodiments, IL-21 corresponds to GenBank Accession No. BBA22643.1, shown below as SEQ ID NO. 13.

```
                                                          SEQ ID NO. 13
  1 mrsspgnmer iviclmvifl gtlvhksssq gqdrhmirmr qlidivdqlk nyvndlvpef 61 lpapedvetn cewsafscfq kaqlksantg nneriinvsi kklkrkppst nagrrqkhrl 121 tcpscdsyek kppkeflerf ksllqkmihq hlssrthgse ds
```

In some embodiments, IL-15 corresponds to GenBank Accession No. AAI00964.1, shown below as SEQ ID NO. 14.

```
                                                          SEQ ID NO. 14
  1 mriskphlrs isiqcylcll lnshflteag ihvfilgcfs aglpkteanw vnvisdlkki 61 edliqsmhid atlytesdvh psckvtamkc fllelqvisl esgdasihdt venliilann 121 slssngnvte sgckeceele eknikeflqs fvhivqmfin ts
```

In some embodiments, IFNα corresponds to GenBank Accession No. AAA52724.1, shown below as SEQ ID NO. 15.

```
                                                          SEQ ID NO. 15
  1 mallfpllaa lvmtsyspvg slgcdlpqnh gllsrntlvl lhqmrrispf lclkdrrdfr 61 fpqemvkgsq lqkahvmsvl hemlqqifsl fhterssaaw nmtlldqlht elhqqlqhle 121 tellqvvgeg esagaisspa ltlrryfqgi rvylkekkys dcawevvrme imkslflstn 181 mqerlrskdr dlgss
```

In some embodiments, TGFβ corresponds to GenBank Accession No. AAA36738.1, shown below as SEQ ID NO. 16.

```
                                                          SEQ ID NO. 16
  1 mhvrslraaa phsfvalwap lfllrsalad fsldnevhss fihrrlrsqe rremqreils 61 ilglphrprp hlqgkhnsap mfmldlynam aveegggpgg qgfsypykav fstqgpplas 121 lqdshfltda dmvmsfvnlv ehdkeffhpr yhhrefrfdl skipegeavt aaefriykdy 181 irerfdnetf risvyqvlqe hlgresdlfl ldsrtlwase egwlvfdita tsnhwvvnpr 241 hnlglqlsve tldgqsinpk lagligrhgp qnkqpfmvaf fkatevhfrs irstgskqrs 301 qnrsktpknq ealrmanvae nsssdqrqac kkhelyvsfr dlgwqdwiia pegyaayyce 361 gecafplnsy mnatnhaivq tlvhfinpet vpkpccaptq lnaisvlyfd dssnvilkky 421 rnmvvracgc h
```

In one aspect, the method of expanding the T cells can further comprise a culturing step. The culturing step can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition or conditions sufficient for the establishing a culture of the cells of interest—to sustain the viability of one or a plurality of the cells and proliferate or grow number of cells outside of the subject. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In some embodiments, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. In some embodiments, the target cells are maintained under conditions necessary to support growth, for example, an appropriate temperature (e.g., 37° C.) and atmosphere (e.g., air plus 5% CO2).

The medium used to culture the T cells may include an agent that can co-stimulate the T cells. For example, an agent that can stimulate CD3 is an antibody to CD3, and an agent that can stimulate CD28 is an antibody to CD28.

In certain embodiments, particular populations of T-cells are isolated. For example, In some embodiments, the T-cell populations are selected from helper T-cells, cytotoxic T-cells, gamma/delta T-cells, central memory T-cells and/or effector memory T-cells.

In some embodiments, helper T-cells can be identified as CD45+CD3+CD4+ cells. Identification can be carried out, for example, by flow cytometry. In some embodiments, cytotoxic T-cells can be identified as CD45+CD3+CD8+ cells. Identification can be carried out, for example, by flow cytometry. In some embodiments, Gamma/Delta T-cells can be identified as CD45+CD3+CD4−CD8−TCRgd+ cells. Identification can be carried out, for example, by flow cytometry. In some embodiments, central memory T-cells can be identified as CD45+CD3+CD45RA−CCR7+ cells. Identification can be carried out, for example, by flow cytometry. In some embodiments, effector memory T-cells can be identified as CD45+CD3+CD45RA-CCR7− cells. Identification can be carried out, for example, by flow cytometry. The disclosure relates to compositions, including pharmaceutical compositions comprising any one or plurality of cells disclosed herein in a pharmaceutically effective amount necessary to treat or prevent *Mycobacterium* infection in a subject. In some embodiments, the pharmaceutically effective amount Therapy The compositions of the present disclosure (e.g. compositions comprising a nucleic acid sequence encoding an antigen, or a functional fragment thereof, from a *Mycobacterium* species, compositions comprising a polypeptide comprising an amino acid sequence, or fragment thereof, coding for an antigen from a *Mycobacterium* species) or pharmaceutical compositions described herein may be used for various therapies.

In certain embodiments, the compositions of the present disclosure (e.g. compositions comprising a nucleic acid sequence encoding an antigen, or a functional fragment thereof, from a *Mycobacterium* species, compositions comprising a polypeptide comprising an amino acid sequence, or fragment thereof, coding for an antigen from a *Mycobacterium* species) or pharmaceutical compositions described herein are used in treating a *Mycobacterium* infection or any disease and pathologic condition caused by or associated with it, in a subject in need thereof. In certain embodiments, the compositions of the present disclosure (e.g. compositions comprising a nucleic acid sequence encoding an antigen, or a functional fragment thereof, from a *Mycobacterium* species, compositions comprising a polypeptide comprising an amino acid sequence, or fragment thereof, coding for an antigen from a *Mycobacterium* species) or pharmaceutical compositions described herein mare used in preventing a *Mycobacterium* infection or any disease and pathologic condition caused by or associated with it, in a subject tin need thereof. Such uses aim at inducing or stimulating protective immune responses against a mycobacterial antigen/epitope. The disclosure relates to methods of treating and/or preventing a *Mycobacterium* infection comprising administering to a subject one or a plurality of host cells stimulated by one or a plurality of compositions disclosed herein. The disclosure relates to methods of treating and/or preventing a *Mycobacterium* infection comprising administering to a subject at therapeutically effective amount of cells stimulated by one or a plurality of compositions disclosed herein.

In some embodiments, the *Mycobacterium* infection is an active infection. An active infection refers to a *Mycobacterium* infection with manifested serious disease symptoms. For example, in a human subject, TB is characterized by general clinical signs (such as weight loss, asthenia, fever, night sweats), clinical signs and/or symptoms (such as cough, hemoptysis, thoracic pain in case of pulmonary TB), and/or in some cases extrapulmonary signs according to the sites of infection (such as lymph nodes, bone forms, meningitis, urologenital forms).

In some embodiments, the subject is an immunocompromised host. In embodiments of the present disclosure, an immunocompromised host refers to a subject with either a congenital or acquired defect in adaptive or innate immunity (including but not limited to primary immunodeficiency disorders, patients undergoing chemotherapy or immunosuppressive therapy, or patients undergoing hematopoietic stem cell transplantation). In further embodiments, the immunocompromised host has been diagnosed as having, or suspected of having, infection with a *Mycobacterium* species.

In another embodiment, the subject to be treated may be a newborn, an infant, a young adult or an adult. The subject may have been previously treated for a *Mycobacterium* infection before being treated with the compositions or cells described herein. The subject may or may not be co-infected with another pathogenic organism (e.g. the human immunodeficiency virus HIV). In some embodiments, the method of treatment may reduce the overall infection of within the subject by about 10% of the detectable levels of mycobacterial DNA within the subject. In some embodiments, the treatment reduce the overall infection within the subject to subclinical levels.

In some embodiments, the method or methods are used to prevent or delay infection in a subject who has been in close contact with an infected individual having developed an active disease and thus at risk of developing a *Mycobacterium* infection (e.g. transmission by inhalation of bacilli in moist droplets coughed out by the individual with TB).

In some embodiments, methods of preventing or delaying infection are carried out in a latently infected subject. By a latently infected subject is meant an individual, who is already infected with a virulent *Mycobacterium* species (e.g. Mtb), but shows no manifested disease symptoms or clinical signs. Typically, the latently-infected subject retains the *Mycobacterium* within his bodies, is not clinically ill but retains a risk of subsequent progression to clinical disease (reactivation), particularly in the context of immunosuppression (e.g. co-infection with another pathogen such as HIV or under immunosuppressive treatment such as TNFa inhibitors). A Mtb latently-infected subject will be expected to be positive if tested by any test permitting the diagnosis of a Mtb infection (e.g. tuberculin test, Mantoux test for PPD reactivity, and/or IFNg release assays).

In some embodiments, the disclosure features a method for stimulating a T cell-mediated immune response in a subject in need thereof, the method comprising administering to the subject a therapeutically effective amount of the compositions of the present disclosure (e.g. compositions comprising a nucleic acid sequence encoding an antigen, or a functional fragment thereof, from a *Mycobacterium* species, compositions comprising a polypeptide comprising an amino acid sequence, or fragment thereof, coding for an antigen from a *Mycobacterium* species) or pharmaceutical compositions described herein.

In some embodiments, the disclosure includes a method for adoptive cell transfer therapy. The method comprises administering an expanded population of cells comprising T cells to a subject in need thereof to prevent or treat a Mycobacterial infection. In this embodiment, the expanded population of cells is expanded as described herein. The expanded T cells generated as described herein are uniform and possess T cell function.

In some embodiments, the induced or stimulated immune response is specific (i.e. directed to a mycobacterial epitopes/antigen). In the context of the disclosure, the immune response is preferably a CD4+ or CD8+-mediated T-cell response, or both, directed to a mycobacterial antigen/epitope.

In certain embodiments, the T-cell response is characterized by activation of a combination (one or more) of particular T-cell populations. For example, the T-cell response may be characterized by activation of helper T-cells, cytotoxic T-cells, gamma/delta T-cells, central memory T-cells and/or effector memory T-cells, wherein each particular T-cell population comprises a percent of the total T-cell population.

In some embodiments, helper T-cells comprise between about 60% to about 90% of the total T-cell population, about 60% to about 80%, about 60% to about 70%, about 70% to about 80%, about 70% to about 90%, about 80% to about 90% of the total T-cell population. In a further embodiment, helper T-cells may comprise about 60%, about 65%, about 70%, about 75%, about 80%, about 85% or about 90%, of the total T-cell population. Helper T-cells can be identified as CD45+CD3+CD4+ cells. Identification can be carried out, for example, by flow cytometry.

In some embodiments, cytotoxic T-cells comprise between about 0% to about 40% of the total T-cell population, about 0% to about 30%, about 0% to about 20%, about 0% to about 10%, about 10% to about 20%, about 10% to about 30%, about 10% to about 40%, about 20% to about 40%, about 30% to about 40% of the total T-cell population. In a further embodiment, cytotoxic T-cells may comprise about 0%, about 5%, about 10%, about 15%, about 20%, about 25%, about 30%, about 35%, or about 40%, of the total T-cell population. Cytotoxic T-cells can be identified as CD45+CD3+CD8+ cells. Identification can be carried out, for example, by flow cytometry.

In some embodiments, Gamma/Delta T-cells comprise from about 0.5% to about 10% of the total T-cell population, about 0.5% to about 5%, about 0.5% to about 1%, about 1% to about 5%, about 1.5% to about 5%, about 2% to about 5%, about 3% to about 5%, about 4% to about 5% of the total T-cell population. In a further embodiment, Gamma/Delta T-cells may comprise about 0.5%, about 1%, about 1.5%, about 2%, about 2.5%, about 3%, about 3.5%, about 4%, about 4.5%, about 5%, about 6%, about 7%, about 8%, about 9% or about 10% of the total T-cell population. Gamma/Delta T-cells can be identified as CD45+CD3+CD4−CD8−TCRgd+ cells. Identification can be carried out, for example, by flow cytometry.

In some embodiments, central memory T-cells comprise between about 0.5% to about 15% of the total T-cell population, about 0.5% to about 10%, about 0.5% to about 5%, about 0.5% to about 1%, about 1% to about 15%, about 1% to about 10%, about 1% to about 5%, about 5% to about 15%, about 5% to about 10%, about 10% to about 15% of the total T-cell population. In a further embodiment, central memory T-cells may comprise about 0.5%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14% or about 15% of the total T-cell population. Central memory T-cells can be identified as CD45+CD3+CD45RA−CCR7+ cells. Identification can be carried out, for example, by flow cytometry.

In some embodiments, effector memory T-cells comprise between about 20% to about 60% of the total T-cell population, about 20% to about 50%, about 20% to about 40%, about 20% to about 30%, about 30% to about 60%, about 30% to about 50%, about 30% to about 40%, about 40% to about 60%, about 40% to about 50%, about 50% to about 60% of the total T-cell population. In a further embodiment, effector memory T-cells may comprise about 20%, about 25%, about 30%, about 35%, about 40%, about 45%, about 50%, about 55%, or about 60%, of the total T-cell population. Effector memory T-cells can be identified as CD45+CD3+CD45RA−CCR7− cells. Identification can be carried out, for example, by flow cytometry.

The ability of the compositions and cells described herein to induce or stimulate an immune response can be evaluated either in vitro or in vivo using a variety of direct or indirect assays which are standard in the art.

Evaluation of cellular immunity can be estimated for example by an increased frequency in immune cells such as T lymphocytes specific for at least one of the mycobacterial antigens comprised in or encoded by the immunogenic combination and fusion polypeptide described herein. One may also monitor cell proliferation upon radioactive labelling (e.g. T cell proliferation assays by [3H] thymidine incorporation assay). Another and sensitive method for detecting the immune response is ELISpot in which the frequency of IFNg-producing cells is determined. Cytotoxic capacity for antigen-specific T lymphocytes can also be evaluated in a sensitized subject or by immunization of appropriate animal models. It is also possible to proceed by quantification of the release of relevant Th1 and/or Th2 cytokine(s) produced by activated T cells using routine bioassays (e.g. by multiparameters flow cytometry (ICS), by cytokine profile analysis using multiplex technologies or ELISA, etc.). PCR techniques can also be used to determine the presence of mRNA coding for the relevant cytokines. It will be appreciated by a skilled person that a significant increase or decrease in the amount of such relevant cytokines can be used to assess the immunogenic activity of one or more of the active agent(s) described herein.

The protective immune response can be evaluated in vivo in appropriate experimental animal, e.g. a mouse, a rat or a guinea pig (see Ashwin et al, 2008, Am J Resp, 39: 503-8; Acosta et al, 2011, Malays J Med, 18: 5-12), e.g. by measuring a reduction in mycobacterial colony-forming unit (cfu) from the spleen, lung or other tissue homogenates isolated from the animals which have received a challenge infection with a virulent strain of a *Mycobacterium* species (e.g. Mtb) after previously having been immunized with one or more of the compositions described herein, as compared to the mycobacterial cfu in a control group of experimental animals infected with the same virulent strain of *Mycobacterium*, but which have not previously been immunized. The comparison between treated and non-treated groups can also be assessed on animal survival (an increased survival in the treated group will correlate with a protective immune response).

Such immunological read outs are good correlates of protective immune response against a *Mycobacterium* infection provided by the active agent(s) described herein.

In other aspects, the T cells described herein may be included in a composition for therapy. The composition may include a pharmaceutical composition and further include a pharmaceutically acceptable carrier. A therapeutically effective amount of the pharmaceutical composition comprising the T cells may be administered.

In another embodiment, the T cells described herein may be used for the manufacture of a medicament for the treatment of an immune response in a subject in need thereof.

The cells of the present disclosure can be administered to an animal, preferably a mammal, even more preferably a human, to treat a mycobacterial infection.

Cells of the disclosure can be administered in dosages and routes and at times to be determined in appropriate preclinical and clinical experimentation and trials. Cell compositions may be administered multiple times at dosages within these ranges. Administration of the cells of the disclosure may be combined with other methods useful to treat the desired disease or condition as determined by those of skill in the art.

The cells of the disclosure to be administered may be autologous, allogeneic or xenogenic with respect to the subject undergoing therapy.

The administration of the cells of the disclosure may be carried out in any convenient manner known to those of skill in the art. The cells of the present disclosure may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the disclosure are injected directly into a site of inflammation in the subject, a local disease site in the subject, a lymph node, an organ, a tumor, and the like.

The cells described herein can also be administered using any number of matrices. The present disclosure utilizes such matrices within the novel context of acting as an artificial lymphoid organ to support, maintain, or modulate the immune system, typically through modulation of T cells. Accordingly, the present disclosure can utilize those matrix compositions and formulations which have demonstrated utility in tissue engineering. Accordingly, the type of matrix that may be used in the compositions, devices and methods of the disclosure is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present disclosure is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current disclosure is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Pharmaceutical Compositions

The disclosure relates to pharmaceutical compositions comprising (i) a pharmaceutically effective amount of the compositions described herein (e.g. compositions comprising a nucleic acid sequence encoding an antigen, or a functional fragment thereof, from a *Mycobacterium* species, compositions comprising a polypeptide comprising an amino acid sequence, or fragment thereof, coding for an antigen from a *Mycobacterium* species—or combinations of both); and (ii) a pharmaceutically acceptable carrier. The disclosure also relates to a pharmaceutical composition comprising (i) a pharmaceutically effective amount of one or a plurality of cells as described herein; and (ii) a pharmaceutically acceptable carrier. Pharmaceutical compositions of the present disclosure may comprise an expanded T cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

The composition of the disclosure is suitably buffered in order to be appropriate for human or animal use at a physiological or slightly basic pH (e.g. from approximately pH 7 to approximately pH 9). Suitable buffers include without limitation phosphate buffer (e.g. PBS), bicarbonate buffer and/or Tris buffer.

The composition of the disclosure can further comprise a diluent appropriate for human or animal use. It is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Wiliams & Wilkins).

Additional pharmaceutically acceptable excipients may be used for providing desirable pharmaceutical or pharmacodynamic properties, including for example modifying or maintaining the pH, osmolarity, viscosity, clarity, colour, sterility, stability, rate of dissolution of the formulation, modifying or maintaining release or absorption into an the human or animal organism, promoting transport across the blood barrier or penetration in a particular organ (e.g. lung).

In addition, the composition of the disclosure may comprise one or more adjuvant(s) suitable for systemic or mucosal application in humans. Preferably, the adjuvant is capable of stimulating immunity to the composition of the disclosure, especially a T cell-mediated immunity e.g. through the toll-like receptors (TLR), such as TLR-7, TLR-8 and TLR-9. Representative examples of useful adjuvants include without limitation alum, mineral oil emulsion such as Freunds complete and incomplete (IF A), lipopolysaccharide or a derivative thereof (Ribi et al, 1986, Immunology and Immunopharmacology of Bacterial Endotoxins, Plenum Publ. Corp., NY, p407-419), saponins such as QS21 (WO 98/56415), imidazo-quinoline compounds such as Imiquimod (WO2007/147529), cytosine phosphate guanosine oligodeoxynucleotides such as CpG and cationic peptides such as IC-31 (Kritsch et al, 2005, J. Chromatogr Anal. Technol Biomed Life Sci 822: 263) or any derivative thereof.

The pharmaceutically acceptable vehicles included in the composition of the disclosure must also permit to preserve its stability under the conditions of manufacture and long-term storage (i.e. at least one month with a preference for at least one year) at freezing (e.g. −70° C., −20° C.), refrigerated (e.g. 4° C.), ambient temperatures. Such "long term" formulations are known in the art (e.g. WO98/02522; WO03/053463). One may cite (a) 1M saccharose, 150 mM NaCl, ImM MgCl2, 54 mg/l Tween 80, 10 mM Tris pH 8.5, (b) 10 mg/ml mannitol, 1 mg/ml HSA, 20 mM Tris, pH 7.2, and 150 mM NaCl and (c) physiological saline which are particularly adapted to the composition of the disclosure.

The composition of the disclosure can be in various forms, e.g. solid, liquid or frozen. Solid (e.g. dry powdered or lyophilized) compositions can be obtained by a process involving vacuum drying and freeze-drying. In a specific embodiment, the composition of the disclosure is formulated for delivery in the respiratory tract (e.g. by inhalation, intranasal or intrapulmonary route) in a spray-dried (see e.g. WO2010/135495) or droplet form (with a specific preference for droplets having an average diameter of 100-5000 µm).

Any of the conventional administration routes are applicable in the context of the disclosure including systemic, topical or mucosal routes. In some embodiments, the pharmaceutical composition is administered intravenously in a bag in fluid communication with the subject. In some embodiments, a purified population of one or more of activated T cells are Systemic administration includes for example subcutaneous, intradermal, intramuscular, intravenous, intraperitoneal, intravascular, intraarterial injection as well as scarification. Injections can be made with conventional syringes and needles, or any other appropriate devices available in the art (e.g. electroporation). Mucosal administration includes without limitation oral/alimentary, intranasal, intratracheal, intrapulmonary, intravaginal or intra-rectal route. Administration in the respiratory tract can be performed through nebulisation or aerosolization of droplet, spray, or dry powdered compositions using appropriate dispenser. Topical administration can also be performed using transdermal means (e.g. patch and the like). Intramuscular, intradermal and subcutaneous routes are particularly preferred in the context of the disclosure as well as intranasal intratracheal and intrapulmonary administrations.

The appropriate dosage can be adapted as a function of various parameters, in particular the active agent(s) comprised in the composition, the mode of administration; the age, health, and weight of the subject; the nature and extent of symptoms; kind of concurrent treatment; the frequency of treatment; and/or the need for prevention or therapy. Further refinement of the calculations necessary to determine the appropriate dosage for treatment is routinely made by a practitioner, in the light of the relevant circumstances.

In certain embodiments, a pharmaceutical composition comprising the expanded T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present disclosure, and reinfuse the patient with these activated and expanded T cells. This process can be carried out multiple times every few weeks. In certain embodiments, T cells can be activated from blood draws of from 10 ml to 400 ml. In certain embodiments, T cells are activated from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

In certain embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities. In further embodiments, the T cells of the disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. The dosage of the above treatments to be administered to a patient will vary with the precise nature of the condition being treated and the recipient of the treatment. The scaling of dosages for human administration can be performed according to art-accepted practices.

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the disclosure, and, as such, may be considered in making and practicing the invention. Particularly useful techniques for particular embodiments will be discussed in the sections that follow.

All of the references, patent applications, or other documents listed in this application and the Examples section are herein incorporated by reference in their entireties.

EXAMPLES

Example 1

Generation and Transfection of Dendritic Cells for CTL Stimulation (Prophetic)

Stimulation of peripheral blood (PB) T cells with mature dendritic cells (DC) expressing mycobacterial antigen can lead to reactivation of antigen-specific cytotoxic T lymphocytes (CTL). DC can be differentiated from adherent PB mononuclear cells (PBMC) by culture in GM-CSF and IL-4. Antigen(s) will be introduced into DCs by transfection with DNA plasmids encoding the disclosed antigens and the DCs can then be matured by culture in a cytokine cocktail containing IL-1, IL-6, TNFα, and PGE-2. In this example, an exemplary procedure is provided for preparing and transfecting dendritic cells as a component required for the generation of therapeutic T cells. The specimen in certain embodiments may comprise heparinized peripheral blood from subject or donor (or previously frozen PBMC). Infectious disease testing may have been performed within 7 days of blood collection.

Preparation of PBMCs from fresh blood will be performed (if using cryopreserved blood, proceed as described below). Dilute heparinized peripheral blood (ideally 60 ml) in an equal volume of D-PBS or RPMI 1640 at ambient (room) temperature. In a 50 ml centrifuge tube, carefully overlay approximately 10 ml Lymphoprep with approximately 20 ml of diluted blood. Adjust as necessary to utilize all the available cells. Centrifuge at 400×G for 40 minutes at ambient temperature. Save 3×1 ml plasma aliquots and store at −80° C. Harvest PBMC interface into an equal volume of D-PBS or RPMI 1640. Centrifuge at 450×G for 10 minutes at ambient temperature. Aspirate supernatant. Loosen pellet by "finger-flicking" and resuspend in 20 mL of D-PBS or RPMI 1640. Remove 20 µl of cells. Add 20 µl of 50% red cell lysis buffer and count using a hemacytometer.

For preparation of previously frozen PBMCs, cells will be thawed at 37° C., diluted in 10 mL of warm CellGenix DC medium per 1 mL of frozen cells, and counted. For DC initiation, we will proceed as follows: calculate the number of 35 mm wells of a 6 well plate(s) seeded at ~10×10$^6$ PBMC per plate (range 7 to 14×10$^6$) to use all available PBMC. Centrifuge at 400×G for 5 minutes at ambient temperature. Resuspend cells in 2 mLs per plate to be seeded. Cells will be transferred to 37° C./5% CO$_2$ incubator for two hours to adhere DC precursors. Wells will be rinsed three times with 10 mLs of D-PBS or RPMI, combining the supernatants containing the PBMC non-adherent fraction. To the remaining adherent cells, add 2 mLs of DC culture medium containing 1000 units per ml of IL-4 and 800 units per ml of GM-CSF per well. Return flasks/plate(s) to 37° C., 5% CO$_2$ incubator. If not previously cryopreserved, non-adherent cells may be cryopreserved for future use responder T cells.

Immature DC will be fed as follows. On day 3 or 4, replenish IL-4 to 1000 units per mL and GM-CSF to 800 units per ml. Make up CellGenix medium containing 20×GM-CSF and IL-4 and add 100 µpî per well. At maturation of DC, harvest immature DC on day 5 or 6 by gentle resuspension (by now there should only be a few cells adhering to the flask). To remove remaining adherent cells, add 5 mLs of cold D-PBS for approximately 1 minute and gently resuspend and combine with immature DC. Cell count will be performed using a hemacytometer. using only large dendritic cells. Resuspended DCs at 2×10$^6$ per mL in CellGenix medium and aliquot 1 mL per well of a 24 well plate. Sterile water will be added to unused wells. 1 mL of DC culture medium containing the cytokine maturation cocktail will be added to the well to yield a cytokine final concentration of: GM-CSF 800U/ml; IL-4 1000 U/ml; TNF-α 10 ng/ml; PGE-11 µg/mL; IL-Iβ 10 ng/ml; IL-6 100 ng/ml DC Cells will be incubated for 20-28 h in 37° C., 5% CO$_2$ incubator. Harvest 24h-mature DC after 20-28 h by gentle resuspension with a 3 mL transfer pipette. Cells will be counted using hemacytometer. For transfection of dendritic cells, 4 ml of Cell Genix media will be pre-warmed in a 6 well plate in a 37° C./5% CO$_2$ incubator. Harvested dendritic cells will be divided in 3 (Tube 1-3) 15 mL centrifugation tubes. DC cell number/tube will not be lower than 0.5×10$^6$ and higher than 2×10$^6$. DCs will be centrifuged for 10 min at 200 g. We will aspirate supernatant and add DNA plasmids to DC pellet in a final concentration of 5 µg per plasmid per tube each plasmid corresponding to and encoding one, two, three, four or more mycobacterial antigens disclosed herein. Resuspended DCs and DNA with 100 µl of transfection reagent, mix well and transfer to the nucleofection cuvettes. Cuvettes will be placed into the Nucleofector, choose program U2 and the nucleofection will be started by pressing the start button. After Nucleofection immediately add 500 µl of the pre-warmed Media to the cuvette and the cells will be transferred to a 37° C./5% CO$_2$ incubator. After 10 minutes in the incubator the cells will be transferred to a 12-well tissue culture treated plate and add 1.5 ml of DC culture medium containing the cytokine maturation cocktail with Cytokine Final Concentration of: GM-CSF at 800 U/ml; IL-4 at 1000 U/ml; TNF-α at 10 ng/ml; PGE-1 at 1 µg/ml; IL-1β at 10 ng/ml; and IL-6 at 100 ng/ml The DCs will then be incubated for 12-18 h at 37° C. in 5% CO$_2$ incubator. DCs will be harvested and irradiated for use as APCs with T cell populations. After harvesting and counting, the DCs will be irradiated for use as APCs with 30 Gy. Then they will be washed once with 10 mL of medium, resuspended at 2 or 1×10$^5$ per mL with CTL culture medium.

Example 2

Generation of Antigen-Specific Cytotoxic T-Lymphocytes (CTLS) Using Plasmid Nucleofected Dendritic Cells The present example concerns exemplary manufacturing of antigen specific cytotoxic lymphocytes. This procedure may be used to prepare cells for protocols that use plasmid nucleofected DCs as antigen-presenting cells. In certain cases, DCs are nucleofected with plasmids encoding the mycobacterial antigens or functional fragments provided herein.

Antigen-specific cytotoxic T cell lines (CTLs) will be generated by stimulation of peripheral blood mononuclear cells (PBMC) with autologous antigen-presenting cells (APC) expressing the antigens from a DNA plasmid encoding the mycobacterial antigens. The APC are the dendritic cells (DC), in certain embodiments of the invention. Dendritic cells are potent APCs that can be efficiently nucleofected and are used to generate virus-specific T cells from patients. In certain embodiments, plasmid-nucleofected dendritic cells can be used for second or subsequent stimulations. Under the culture conditions employed, outgrowing T cell lines should contain T cells specific for the antigens of interest (CMV-IE1 and pp65, Adenovirus antigens and EBV antigens). Cytokines (IL-4 and IL-7) are added at the first stimulation. Heparinized peripheral blood will be used from the patient, or previously frozen patient PBMCs. Infectious disease testing may be performed within 7 days (depending on specific protocol) of blood collection. Plasmid nucleofected dendritic cells (DC) are prepared from the patient or donor.

One may calculate the final expanded T cell numbers as required. Sufficient cells are required for patient doses and QC testing according to the patient's body surface area, predicted dose levels and whether additional doses are allowed. In certain embodiments, one allows for the chance that the patient may be enrolled on a higher dose level than expected. DCs should be prepared in CellGenix medium to ensure that they are free of fetal calf serum antigens, in particular cases. CTL initiation will be performed in the presence of FCS.

Preparation of mononuclear "responder" cells from fresh blood will be performed by diluting heparinized peripheral blood (for example, 60 ml) in an equal volume of D-PBS or RPMI 1640 at ambient (room) temperature. In a 50 ml centrifuge tube, carefully overlay approximately 10 ml Lymphoprep with approximately 20 ml of diluted blood. Adjust as necessary to utilize all the available cells. Centrifuge at 400×G for 40 minutes at ambient temperature. Save 3×1 ml plasma aliquots and store at −80° C. Harvest PBMC interface into an equal volume of D-PBS or RPMI 1640. Sample will be centrifuged at 450×G for 10 minutes at room temperature. Supernatant will then be aspirated. Cell pellet will be loosened by "finger-flicking" and resuspended in 20 mL of D-PBS or RPMI 1640. Remove 20 µl of cells. Add 20 µl of 50% red cell lysis buffer and count using a hemacytometer. If appropriate, one can then proceed to PBMC stimulation by dendritic cells in plates or bioreactors.

Preparation of CTLs from previously frozen PBMCs or nonadherent mononuclear cells may be performed, if necessary. Cells will be thawed at 37° C., dilute in 10 mL of warm medium per 1 mL of frozen cells and then counted.

In appropriate situations, one can proceed to PBMC stimulation by dendritic cells, for example in plates or in bioreactors as mentioned in Example 1. PBMCs will be centrifuged at 400×G for 5 minutes at room temperature and then supernatant will be removed. Cells will be resuspended at $2×10^6$ cells per mL in CTL media+IL4 (1000 U/ml–final concentration) and IL-7 (10 ng/ml–final concentration). 1 mL aliquots of cells per well will be transferred to a 24 well and return plate to incubator or aliquoted from about 5 to about 7.5 mL (10 to $15×10^6$) PBMCs in a GP40 bioreactor and returned to the incubator. We will obtain prepared plasmid nucleofected DCs, irradiated with 30 Gy and washed 4 times. Antigen presenting cells will be resuspended at $2×10^5$ to $1×10^5$ (DC) cells/ml for a 10:1 or 20:1 ratio of PBMC to DC. 1 ml aliquots of DCs will be placed into PBMC wells, or 7.5 mL of DCs into Bioreactor and add medium for a total of 30 mL of medium and we will culture the cells at 37° C. in 5% $CO_2$ in air for 7 days. On Day 7: If there are $<3×10^6$ cells/well perform a one-half media change. Remove ~1 mL of medium per well and replace with ~1 mL of fresh CTL medium+cytokines. On Day 7: If there are $>3×10^6$ cells/well split and feed CTL; transfer ~1 mL of CTL to new well; feed with ~1 mL of fresh CTL medium+cytokines. On Day 7: If there are $<50×10^6$ cells in bioreactor remove 10 ml media and replenish with fresh media+cytokines. On Day 7: If there are $>50×10^6$ cells in bioreactor transfer 15 ml CTL to new bioreactor and replenish both with fresh media+cytokines. Culture for additional 4-6 days. For clinical cryopreservation, when sufficient cells have been obtained, cryopreserve and characterize cells. Within one week of freezing CTLs, cytotoxicity assays should be set up with $5×10^6$-$1×10^7$ cells and phenotyping should be done with an additional $2×10^6$ cells according to specific protocol requirements.

In certain embodiments, there will be therapeutically effective amount of CTLs for infusion of the cells into the patient at the appropriate dose level (determined at that time) and for all QC requirements; <10% killing of recipient PHA blasts at 20:1 (if allogeneic); and <2% CD 83+/CD3 cells (exclusion of DC).

Example 3

SOP: Manufacturing Mycobacteria-Specific CTL

1. Purpose 1.1 Patients with T-cell immunodeficiency often have suspectibility to invasive mycobacterial infections.
1.2 Mycobacteria-specific T cells can be expanded from healthy donors. 1.3 The purpose of this procedure is to provide a means of manufacturing mycobacteria-specific T cells targeting a range of antigens: AG85B, PPE68, ESXB, P9WNK7, and ADK.
1.4 Overlapping peptides (Pepmixes) of mycobacterial antigens will be used to stimulate T cells.
1.5.1 Pepmixes are comprised of peptides with 15 amino acids overlapping by 11 amino acids covering the entire length of the proteins of interest.

2. Policies

1 This procedure is to be followed by trained GMP and QA/QC staff.
2.2 This procedure may be used to prepare cells for protocols that use Pepmix-pulsed PBMC as antigen-presenting cells (APCs).
2.3 Dates are approximate and are +/−3 days to account for weekends and holidays unless specified.
2.4 Cell counts and viability must be performed using validated and established assays such as Trypan Blue. However, equivalent assays or equipment may be used once qualified.

3. Abbreviations and Definitions 3.1 MST Mycobacteria-specific T Lymphocytes
3.2 Pepmix Overlapping 15mer peptide library 3.3 QC Quality Control
3.4 GMP Good Manufacturing Practices
3.5 CETI Program for Cell Enhancement and Technologies for Immunotherapy
3.6 FDA Food and Drug Administration
3.7 PBMC Peripheral Blood Mononuclear Cells
3.8 IND Investigational New Drug
3.9 DC Dendritic Cell
3.10 SOP Standard Operating Procedure
3.11 PI Principal Investigator
3.12 QA Quality Assurance
3.13 PBS Phosphate Buffered Saline
3.14 CTL Medium 45% EHAA Click's, 45% advanced RPMI, 10% HI FBS or HS, 2 mM GlutaMAX
3.15 CoA Certificate of Analysis
3.16 HS Human Serum
3.17 HI Heat Inactivated
3.18 IL Interleukin
3.19 CNMC Children's National Medical Center
3.20 APC Antigen-presenting Cell
3.21 g Gravity
3.22 C. Celsius
3.23 CO2 Carbon Dioxide
3.24 BSC Biological Safety Cabinet
3.25 HSA Human Serum Albumin (Flexbumin)

4. Specimens 4.1 Heparanized peripheral blood from the patient/donor, previously frozen patient PBMC.
4.1.1 Infectious disease testing must be performed according to federal regulations.

5. Materials and Equipment 5.1 Materials
  5.1.1 RPMI 1640 Invitrogen
  5.1.2 Advanced RPMI 1640 Invitrogen
  5.1.3 EHAA Click's Irvine Scientific
  5.1.4 HI Fetal Calf Serum HyClone
  5.1.5 Human serum Gemini Bio Products
  5.1.6 GlutaMAX (200 mM) Invitrogen
  5.1.7 Tissue Culture Plates Corning
  4.2.8 Gas permeable cultureware Wilson Wolf
  4.2.9 Interleukin-4 R&D systems
  4.2.10 Interleukin-7 R&D systems
  4.2.11 Centrifuge tubes Corning
  4.2.12 Serological pipets Falcon
  4.2.13 Lymphoprep Nycomed
  4.2.14 PBS Invitrogen
  4.2.15 Red cell lysis buffer Becton Dickinson
  4.2.16 Dendritic cell medium CellGenix
  4.2.17 Pipette tips ART
  4.2.18 Plasma transfer set Charter Medical
  4.2.19 Syringes Becton Dickinson
  4.2.20 Pepmixes JPT
5.2 Equipment
NOTE: All materials in contact with cells must be sterile, pyrogen-free, and stored and used according to the manufacturer's directions unless stated otherwise. Equivalent materials and equipment may be used with approval of QA but all changes must be recorded on the appropriate worksheets.
  5.2.1 Biological Safety Cabinet (certified)
  5.2.2 Microscope
  5.2.3 Centrifuge
  5.2.4 Incubator
  5.2.5 Irradiator
  5.2.6 Hemacytometer
  5.2.7 Water Bath
  5.2.8 Pipet Aid 5.2.9 LS selection magnet 6. Procedure 6.1 Production of Mycobacteria-specific T-cells from healthy donors:
  6.1.1 Preparation of PBMC from fresh blood (for frozen PBMCs, proceed to frozen PBMC step below)
    6.1.1.1 Dilute heparinized peripheral blood in an equal volume of PBS or RPMI 1640 at ambient temperature.
    6.1.1.2 In a 50 mL centrifuge tube, carefully overlay approximately 10-15 mL Lymphoprep with approximately 30 mL of diluted blood.
    6.1.1.3 Centrifuge at 800×g for 20 minutes or 400×g for 40 minutes at ambient temperature with acceleration and brake at level 1.
    6.1.1.4 Save 1 mL plasma aliquot(s) (if applicable) and store at −80° C.
    6.1.1.5 Harvest PBMC interface into an equal volume of PBS or RPMI 1640.
    6.1.1.6 Centrifuge at 450×g for 10 minutes at ambient temperature. Aspirate supernatant.
    6.1.1.7 Loosen pellet and resuspend cells in a volume of PBS or RPMI 1640 that will yield an estimated 1×106 cells/mL.
    6.1.1.8 Remove sample of cells for counting. Dilute sample with trypan blue or red cell lysis buffer and count using a hemacytometer according to SOP. A qualified cell counter may also be used.
    6.1.1.9 Proceed to activation step below
  6.1.2 Preparation of responder cells from previously frozen PBMCs
    6.1.2.1 Thaw cells at 37° C., dilute in −10 mL of warm medium per 1 mL of frozen cells according to SOP M02.
    6.1.2.2 Count according to SOP.
    6.1.2.3 Proceed to activation step below for CTL initiation in bioreactor
  6.1.3 Fresh/previously frozen PBMC activation in bioreactors using viral pepmixes.
    6.1.3.1 Centrifuge ~1.5×107 PBMC/tube at 400×g for 5 minutes at ambient temperature.
    6.1.3.2 Take 1 vial of Pepmix mastermix (5 ul at 40 ng/uL, containing all targeted mycobacterial pepmixes equally mixed by volume and concentration) and dilute in 200 uL CTL medium making 1 ng/uL.
    6.1.3.3 Remove supernatant from PBMCs and pulse with 100 uL of the diluted Pepmix Mastermix (100 ng/peptide) for approximately 30-60 minutes at 37° C., 5% CO2.
    6.1.3.4 Resuspend Pepmix-pulsed PBMC in 30 mL of CTL media containing 6 uL IL-4 (400 U/ml final concentration) and 30 uL IL-7 (10 ng/mL final concentration).
    6.1.3.5 Transfer to one G-Rex bioreactor per 1.5×107 cells and return to incubator.
  6.1.4 Day 3-4: Optional feed
    6.1.4.1 Add 6 uL IL-4 (stock=2000 U/ml, final 400U/ml) and 30 uL IL-7 (stock=10 ng/ul, final concentration 10 ng/ml) to each Grex-10.
    6.1.4.2 Return Grex bioreactors to incubator.
  6.1.5 Day 6-8: T-cell feed
    6.1.5.1 Remove 15 mL of media from each Grex-10 without disturbing cells.

6.2.5.2 Resuspend cells and perform a cell count per SOP.
6.1.5.3 If there are >5.0×107 cells in GRex, transfer 7.5 mL CTL to new GRex and replenish both with fresh media+cytokines to a final volume of 30 mL.
6.1.5.4 Culture for additional 4-6 days.
6.1.6 Day 10-12: Proceed to SOP M03 (Freezing Cells for Clinical Use).

7. Notes and Limitations 7.1 Cells (PBMC and CTL) should be frozen as back up when possible.
7.2 Since all cells prepared are intended for infusion to patients, it is essential to adhere to proper procedures to prevent misidentification or contamination of patient samples.
7.3 ALL culture vessels and tubes must be labeled with product identifiers including patient name and/or donor name, component number, date of manufacture, and patient/donor ID (P number and/or MRN). Unlabeled material will be discarded.
7.4 Never work with more than one patient product at any one time.
7.5 Always use medium prepared and labeled specifically for each patient's cells. Never use medium to feed more than one patient's cells.
7.6 Perform all steps in a certified biological safety cabinet using aseptic technique and following universal precautions.
7.7 The principle investigator or a designee must calculate the final expanded T cell numbers required. Sufficient cells are required for patient doses as well as QC testing according to the patient's body surface area or weight, predicted dose levels, and whether additional doses are allowed. If possible allow for the chance that the patient may be enrolled on a higher dose level than expected.

8. Expected Results and Interpretation 8.1 The cells must meet release criteria for the given IND such as (but not limited to):
8.1.1 Sufficient CTL numbers for infusion of the patient at the appropriate dose level (determined at that time) and for all QC requirements.
8.1.2 <10% killing of recipient PHA blasts at 20:1 (allogeneic)
8.1.3 <2% CD14+ cells (monocytes)

Example 4

Methods of Treating Mycobacterial Infection in a Subject

Therapeutically effective amounts of effector cells will be administered to subjects over time and efficacy will be determined by monitoring symptoms of bacterial infection in the subject over time after administration.

Example 5

Methods of Expanding T Cells from Healthy Donors Subjects and Patients

Healthy donors and patients were consented on research protocols for blood donation at Children's National Medical Center, the National Institutes of Health, and All Children's Hospital. Donors were evaluated for prior history of BCG vaccination, and those who were vaccinated were evaluated for recent histories of positivity on tuberculin or Quantiferon testing. Patient samples were obtained from individuals with primary immunodeficiency disorders and the presence of an active or recent invasive infection with *M. avium* complex or *M. abscessus* (Table 2).

TABLE 2

Diagnoses of Primary Immunodeficiency Patients and Infection Details

| Subject # | Disorder | cobacterial species | Sites of infection |
|---|---|---|---|
| 1 | CID/NOS | *M. avium* complex | Mediastinal lymphadenitis |
| 2 | Kabuki syndrome | *M. abscessus* | Pulmonary infection |
| 3 | IFNGR1 deficiency | *M. avium* | Bacteremia, GI tract, mesenteric nodes |
| 4 | GATA2 haploinsufficiency | *M. avium* | Pulmonary infection |
| 5 | IL12RB1 deficiency | *M. avium* | Bacteremia, GI tract, pulmonary infection |
| 6 | NEMO | *M. avium* | Bacteremia, colitis |
| 7 | IFN-☐ Autoantibody | *M. abscessus* | Blood, soft tissue, bone |
| 8 | IFN-☐ Autoantibody | *M. avium* complex | Soft tissue, bone |

All research protocols were approved by the Institutional Review Boards at the host institutions.

Isolation of Peripheral Blood Mononuclear Cells

Peripheral blood mononuclear cells (PBMCs) were isolated via Ficoll density centrifugation. Blood was diluted 1:1 in phosphate buffered saline, layered on top of 10-15 mL of Lymphocyte Separation Medium (MP Biomedicals, CA), and spun for 40 min at 400 G at room temperature. PBMCs were harvested from the lymphocyte layer and washed twice with 1×PBS prior to counting and generation of MST lines.

Rapid Generation of Mycobacteria-Specific T Cells from Healthy Donors and Patients On Day 1, PBMCs ($10$-$15 \times 10^6$) were pelleted in a 50 ml conical tube.

Overlapping 15-mer peptide pools encompassing antigens from *M. tuberculosis* (pepmixes) were pooled, with 2 µl of each TB pepmix (five 15-mer pepmix libraries, each reconstituted at a concentration of 0.5 nmol/µL) added to 200 µl CTL medium (45% RPMI, 45% Click's medium, 10% fetal bovine serum with 2 mmol L-glutamine), with a final peptide concentration of 25 nmol/ml. TB pepmixes included peptides from AG85B, PPE68 (Rv3873), ESXA (ESAT-6), ESXB (CFP-10), and ADK. Protein consensus sequences were obtained from NCBI RefSeq (Table 3) for pepmix generation (JPT, Berlin, Germany).

TABLE 3

Mycobacterial Antigen Refseq numbers

| Antigen | RefSeq |
|---|---|
| AG85B | NP_216402.1 |
| PPE68 | WP_003399879.1 |
| ESXA | WP_00033999963.1 |
| ESXB | NP_218391.1 |
| ADK | NP_215247.1 |

PBMC pellets were resuspended in 200 µl of the CTL medium/pepmix and incubated at 37° C. for 30.60 min (FIG. 1). After incubation, PBMCs were resuspended in CTL medium/10% FBS with IL-7 (10 ng/ml) and IL-4 (400 U/ml) at a final concentration of $1 \times 10^6$ cells/ml (R&D Systems, MN). Pepmix-pulsed PBMCs were plated in 24-well plates at 2 ml/well. On Days 3-5, culture medium was monitored for color and cell confluence. For confluent cultures, half-medium change (with IL-7 and IL-4) was performed. On Day 7, culture medium was monitored again and cells were split 1:1 if confluent with a half-medium change. On Days 10-12, cells were harvested and evaluated for antigen specificity and functionality.

MST Generation from Healthy Donors with *M. avium* Sensitin or TB Lysate

*M. tuberculosis* lysate (Strain CDC1551, BEI Resources, Manassas, VA) was reconstituted in 10 mM ammonium bicarbonate at 10 mg/ml. *M. avium* Sensitin (Statens Serum Institut, Denmark, provided courtesy of Dr. Ford von Reyn, Dartmouth University) protein was reconstituted at 1 ug/ml in 1.5 ml of saline. On Day 1, PBMCs (10-15×10$^6$) were co-incubated with lysates at the following conditions: *M. avium* Sensitin (50 ng) or *M. tuberculosis* lysate (100 μg). PBMCs+lysates were resuspended in CTL medium/10% FBS with IL-7 (10 ng/ml) and IL-4 (400 U/ml) at a final concentration of 1×10$^6$ cells/ml and plated in 24-well plates at 2 ml/well. On Days 3-7, culture medium was monitored as before and changed as appropriate. On Days 10-12, cells were harvested and evaluated for TB-specificity and functionality.

IFN-γ ELISPOT Assay and Epitope Mapping

Antigen specificity of T cells was measured with IFN-γ ELISPOT (Millipore, Burlington, MA). T cells were plated at 1×10$^5$/well with no peptide or actin (negative controls), *Staphylococcus* enterotoxin B (SEB) (positive control), or TB pepmix and lysate as stimulants. Specificity was defined as a minimum of 20 spot forming cells (SFC)/1×10$^5$ cells/well with statistical significance of the result over the negative controls by two-tailed Student's T-Test (p<0.05). For epitope mapping, 15 mer peptides were synthesized (GenScript, Piscataway Township, NJ, USA) which spanned the entire AG85B and ESXB proteins, with overlaps of five amino acids between each peptide. ELISPOT plates were sent for IFN-γ SFC counting and confluence determination (Zellnet Consulting, Fort Lee, NJ, USA).

Immunophenotyping of MSTs

Phenotyping of MST cell cultures was performed by flow cytometry with antibodies against CD3, CD8, CD4, CD25, CD14, CD16, CD19, CD27, CD28, CD45RA, CD45RO, CD56, CD57, CD62L, CD127, CCR7, IFN-γ, TNF, CD223 (LAG3), CD95, Perforin, PD-1, TCRγδ, CTLA4, and TIM3 (Milenyi Biotec, Bergisch Gadbach, Germany; Biolegend, San Diego, CA, USA; BD Bioscience, San Jose, CA, USA; Invitrogen, Carlsbad, CA, USA; and Ebioscience, San Diego, CA, USA) (Table 4).

TABLE 4

| Company | Marker | Fluorophore | Clone |
|---|---|---|---|
| \multicolumn{4}{l}{Conjugated Antibody Fluorophores and Clones} |
| BioLegend | CD16 | FITC | 3G8 |
| BioLegend | CD127 | PE | A019D5 |
| Miltenyi | CD14 | PerCP | TUK4 |
| BioLegend | CD19 | PerCP Cy5.5 | HIB19 |
| MIltenyi | CD57 | PE-Vio770 | REA769 |
| BioLegend | TCRgd | APC | B1 |
| BioLegend | CD25 | Ax700 | BC96 |
| BioLegend | CD3 | APC-Fire750 | SK7 |
| BioLegend | CD8 | BV421 | RPA-T8 |
| BioLegend | CD4 | BV605 | DREG-56 |
| BioLegend | CD27 | FITC | O323 |
| BioLegend | CD95 | PE-Daz594 | OKT4 |
| BD | CD28 | PECy5 | CD28.2 (RUO) |
| Miltenyi | CD45RO | PE-Vio770 | REA611 |
| BioLegend | CCR7 | Ax700 | G043H7 |
| BioLegend | CD62L | BV650 | DREG-56 |

TABLE 4-continued

Conjugated Antibody Fluorophores and Clones

| Company | Marker | Fluorophore | Clone |
|---|---|---|---|
| eBioscience | CTLA4 | FITC | 14D3 |
| BioLegend | TNFa | PE | MAb11 |
| BioLegend | Perforin | PerCP Cy5.5 | B-D48 |
| BioLegend | CD223 (LAG3) | PE-Cy7 | 11C3C65 |
| BD | PD-1 | APC | MIH4 |
| Invitrogen | IFNy | Ax700 | 4S.B3 |
| BioLegend | CD366 (TIM3) | BV650 | F38-2E2 |

Figure 8:
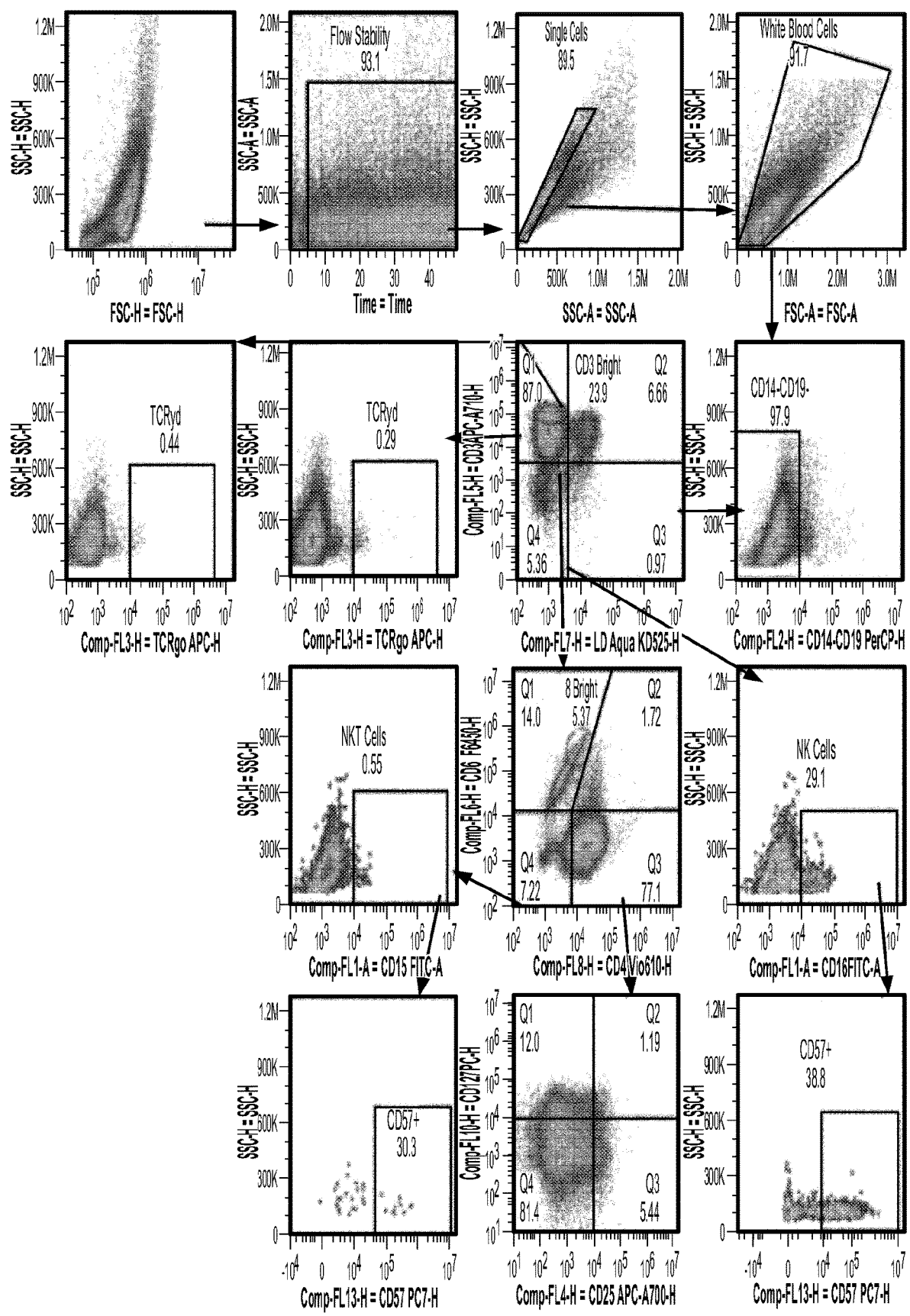
FIG. 8 depicts a gating strategy for surface staining flow cytometry. CD14/CD19 are combined for exclusion gating. LD=live/dead.
Figure 9:
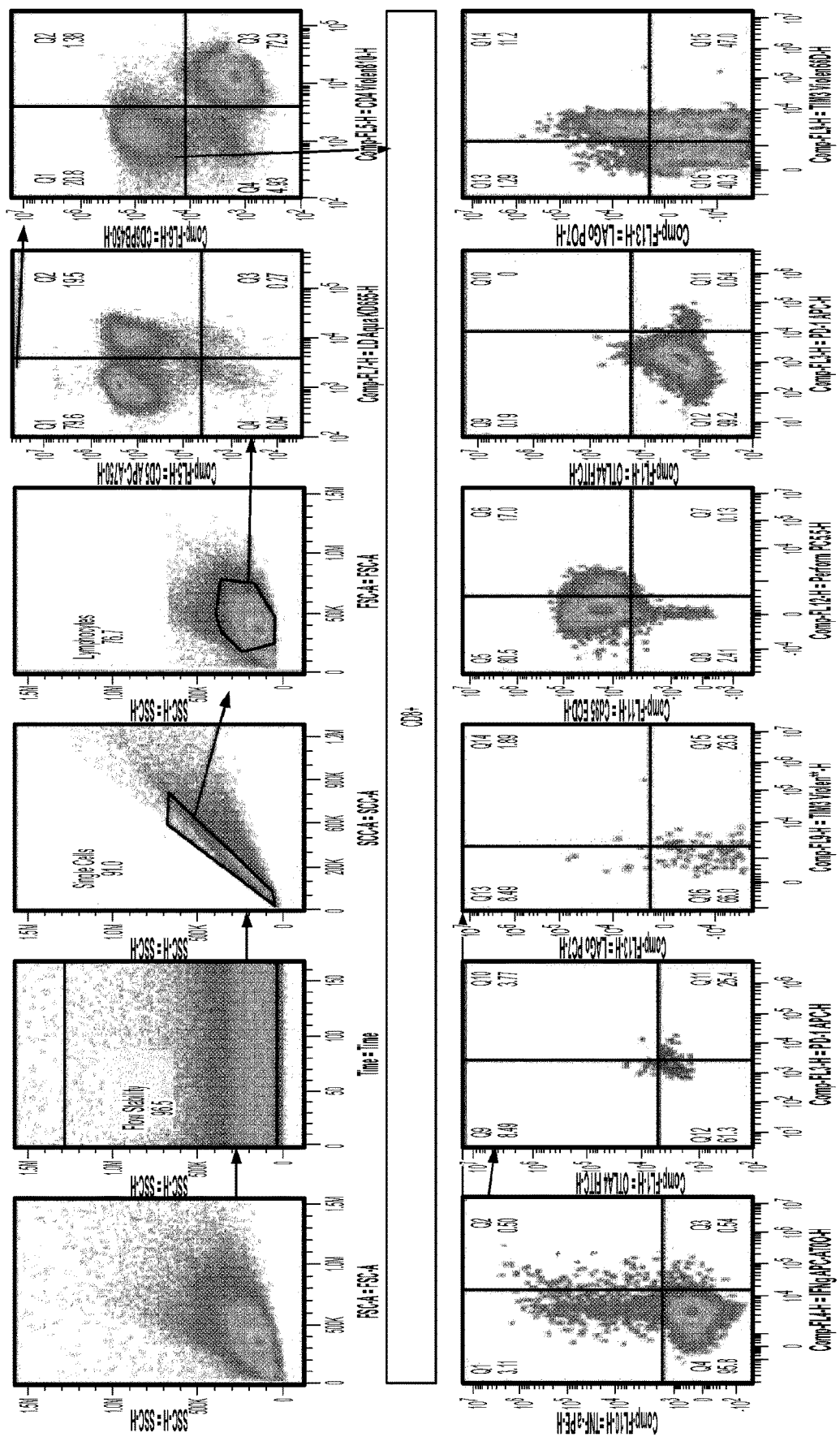
FIG. 9 depicts a gating strategy for intracellular flow cytometry. LD=live/dead.

On Day 1, MSTs from healthy and BCG-vaccinated donors were rested overnight with low dose IL-2 (50 U/mL). On Day 2, T cells were washed and plated at 1×10$^6$ cells/well with corresponding pepmix, αCD28/CD49 co-stimulator, and Brefeldin A and incubated for 6 h. Conditions were as follows: no pepmix, actin pepmix, SEB, or a mix of mycobacterial peptides (equal concentrations of PPE68, ESXA, ESXB, AG85B, and ADK pepmixes) at 2.5 ug/well. After 6 h incubation in the above conditions, cells were washed, stained for surface markers, washed, and fixed with 4% paraformaldehyde. Cells were then permeabilized with saponin (Perm Wash Buffer, BD Biosciences, San Diego, CA), stained with intracellular antibodies, and washed. T cells transduced with a chimeric antigen receptor specific for GD2 were utilized as a control for presence of co-inhibitory receptors (courtesy of Dr. Crystal Mackall, Stanford University) (33). Samples were acquired on a CytoFlex S Flow Cytometer (Beckman Coulter, Indianapolis, IN, USA), and analyzed in FlowJo VX (FlowJo LLC, Ashland, OR, USA). Standardized gating strategies were utilized for surface staining (FIG. 8) and intracellular staining (FIG. 9).

Multiplex Cytokine Assay

MST product functionality was measured with the Bioplex Pro Human 17-plex Cytokine Assay kit (Biorad, Hercules, CA, USA). On Day 1, MSTs from healthy donors were rested overnight with low dose IL-2 (50 U/mL). On Day 2, T cells were washed and plated at 1×10$^6$ cells/well with 1 μl of corresponding pepmix. Conditions were as follows: No pepmix (control), actin only (control), SEB (positive control), AG85B, PPE68, ESXA, ESXB, or ADK at 1 ug/well. On Day 3, supernatants were harvested from the wells, spun down to remove debris, and plated on the multiplex plate. For immunodeficient patients, supernatants were collected from ELISPOT plates to be run on 17-plex, due to limited cell numbers. The Biorad 17-plex multiplex manufacturer's protocol was followed and read on a MAGPIX System (Luminex, Austin, TX).

HLA Typing

Selected donor samples were sent for high resolution SSO HLA typing (Kashi Clinical Laboratories, Portland, OR).

Data Analysis

Data analysis was performed in Graphpad Prism (GraphPad Software, La Jolla, CA) and SAS 9.3 (SAS Institute, Cary, NC). The Kruskal-Wallis test with two-tail significance level α of 0.05 was used to test for differences between multiple data groups, and two-tailed T-tests were used for pairwise data analysis.

Results

Mycobacteria-Specific T Cells can be Expanded from Healthy Donors

Ten healthy donors were evaluated for T cell responses to mycobacterial antigens. Six donors had prior histories of BCG vaccination, of whom three had known histories of positivity on delayed type hypersensitivity testing but negative chest radiographs. One had a previously negative Quantiferon test.

Following 10-days ex vivo expansion of MSTs, IFN-γ ELISpot demonstrated reactivity against a median of 3 of 5 antigens per subject (range 1-5, Table 5).

TABLE 5

Statistical Analysis of Donor Antigen Specificity

| Donor | Condition | IFN-□ | SPW | Mean | P value (vs Actin) |
|---|---|---|---|---|---|
| Donor 1 | CTL only | 5 | 0 | 1 | 2.00 |
| | Actin | 1 | 2 | 2 | 1.67 |
| | SEB | 483 | 455 | 456 | 464.67 |
| | AG85A | 11 | 14 | 17 | 14.00 0.013596339 |
| | PPE68 | 6 | 2 | 2 | 3.33 0.422649731 |
| | ESAT6 | 0 | 1 | 27 | 9.33 0.469685578 |
| | ESXB | 53 | 48 | 42 | 47.67 0.005623287 |
| | ADK | 1 | 0 | 0 | 0.33 0.183503419 |
| Donor 2 | CTL only | 1 | 2 | 1 | 1.33 |
| | Actin | 4 | 0 | 4 | 2.67 |
| | SEB | 408 | 409 | 444 | 420.33 |
| | AG85A | 114 | 173 | 133 | 140.00 0.017961432 |
| | PPE68 | 46 | 33 | 28 | 35.67 0.02390784 |
| | ESAT6 | 23 | 32 | 34 | 29.67 0.021679195 |
| | ESXB | 25 | 29 | 28 | 27.33 0.008829797 |
| | ADK | 0 | 0 | 0 | 0.00 0.183503419 |
| Donor 3 | CTL only | 0 | 0 | 0 | 0.00 |
| | Actin | 0 | 1 | 1 | 0.67 |
| | SEB | 517 | 500 | 523 | 513.33 |
| | AG85A | 51 | 49 | 62 | 54.00 0.005385862 |
| | PPE68 | 1 | 2 | 2 | 1.67 0.101191507 |
| | ESAT6 | 12 | 11 | 14 | 12.33 0.005665768 |
| | ESXB | 608 | 584 | 601 | 597.67 0.000152412 |
| | ADK | 0 | 0 | 1 | 0.33 0.422649731 |
| Donor 4 | CTL only | 1 | 0 | 1 | 0.67 |
| | Actin | 0 | 2 | 0 | 0.67 |
| | SEB | 452 | 358 | 381 | 397.00 |
| | AG85A | 18 | 29 | 18 | 21.67 0.019803941 |
| | PPE68 | 2 | 5 | 6 | 4.33 0.092735291 |
| | ESAT6 | 0 | 1 | 0 | 0.33 0.422649731 |
| | ESXB | 1 | 1 | 0 | 0.67 1 |
| | ADK | 1 | 0 | 0 | 0.33 0.74180111 |
| Donor 5 | CTL only | 6 | 0 | 1 | 2.33 |
| | Actin | 7 | 7 | 4 | 6.00 |
| | SEB | 596 | 585 | 519 | 566.67 |
| | AG85A | 501 | 581 | 529 | 537.00 0.001917902 |
| | PPE68 | 107 | 80 | 102 | 96.33 0.009119242 |
| | ESAT6 | 29 | 29 | 38 | 32.00 0.022860164 |
| | ESXB | 569 | 428 | 547 | 514.67 0.007457789 |
| | ADK | 13 | 10 | 9 | 10.67 0.033908217 |
| Donor 6 | CTL only | 0 | 1 | 1 | 0.67 |
| | Actin | 0 | 1 | 0 | 0.33 |
| | SEB | 478 | 497 | 456 | 477.00 |
| | AG85A | 7 | 6 | 5 | 6.00 0.01355995 |
| | PPE68 | 15 | 29 | 19 | 21.00 0.032901347 |
| | ESAT6 | 1 | 0 | 0 | 0.33 1 |
| | ESXB | 1 | 0 | 0 | 0.33 1 |
| | ADK | 0 | 1 | 2 | 1.00 0.422649731 |
| Donor 7 | CTL alone | 8 | 5 | | 6.50 |
| | Actin | 2 | 5 | | 3.50 |
| | SEB | 604 | 576 | | 590.00 |
| | AG85A | 385 | 400 | | 392.50 0.000386371 |
| | PPE68 | 386 | 374 | | 380.00 0.000269728 |
| | ESAT6 | 95 | 104 | | 99.50 0.002432502 |
| | ESXB | 22 | 30 | | 26.00 0.034210227 |
| | ADK | 31 | 32 | | 31.50 0.003173604 |
| Donor 8 | CTL alone | 0 | 1 | | 0.50 |
| | Actin | 0 | 0 | | 0.00 |
| | SEB | 561 | 895 | | 728.00 |
| | AG85A | 269 | 227 | | 248.00 0.007094056 |
| | PPE68 | 174 | 190 | | 182.00 0.001926552 |
| | ESAT6 | 64 | 75 | | 69.50 0.006204393 |
| | ESXB | 17 | 24 | | 20.50 0.02793371 |
| | ADK | 35 | 36 | | 35.50 0.000198314 |
| Donor 9 | CTL alone | 3 | 2 | | 2.50 |
| | Actin | 9 | 6 | | 7.50 |
| | SEB | 1957 | 1584 | | 1770.50 |
| | AG85A | 466 | 419 | | 442.50 0.002917556 |
| | PPE68 | 135 | 127 | | 131.00 0.001194401 |
| | ESAT6 | 97 | 71 | | 84.00 0.028037425 |
| | ESXB | 37 | 47 | | 42.00 0.022136969 |
| | ADK | 27 | 35 | | 31.00 0.031493807 |
| Donor 10 | CTL alone | 1 | 0 | | 0.50 |
| | Actin | 1 | 0 | | 0.50 |
| | SEB | 906 | 810 | | 858.00 |
| | AG85A | 111 | 109 | | 110.00 0.000104235 |
| | PPE68 | 318 | 283 | | 300.50 0.003388257 |
| | ESAT6 | 4 | 1 | | 2.50 0.333333333 |
| | ESXB | 6 | 7 | | 6.50 0.013606076 |
| | ADK | 1099 | 1042 | | 1070.50 0.000708914 |

(bold: meets criteria for antigen specificity)

Figure 2A:
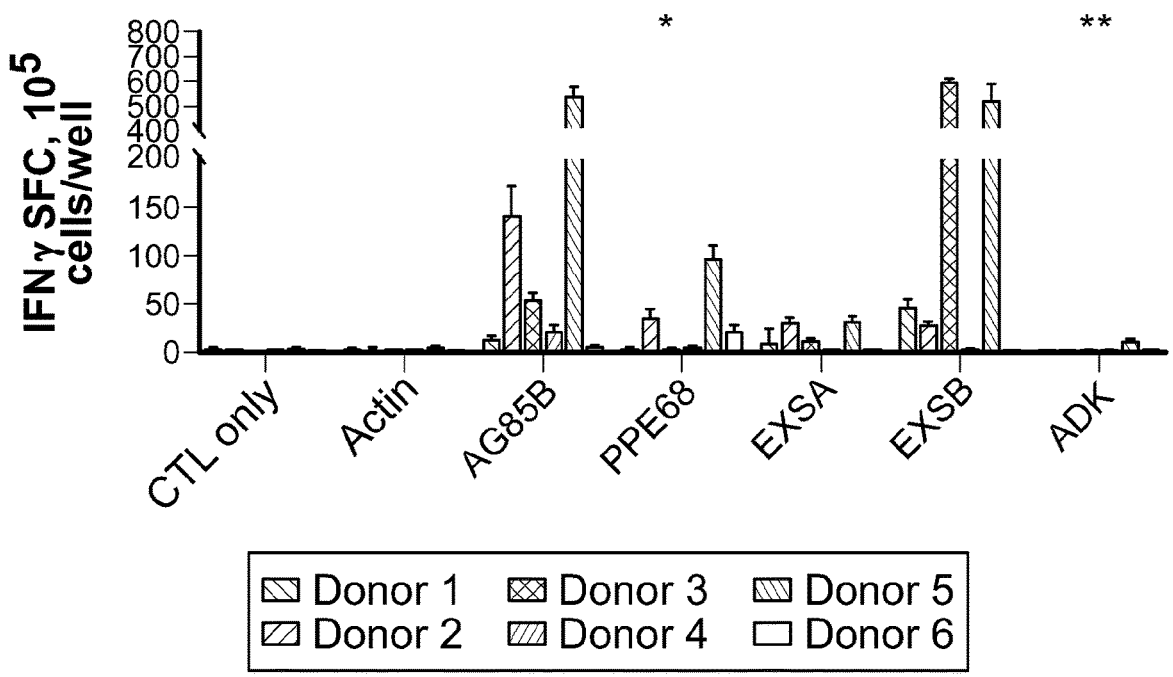
FIG. 2A depicts IFN-γ ELISpot of ex vivo expanded MSTs at day 10 showed specificity to multiple mycobacterial antigens in both BCG immunized donors and non-BCG vaccinated donors.
Figure 2B:
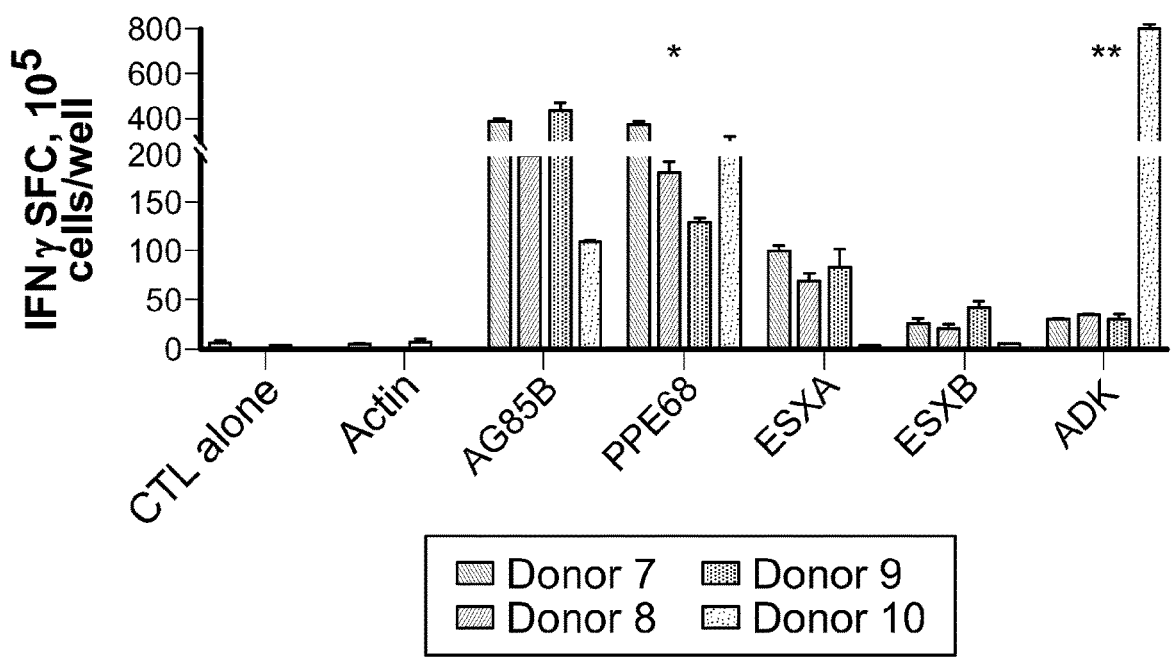
FIG. 2B depicts significant differences between groups was noted in the responses against PPE68 (*p=0.028) and ADK (**p=0.015). SFC, Spot forming colonies.

Comparison of BCG-immunized (FIG. 2A) and non-immunized donors (FIG. 2B) demonstrated a greater likelihood of response to PPE68 (p=0.028) and ADK (p=0.015) in the BCG-non-immunized donors (Table 6).

TABLE 6

Statistical Analysis of MST Antigen Specificity of BCG Vaccinated versus Naive Healthy Donors

| Covariate | Statistics | BCG Vaccinated | BCG Naive | Non-Parametric P-value |
|---|---|---|---|---|
| CTL_only | N | 5 | 5 | 0.834 |
| | Mean | 1.27 | 2.13 | |
| | Median | 1.33 | 0.67 | |
| | Min | 0 | 0.5 | |
| | Max | 2.33 | 6.5 | |
| | Std Dev | 0.95 | 2.58 | |
| Actin | N | 5 | 5 | 0.463 |
| | Mean | 2.34 | 2.37 | |
| | Median | 1.67 | 0.5 | |
| | Min | 0.67 | 0 | |
| | Max | 6 | 7.5 | |
| | Std Dev | 2.21 | 3.2 | |
| AG85B | N | 5 | 5 | 0.602 |
| | Mean | 153.33 | 239.8 | |
| | Median | 54 | 248 | |
| | Min | 14 | 6 | |
| | Max | 537 | 442.5 | |
| | Std Dev | 220.22 | 184.38 | |
| PPE68 | N | 5 | 5 | 0.028 |
| | Mean | 28.27 | 202.9 | |
| | Median | 4.33 | 182 | |
| | Min | 1.67 | 21 | |
| | Max | 96.33 | 380 | |
| | Std Dev | 40.59 | 141.05 | |
| ESXA | N | 5 | 5 | 0.402 |
| | Mean | 16.73 | 51.17 | |
| | Median | 12.33 | 69.5 | |
| | Min | 0.33 | 0.33 | |
| | Max | 32 | 99.5 | |
| | Std Dev | 13.64 | 46.65 | |
| ESXB | N | 5 | 5 | 0.117 |
| | Mean | 237.6 | 19.07 | |
| | Median | 47.67 | 20.5 | |
| | Min | 0.67 | 0.33 | |
| | Max | 597.67 | 42 | |
| | Std Dev | 292.76 | 16.47 | |
| ADK | N | 5 | 5 | 0.015 |
| | Mean | 2.33 | 233.9 | |
| | Median | 0.33 | 31.5 | |
| | Min | 0 | 1 | |
| | Max | 10.67 | 1070.5 | |
| | Std Dev | 4.66 | 467.88 | |

Figure 3A:
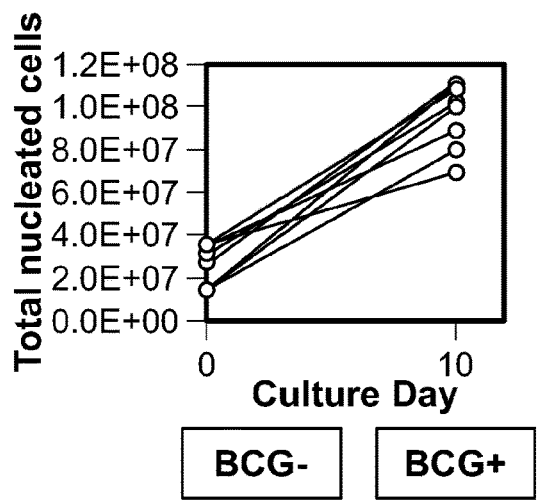
FIG. 3A depicts Mycobacterial-specific T cells expanded during culture with a mean fold-expansion of 4.4 BCG-= BCG non-immunized; BCG=BCG immunized.
Figure 3B:
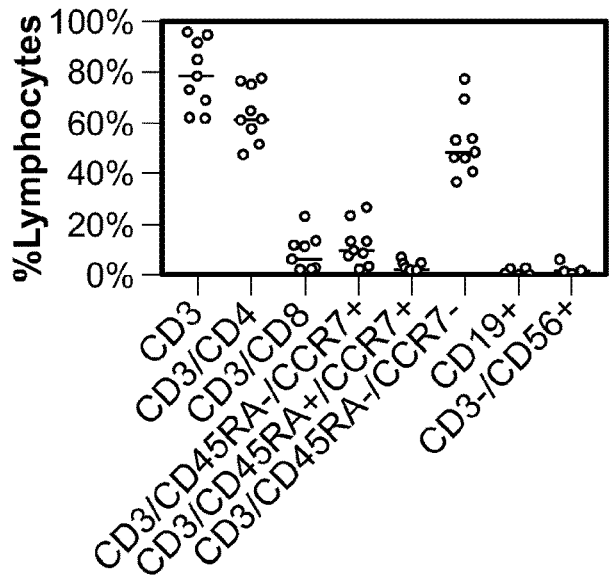
FIG. 3B surface phenotyping of MSTs following expansion showed a predominance of CD4+ T cells with large effector memory population and smaller central memory population. Lines, median value.

Cultures underwent a mean 4.4-fold expansion, with recovery of 7-11×107 cells (FIG. 3A).

Ex Vivo Expanded MSTs are Predominantly CD4+ T Cells

Figure 3C:
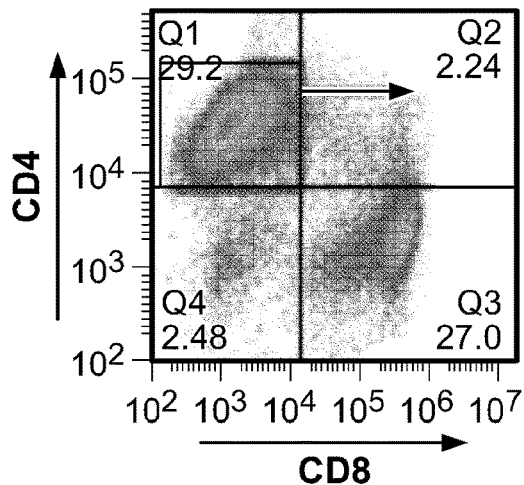
FIG. 3C depicts example plots from MTSs expanded from Donor 9 show a large CD4$^+$ effector memory ($T_{EM}$) population and smaller effector ($T_{eff}$) and central memory ($T_{cm}$) population with minimal naïve T cells ($T_n$).
Figure 3C:
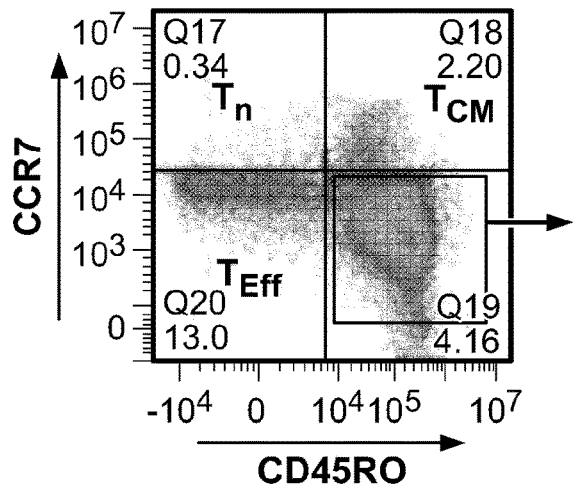
Figure 3C:
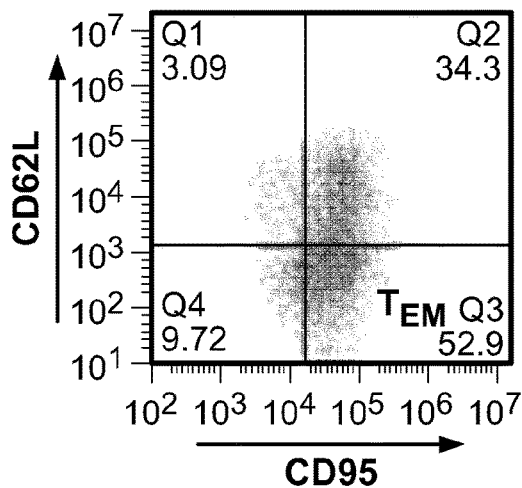
Figure 4:
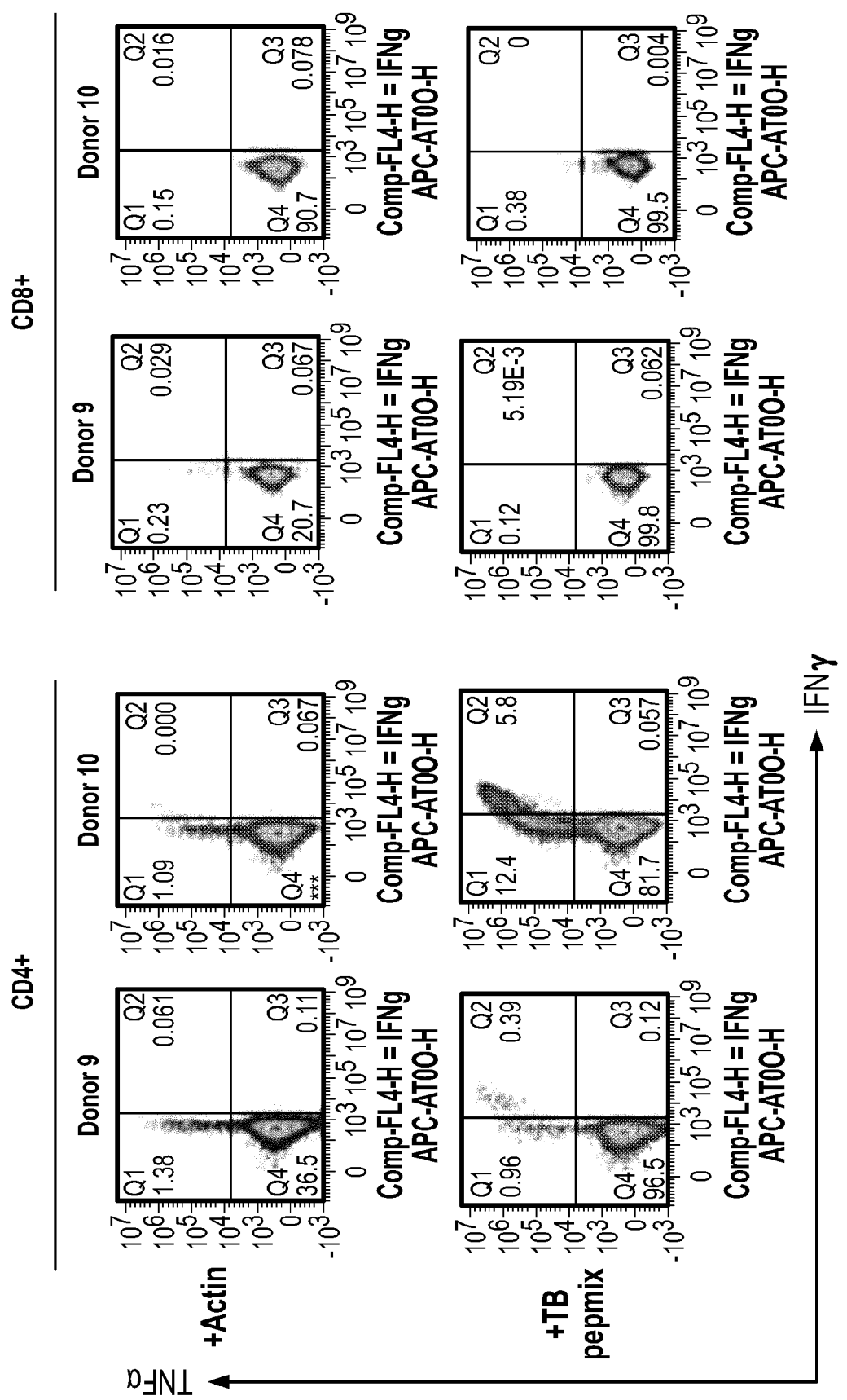
FIG. 4 depicts MSTs expanded from healthy donors are polyfunctional. Intracellular flow cytometry demonstrated production of IFN-γ and TNF in response to mycobacterial pepmix restimulation exclusively in CD4$^+$ T cells from MSTs expanded from healthy donors, with no responses seen in CD8$^+$ T cells.

Flow cytometry of bulk MSTs following culture showed that the majority of cells were CD4+ T cells (median 63.7% CD3+/CD4+, range 47.5-77.7%, FIG. 3), with a small minority of CD8+ T cells (median 6% CD3+/CD8+, range 1.1-23%). The majority of CD4+ T cells were effectors (median 66.1%, range 60.8-68.9%) with a smaller central memory population (median 1.6%, range 1.4-4.4%) (FIG. 3C). There was no outgrowth of B cells or NK cells.

Figure 5A:
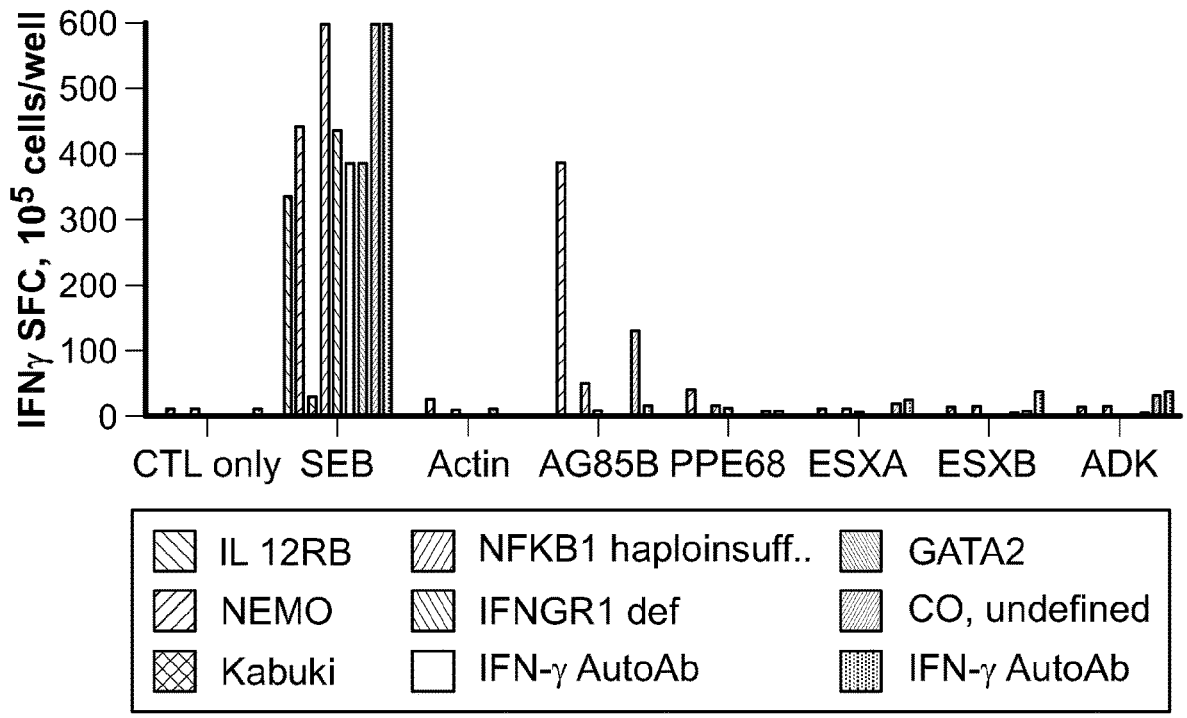
FIG. 5A depicts IFN-γ ELISpot of T cells expanded from patients with primary immunodeficiency disorders (PID) showed decreased to absent responses to mycobacterial antigens, with exception of a patient with NFKB1 hapioinsufficiency. Two patients with IFN-γ autoantibodies had detectable responses. SEB, staphylococcal enterotoxin B; CID, combined immunodeficiency.

Mycobacterial Responses are Largely Absent in Patients with Primary Immunodeficiency Seven subjects with primary immunodeficiency disorders and invasive infections with *M. avium* complex or M *abscessus* were tested for responses against mycobacterial antigens. Underlying diagnoses were IL12RB1 deficiency, NFKB1 haploinsufficiency, IFNGR1 deficiency, GATA2 haploinsufficiency, Kabuki syndrome, NEMO deficiency, and undefined combined immunodeficiency (CID). Two patients with anti-IFN-γ autoantibodies and invasive infections with *M. avium* and *M. abscessus* were also evaluated. Following a 10-day expansion, evaluation of specificity via IFN-γ ELISPOT demonstrated specificity to mycobacterial antigens in two of the seven patients with PID (FIG. 5A, Table 7).

TABLE 7

Statistical Analysis of PID Patient Antigen Specificity

| Donor | Condition | IFN-□ | SPW | Mean | P value (vs Actin) |
|---|---|---|---|---|---|
| IL12RB1 | CTL only | 0 | 0 | | 0.00 | |
| | Actin | 2 | 1 | | 1.50 | |
| | SEB | 324 | 354 | | 339.00 | |
| | AG85A | 0 | 0 | | 0.00 | 0.095465966 |
| | PPE68 | 0 | 0 | | 0.00 | 0.095465966 |
| | ESAT6 | 0 | 0 | | 0.00 | 0.095465966 |
| | ESXB | 0 | 1 | | 0.50 | 0.292893219 |
| | ADK | 1 | 0 | | 0.50 | 0.292893219 |
| Kabuki | CTL alone | 0 | 1 | 1 | 0.7 | |
| | Actin | 16 | 11 | 9 | 12.0 | |
| | SEB | 0 | 0 | 0 | 0.0 | |
| | AG85B | 0 | 0 | 2 | 0.7 | 0.048927794 |
| | PPE68 | 0 | 3 | 1 | 1.3 | 0.057190958 |
| | ESAT6 | 2 | 0 | 1 | 1.0 | 0.02390784 |
| | ESXB | 2 | 2 | 2 | 2.0 | 0.040705781 |
| | ADK | 3 | 0 | 5 | 2.7 | 0.075862293 |
| IFNGR1 | CTL alone | 3 | 1 | 3 | 2.3 | |
| | Actin | 3 | 0 | 1 | 1.3 | |
| | SEB | 442 | 495 | 377 | 438.0 | |
| | AG85B | 12 | 6 | 5 | 7.7 | 0.048810269 |
| | PPE68 | 14 | 9 | 22 | 15.0 | 0.066492647 |
| | ESAT6 | 2 | 4 | 3 | 3.0 | 0.370059212 |
| | ESXB | 3 | 1 | 3 | 2.3 | 0.225403331 |
| | ADK | 2 | 4 | 3 | 3.0 | 0.37005 |
| NEMO | Medium | 4 | 3 | 8 | 5.00 | |
| | Actin | 7 | 10 | 8 | 8.33 | |
| | SEB | 1068 | 2.66667 | 1092 | 1080.89 | |
| | AG85B | 31 | 55 | 55 | 47.00 | 0.034338707 |
| | PPE68 | 18 | 9 | 21 | 16.00 | 0.22156794 |
| | ESAT6 | 8 | 10 | 20 | 12.67 | 0.376697708 |
| | ESXB | 10 | 22 | 14 | 15.33 | 0.118082896 |
| | ADK | 16 | 16 | 13 | 15.00 | 0.030996834 |
| NFKB1 | CTL only | 6 | 9 | | 7.5 | |
| | Actin | 20 | 27 | | 23.5 | |
| | SEB | 456 | 428 | | 442.0 | |
| | AG85A | 396 | 381 | | 388.5 | 0.000513772 |
| | PPE68 | 41 | 39 | | 40.0 | 0.045381191 |
| | ESAT6 | 14 | 12 | | 13.0 | 0.102104838 |
| | ESXB | 7 | 14 | | 10.5 | 0.1195289 |
| | ADK | 10 | 9 | | 9.5 | 0.058258088 |
| GATA2 | CTL only | 0 | 0 | | 0.0 | |
| | Actin | 0 | 0 | | 0.0 | |

TABLE 7-continued

Statistical Analysis of PID Patient Antigen Specificity

| Donor | Condition | IFN-☐ | SPW | Mean | P value (vs Actin) |
|---|---|---|---|---|---|
| | SEB | 42 | 21 | 31.5 | |
| | AG85B | 0 | 0 | 0.0 | ND |
| | PPE68 | 0 | 0 | 0.0 | ND |
| | ESAT6 | 0 | 0 | 0.0 | ND |
| | ESXB | 0 | 0 | 0.0 | ND |
| | ADK | 0 | 0 | 0.0 | ND |
| CID | CTL only | 0 | 0 | 0.00 | |
| | Actin | 0 | 0 | 0.00 | |
| | SEB | 366 | 450 | 356 390.67 | |
| | AG85B | 1 | 0 | 1 0.67 | ND |
| | PPE68 | 0 | 0 | 0 0.00 | ND |
| | ESAT6 | 0 | 0 | 0 0.00 | ND |
| | ESXB | 0 | 1 | 1 0.67 | ND |
| | ADK | 1 | 0 | 0 0.33 | ND |
| Ng AutoAb | CTL only | 3 | 2 | 2.5 | |
| | Actin | 2 | 3 | 2.5 | |
| | SEB | 3.142857 | 1157 | 065.07143 | |
| | AG85B | 142 | 128 | 135 | 0.002793519 |
| | PPE68 | 3 | 4 | 3.5 | 0.292893219 |
| | ESAT6 | 16 | 23 | 19.5 | 0.040634498 |
| | ESXB | 6 | 3 | 4.5 | 0.333333333 |
| | ADK | 23 | 33 | 28 | 0.036706506 |
| Ng AutoAb | CTL only | 20 | 2 | 11.00 | |
| | Actin | 2 | 2 | 2.00 | |
| | SEB | 61.05263 | 3.05263 | 1082.05 | |
| | AG85B | 12 | 22 | 17.00 | 0.095465966 |
| | PPE68 | 2 | 4 | 3.00 | 0.422649731 |
| | ESAT6 | 26 | 22 | 24.00 | 0.008163402 |
| | ESXB | 34 | 38 | 36.00 | 0.003442351 |
| | ADK | 16 | 16 | 16.00 | ND |

Figure 5B:
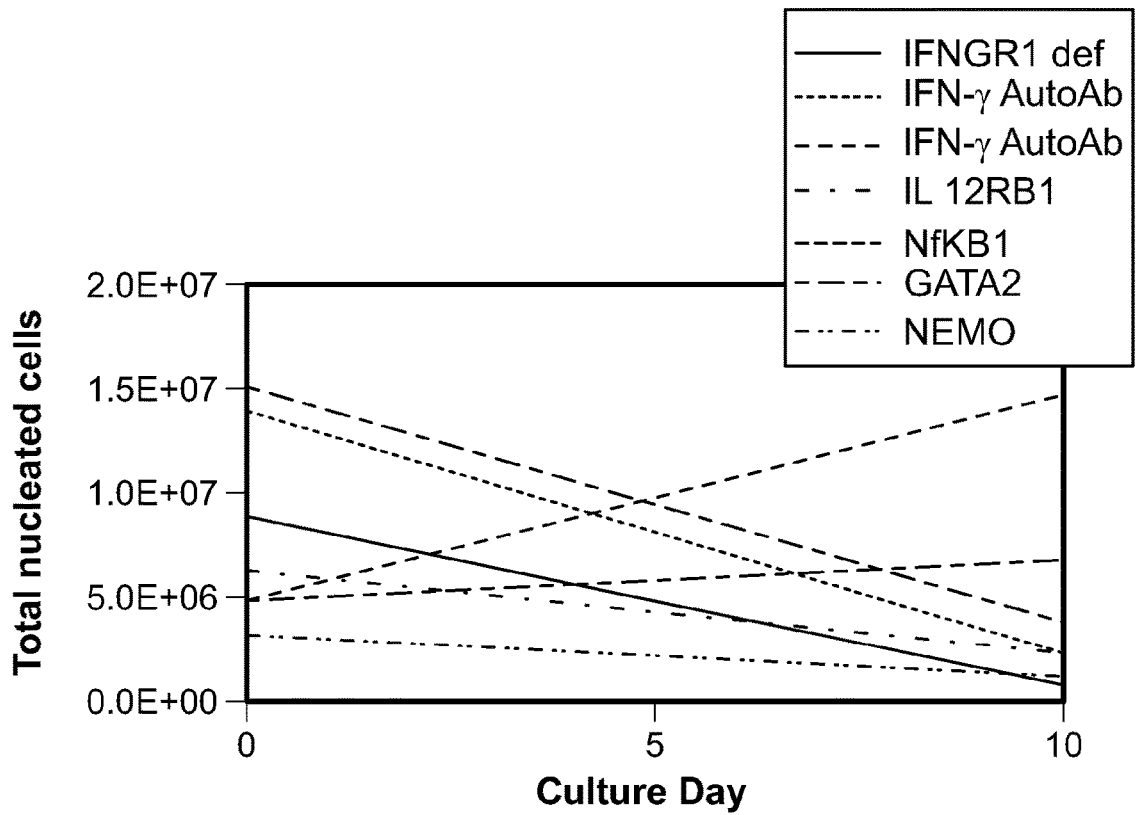
FIG. 5B depicts Ex vivo culture of T cells from patients with PID yielded no expansion in all but two patients.

Both of the subjects with anti-IFN-γ autoantibodies had detectable T cell responses to mycobacterial antigens (AG85B and ADK in one subject, and ESXA and ESXB in the other). Cell expansion during the culture period was minimal or absent in all patients (FIG. 5B) with the exception of the subject with NFKB1 haploinsufficiency (3.2-fold expansion).

Figure 6A:
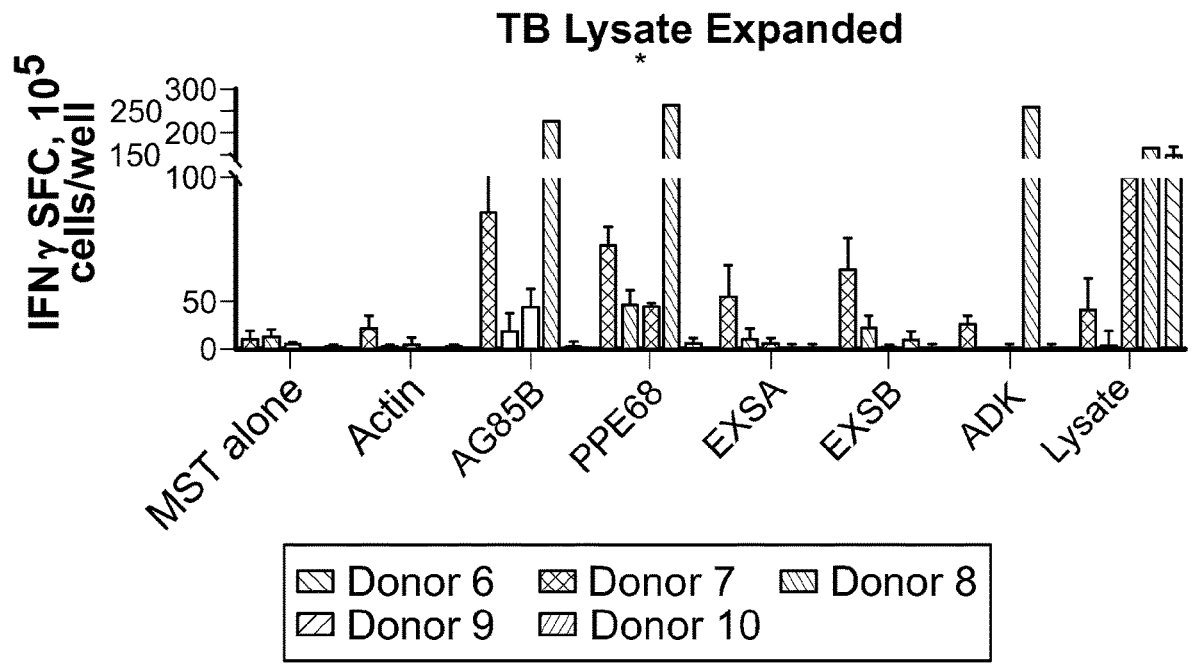
FIG. 6 depicts MST responses are comparable using peptide stimulation vs. lysate or sensitin. IFN-γ ELISpot from MSTs expanded using TB lysate or *M. avium* sensitin, showed specificity to multiple mycobacterial pepmixes, which were comparable in magnitude to the response to restimulation with lysate or sensitin. Differences in responses were only significant for PPE68 (*p=0.032). SFC, spot forming colonies; SEB, staphylococcal enterotoxin B.
Figure 6B:
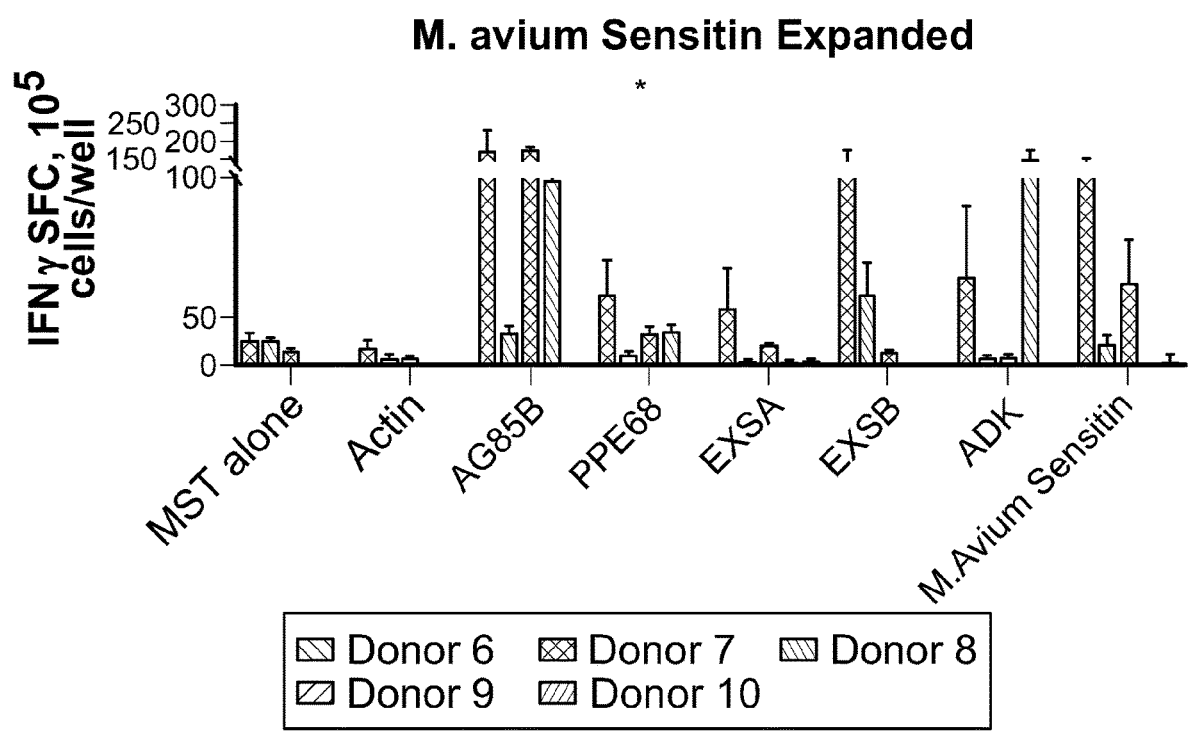

MSTs Expanded Against *M. tuberculosis* Lysate or *M. avium* Sensitin Recognize Immunodominant Antigens Following 10 days of culture after stimulation with lysate from *M. tuberculosis* or *M. avium* sensitin, MSTs from all five tested donors showed specificity for the mycobacterial antigen pepmixes or against lysate or sensitin (FIG. 6). Analysis of MST responses via IFN-γ ELISPOT following expansion against the pepmixes, lysate, or sensitin showed significant differences in the response to PPE68 (p=0.032), but not to the other antigens (Table 8).

TABLE 8

Statistical Analysis of MST Antigen Specificity by Culture Condition

| | | Condition | | | |
|---|---|---|---|---|---|
| Covariate | Statistics | Pepmix N = 5 | Sensitin N = 5 | Lysate N = 5 | Non-Parametric P-value |
| CTLonly | N | 5 | 5 | 5 | |
| | Mean | 2.13 | 6.93 | 4.87 | |
| | Median | 0.67 | 7.33 | 4 | |
| | Min | 0.5 | 0.33 | 1.67 | |
| | Max | 6.5 | 13.67 | 8 | |
| | Std Dev | 2.58 | 6.51 | 2.83 | |
| Actin | N | 5 | 5 | 5 | 0.504 |
| | Mean | 2.37 | 3.33 | 4.67 | |
| | Median | 0.5 | 3.33 | 2.33 | |
| | Min | 0 | 0 | 1 | |
| | Max | 7.5 | 8.67 | 13 | |
| | Std Dev | 3.2 | 3.43 | 4.84 | |
| AG85B | N | 5 | 5 | 5 | 0.221 |
| | Mean | 239.8 | 88.93 | 71.66 | |
| | Median | 248 | 97.67 | 25.33 | |
| | Min | 6 | 0 | 4 | |
| | Max | 442.5 | 169 | 236.33 | |
| | Std Dev | 184.38 | 79.14 | 96.92 | |
| PPE68 | N | 5 | 5 | 5 | 0.032 |
| | Mean | 202.9 | 15.6 | 78.6 | |
| | Median | 182 | 15.67 | 26.33 | |
| | Min | 21 | 1 | 6.67 | |
| | Max | 380 | 37.67 | 271.67 | |
| | Std Dev | 141.05 | 14.11 | 109.76 | |
| ESXA | N | 5 | 5 | 5 | 0.431 |
| | Mean | 51.17 | 9 | 10.07 | |
| | Median | 69.5 | 2 | 5 | |
| | Min | 0.33 | 1 | 2.67 | |
| | Max | 99.5 | 29.67 | 31.33 | |
| | Std Dev | 46.65 | 12.28 | 11.96 | |
| ESXB | N | 5 | 5 | 5 | 0.911 |
| | Mean | 19.07 | 33.26 | 14.53 | |
| | Median | 20.5 | 7.33 | 6.33 | |
| | Min | 0.33 | 0 | 1 | |
| | Max | 42 | 122.33 | 48 | |
| | Std Dev | 16.47 | 51.98 | 19.34 | |
| ADK | N | 5 | 5 | 5 | 0.651 |
| | Mean | 233.9 | 38.6 | 57.73 | |
| | Median | 31.5 | 5 | 3 | |

TABLE 8-continued

Statistical Analysis of MST Antigen Specificity by Culture Condition

| | | Condition | | | |
|---|---|---|---|---|---|
| Covariate | Statistics | Pepmix N = 5 | Sensitin N = 5 | Lysate N = 5 | Non-Parametric P-value |
| | Min | 1 | 0 | 1.33 | |
| | Max | 1070.5 | 137.67 | 266 | |
| | Std Dev | 467.88 | 58.5 | 116.59 | |

Figure 10:
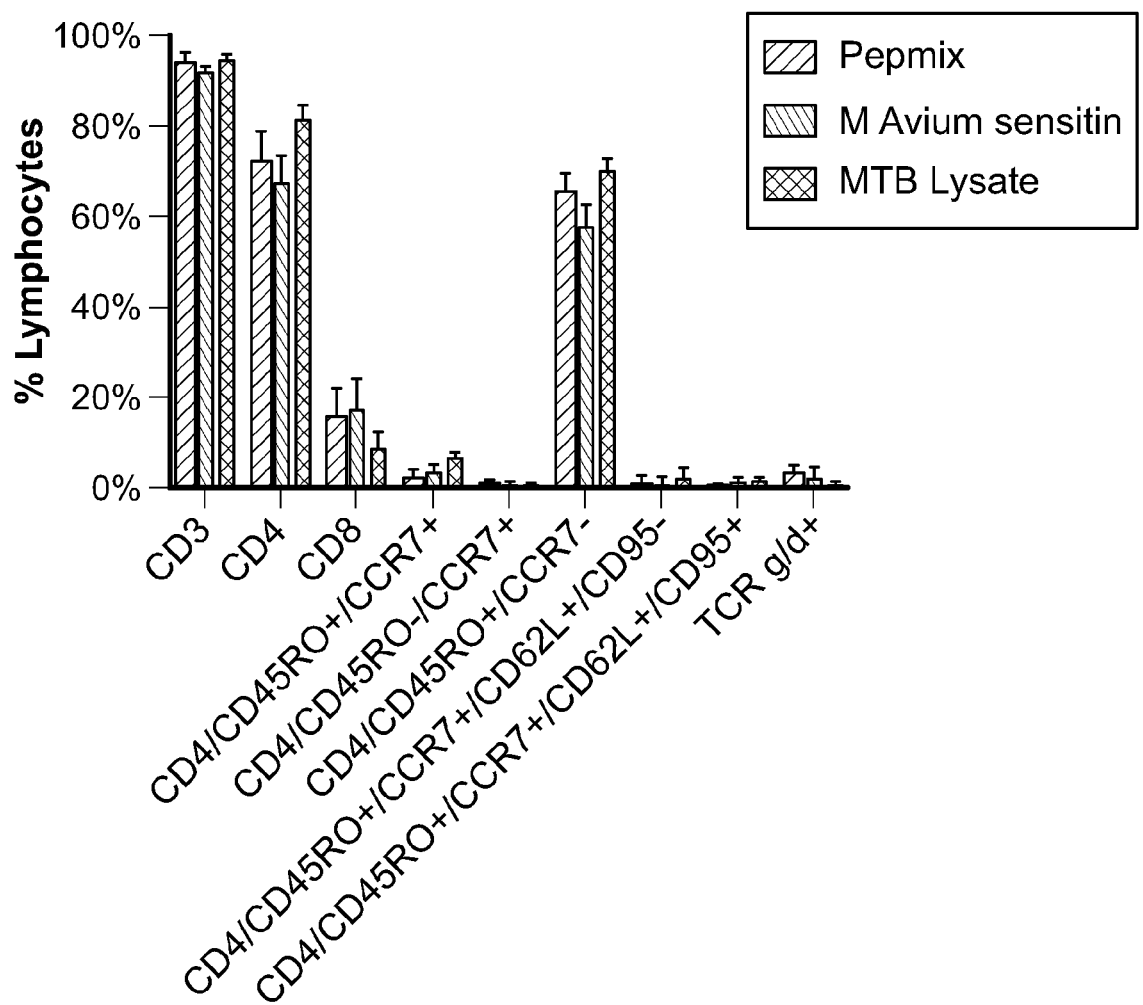
FIG. 10 depicts surface immunophenotyping of MSTs produced using pepmix, sensitin, and lysate showed minimal differences in T cell subsets for the different growth conditions. The expanded cells were predominantly CD4+ effector memory T cells (CD4+/CD45RO+/CCR7−), with smaller central memory population (CD4/CD45RO$^+$/CCR7$^+$/CD62L$^+$).

Pairwise analysis showed a statistically significant difference in the response to PPE68 of MSTs generated using pepmix vs. sensitin (p=0.016), but no difference between MSTs generated using pepmix vs. lysate (p=0.173) or lysate vs. sensitin (p=0.116). Comparative surface flow cytometry of MSTs generated using pepmix, sensitin, or lysate, all showed a predominance of CD4+ effector memory cells, with no notable differences between subpopulations, and a minimal percentage of $\gamma/\delta$ T-cells (FIG. 10).

Epitopes in Mycobacterial AG85B and ESXB are Variably Conserved Across Species

Figure 7A:
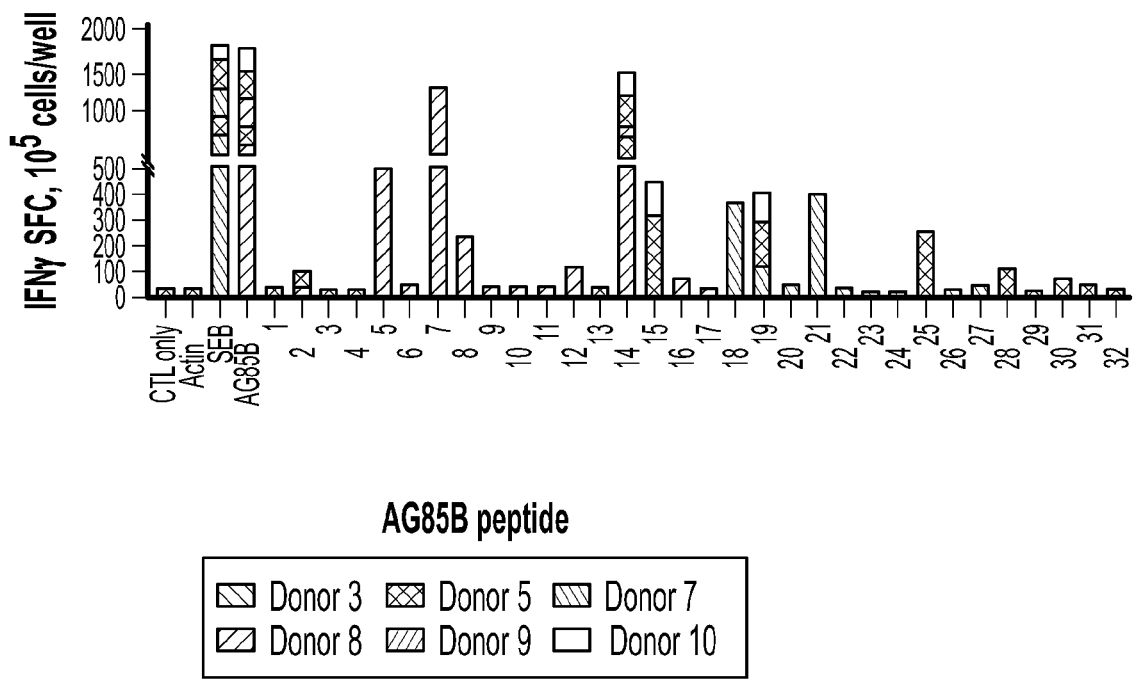
FIG. 7A depicts epitope mapping of AG85B and ESXB
Figure 7B:
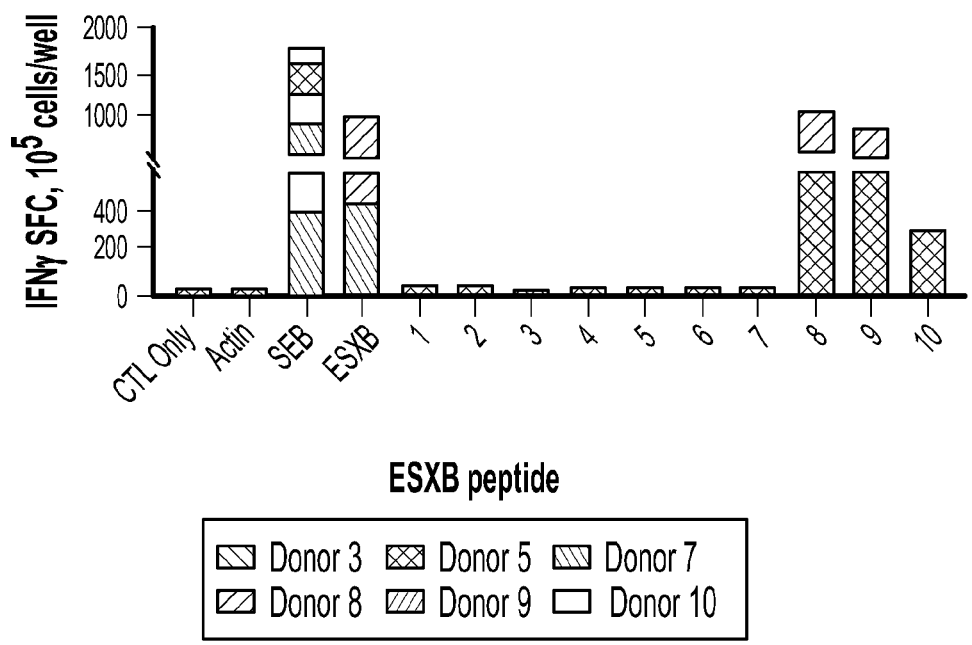
FIG. 7B depicts epitope mapping of AG85B and ESXB via IFN-γ ELISpot showed eight peptides from AG85B and three from ESXB recognized by MSTs from multiple healthy donors. SFC, spot forming colonies; SEB, staphylococcal enterotoxin B.

Mapping of epitope recognition within AG85B and ESXB utilizing IFN-$\gamma$ ELISPOT demonstrated several epitopes within each antigen that were recognized by multiple donors. Within AG85B, five donors recognized peptides #7 and 14, encompassing amino acid positions 61-75 and 131-145 (FIG. 7). Peptide 15 (AA 141-155) elicited a response in two donors, and Peptide 19 (AA 181-195) elicited a response in three donors. Within ESXB, peptides 8-10 at the C-terminus (AA 71-100) were recognized by three donors. Analysis of shared donor HLA alleles using predictive algorithms [NetMHC (http://www.cbs.dtu.dk/services/NetMHCII/), IEDB MHC Predictor (www.iedb.org)] (34, 35) suggested Class II MHC restrictions of the AG85B peptides through HLA DRB4 01:01, DPB1 04:01/02, DRB1 07:01, and DRB3 02:02, and Class II restrictions of ESXB peptides through HLA DQB1 03:01/02 and DRB4 01:01 (Table 1). Analysis of interspecies conservation of these epitopes showed a high degree of conservation of the AG85B epitopes (67-100%, FIG. 11), and low to moderate conservation of the ESXB epitopes (40-93%, FIG. 12).

Discussion

Mycobacterial infections are common in immunocompromised hosts, and treatment can be exceedingly challenging. Even among immunocompetent individuals, multi-drug resistant tuberculosis is an emerging problem, with resistance to first line antimycobacterial agents reported in 4% of new cases and 21% of previously treated cases worldwide (1). In infants with SCID or similarly profound forms of PID, clearance of mycobacterial infections is often impossible without restoration of T cell immunity (2). The use of repeated whole blood transfusions from a BCG-immunized sibling was reported as adjunctive therapy for an infant with SCID with improvement in BCGosis (36). Accordingly, adoptive immunotherapy targeting mycobacteria could be a useful adjunctive therapy alongside antibiotics.

Our analysis of the functionality of MSTs derived from healthy donors demonstrated that responses to the selected mycobacterial antigens were CD4+ restricted and polyfunctional. All donors (BCG vaccinated or otherwise) recognized at least one antigen. Analysis of responses between BCG-vaccinated and unvaccinated showed a difference in response magnitude on ELISPOT for PPE68, but not for the other four antigens. ESXA and ESXB were recognized by both donor groups, in spite of the fact that these genes are deleted in BCG. None of the donors had prior histories of tuberculosis infection. This may suggest that the reactivity to EXSA and ESXB (as well as the other antigens in the non-vaccinated donors) represents prior responses to other encountered mycobacterial species. If true, this would support the existence of cross-reactive epitopes shared amongst these species. Multiplex cytokine analysis showed consistent IFN-$\gamma$, TNF, and GM-CSF production in response to antigen restimulation, as well as IL-13 and MIP1a in a subset of donors. GM-CSF production has been described in the setting of experimental mycobacterial infection, though its role in human infection is less clear (37). IL-13 is a Th2 cytokine associated with fibrosis and mucus production, and was only noted in BCG-unvaccinated donors. It is possible that BCG vaccination maybe the cause of the absence of IL-13 in vaccinated donors, and may reinforce a Th1 skewed cytokine response to these antigens in vaccinated individuals. Many studies have highlighted the importance of Th1 CD4+ T cell responses in activating macrophages to control mycobacterial disease (38). In experimental models, Th2 cytokines have been associated with progression of mycobacterial infections, though in human tuberculosis, it is unclear if elevated Th2 cytokine profiles are a cause or consequence of mycobacterial infections.

In adoptive immunotherapy with partially HLA-matched virus-specific T cells, the HLA matching algorithm between the VST donor and recipient appears to be one of the key steps in improving the efficacy of this therapy, as identification of the HLA restriction of one or more immunodominant viral epitopes has correlated with antiviral activity in vivo (39). Mapping of mycobacterial epitopes and HLA restrictions would likely also be essential for "off the shelf" use of partially matched MSTs. Here, we describe several novel epitopes within AG85B and ESXB. Within AG85B, the recognized protein regions (AA 61-75, 131-145, 141-155, 180-195) were highly stable across species. Prior studies have shown that these regions are involved in secondary structure formation, which may explain their relative stability. Amino acids 181-195 overlapped with a domain in AG85B that was previously predicted to contain T cell epitopes and elicited ex vivo CD4+ T cell proliferation (31). Recognized epitopes within the C-terminus of ESXB were more variable across species. This region of the protein has been described to be essential for monocyte binding of the ESXB complex, and accordingly may play an important role in mycobacterial pathogenesis (40). It has been postulated that ESXA/ESXB deletion contributes to the attenuation of BCG. Further testing of additional donors with a wide breadth of HLA types would be needed to better understand the breadth of HLA restrictions of these antigens as well as the stability of epitopes in clinically isolated mycobacterial species. Comparison of published protein sequences across different mycobacterial species shows differing degrees of homology (Table 9).

TABLE 9

Antigen Conservation across Mycobacterial Species

| Antigen | Species | % Identify |
|---|---|---|
| AG85B | M. bovis | 100% |
| | M. kansasaii | 90% |
| | M. avium | 86% |
| | M. intracellulare | 87% |
| | M. ulcerans | 89% |

TABLE 9-continued

Antigen Conservation across Mycobacterial Species

| Antigen | Species | % Identify |
|---|---|---|
|  | M. marinum | 89% |
|  | M. abscessus | 64% |
|  | M. chelonae | 65% |
| PPE68 | M. bovis | 100% |
|  | M. kansasaii | 77% |
|  | M. avium | 51% |
|  | M. intracellulare | 50% |
|  | M. ulcerans | 60% |
|  | M. marinum | 74% |
|  | M. abscessus | 50% |
|  | M. chelonae | 49% |
| ESXA (ESAT-6*) | M. bovis * | 100% |
|  | M. kansasaii | 98% |
|  | M. avium | NA |
|  | M. intracellulare | 33% |
|  | M. ulcerans | 92% |
|  | M. marinum | 91% |
|  | M. abscessus | 48% |
|  | M. chelonae | 33% |
| ESXB (CFP-10*) | M. bovis * | 100% |
|  | M. kansasaii | 95% |
|  | M. avium | NA |
|  | M. intracellulare | NA |
|  | M. ulcerans | 95% |
|  | M. marinum | 97% |
|  | M. abscessus | 40% |
|  | M. chelonae | NA |
| P9WKF5 (ADK) | M. bovis | 100% |
|  | M. kansasaii | 95% |
|  | M. avium | 88% |
|  | M. intracellulare | 87% |
|  | M. ulcerans | 87% |
|  | M. marinum | 86% |
|  | M. abscessus | 71% |
|  | M. chelonae | 54% |

*ESXA and ESXB are deleted in BCG. NA = not available

The genomes of mycobacterial species average 2 MB with >2,000 described genes in many species. Accordingly, there are likely a vast number of immunogenic proteins beyond the five antigens tested in this study. However, use of M. tuberculosis lysate and M. avium Sensitin as non-biased antigen sources still yielded reactivity to the selected proteins. Though the breadth of antigen responses is likely much broader than the selected proteins, they were not overshadowed due to antigenic competition during expansion. Previous studies have similarly described cross reactivity between M. tuberculosis and non-tuberculous mycobacteria, though the biologic importance of immunologic responses to these shared antigens remains unclear (41).

There is also evidence that γ/δ T-cells are activated by phosphate antigens from mycobacteria, though their role in the control of mycobacterial infections remains unclear (42). However, we did not observe expansion of γ/δ T-cells even when utilizing whole cell lysates from M. tuberculosis, which contains lipids and carbohydrates in addition to proteins.

Though T cell immunity is clearly important for anti-mycobacterial defense, myeloid cells are also essential, as demonstrated by many forms of primary immunodeficiency such as GATA2 haploinsufficiency, IFNGR1/2 deficiency, Chronic granulomatous disease, and IRF8 deficiency. Of the tested patients with PID, responses to mycobacterial antigens were only found in two patients with NFKB1 haploinsufficiency (two of five antigens) and NEMO (one of five antigens). Responses were detectable in both tested patients with anti-IFN-γ autoantibodies, which was expected with ex vivo expansion of these patient's cells in the absence of patient serum. NFKB1 and related disorders have been well-described to cause impairment of T cell proliferation, and subtle T cell abnormalities have also been described in IFNGR1 deficiency (43, 44). T cell lymphopenia has been also described in GATA2 haploinsufficiency (45).

In this study, we have shown that mycobacterial-specific T cells can be reliably expanded from healthy donors using a rapid expansion protocol that is compatible with good manufacturing practices. Though T cell therapy alone would likely not be helpful for forms of PID with predominantly myeloid defects, one could envision usage of MSTs shortly after myeloid engraftment post-transplant in order to hasten recovery of T cell control of infection, which would otherwise not be expected to occur until months later. Though further work will be necessary to better characterize ideal donors, antigens, and T cell characteristics, T cell immunotherapy targeting mycobacteria could be a useful future treatment for patients with invasive mycobacterial infections.

Example 6—Evaluation of Mycobacteria-Specific T-Cell Function In Vivo

To evaluate biologic activity of Mycobacteria-specific T-cells in vivo, immunodeficient humanized NSG mice (hu-NSG) would be utilized. This model is immunodeficient and enables rapid engraftment of T-cells and other human cell lineages.

Mycobacterial species and methods of infection: NSG mice would be exposed to aerosolized mycobacteria (which could include M. avium strain Chester, or M. tuberculosis strain H37RV. Mycobacteria samples will be thawed and cultured for 4 weeks prior to mouse infection. Doses of 50-400 CFU would be utilized in 1 ml saline for aerosolization.

MST infusion: All MST cell infusions will be performed using fresh cells or thawed cells from a cryopreserved batch. Mice are anesthetized using isoflurane. Anesthesia is confirmed by lack of response with toe pinch and deep breathing in animals (once every 2 seconds). Cells will be slowly injected intravenously (2×104 to 10×106 cells/50 uL of PBS) using a gauge 27 needle. Control groups would be maintained who either receive MSTs alone without mycobacterial infection, or mycobacterial infection without MST infusion.

Clinical Observations. Following injection of tumors or immune cells or both, animals will be monitored daily for clinical signs and symptoms of the mycobacterial infection, with particular focus on respiratory symptoms. Mice would be followed for up to 12 weeks following infections. Survival time based on mycobacterial dosing and MST dose would be determined using a matrix grid.

The presence of one or more of the criteria below (from http://www.bu.edu/orecommittes/iacuc/policies-and-guidelines/tumor-policy-for-mice-and-rats/) is indication for euthanasia: impaired mobility (the inability to reach food and water), inability to remain upright, tumor interference with a vital physiological function (includes respiration, mastication, swallowing, urination, defecation or locomotion), location of the tumor on the animal's belly or its inner leg causing the tumor to be abraded or interfering with locomotion, hunched abnormal posture for >48 hours, labored breathing and cyanosis [bluish pinnae (ears) or feet or mucous membranes], clinical dehydration and/or prolonged decreased food intake, muscle atrophy and signs of lethargy and lack of physical activity, weight loss of more than 20% of body weight, chronic diarrhea for more than 48 hours, severe anemia (pale pinnae (ears) or feet or mucous membranes), bloodstained or mucopurulent discharge from any orifice, self-mutilation, lack of grooming behavior/ rough/unkempt hair coat for >48 hours, bulging eye, significant abdominal distension, behavioral changes, restlessness, seizures, or unconsciousness with no response to external stimuli.

Immunologic assays: Animal blood and tissue would be analyzed to presence of mycobacterial infection (via acid fast stain of tissue) and for presence and expansion the infused MSTs. Retroorbital bleeding would be performed for blood collection (http://web.jhu.edu/animalcare/procedures/retro-orbital.html). Standard heparinized or non-heparinized micro-hematocrit capillary tubes will be used for blood collection. Animals will be anesthetized with isoflurane prior to the procedure. MST analysis would be performed by Interferon-gamma ELISpot using mycobacterial pepmixes, and via flow cytometry to identify HLA proteins associated with the infused MST line. Intracellular cytokine staining will be performed to determine MST cytokine function at multiple time points in vivo.

The invention claimed is:

1. A method of expanding T cells ex vivo, the method comprising:
   culturing one or a plurality of T-cells;
   contacting the one or plurality of T-cells with:
   a polypeptide comprising an amino acid sequence coding for an Ag85B antigen at least 70% identical to SEQ ID NO: 6 from a *Mycobacterium* species,
   a polypeptide comprising an amino acid sequence coding for a PPE68 antigen at least 70% identical to SEQ ID NO: 7 from a *Mycobacterium* species,
   a polypeptide comprising an amino acid sequence coding for an ESXA antigen at least 70% identical to SEQ ID NO: 8 from a *Mycobacterium* species,
   a polypeptide comprising an amino acid sequence coding for an ESXB antigen at least 70% identical to SEQ ID NO: 9 from a *Mycobacterium* species, and
   a polypeptide comprising an amino acid sequence coding for an ADK antigen at least 70% identical to SEQ ID NO: 10 from a *Mycobacterium* species.

2. The method of claim 1, further comprising:
   isolating a sample from a subject prior to culturing the one or a plurality of T-cells and isolating T-cell from the samples; and/or
   stimulating the one or plurality of T-cells with one or more cytokines.

3. The method of claim 2, wherein the one or more cytokines is selected from the group consisting of IL-2, IL4, IL-6, IL-7, IL-15, IL-21, TNFβ and IFNα.

* * * * *